US012714704B2

(12) United States Patent
Bentley et al.

(10) Patent No.: US 12,714,704 B2
(45) **Date of Patent: *Aug. 25, 2026**

(54) CLEAVABLE CONJUGATES OF CATECHOL COMPOUNDS AND WATER-SOLUBLE POLYMERS AND METHODS OF TREATMENT USING THE SAME

(71) Applicant: Serina Therapeutics (AL), Inc., Huntsville, AL (US)

(72) Inventors: Michael Bentley, Huntsville, AL (US); Zhihao Fang, Madison, AL (US); Rebecca Weimer, Huntsville, AL (US); Tacey Viegas, Madison, AL (US); Randall Moreadith, Huntsville, AL (US)

(73) Assignee: Serina Therapeutics (AL), Inc., Huntsville, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/370,069

(22) Filed: Sep. 19, 2023

(65) Prior Publication Data

US 2024/0016798 A1 Jan. 18, 2024

Related U.S. Application Data

(63) Continuation of application No. 17/263,723, filed as application No. PCT/US2019/043820 on Jul. 27, 2019, now Pat. No. 11,766,432.

(60) Provisional application No. 62/711,427, filed on Jul. 27, 2018, provisional application No. 62/788,790, filed on Jan. 5, 2019.

(51) Int. Cl.

| | |
|---|---|
| ***A61K 31/485*** | (2006.01) |
| ***A61K 9/00*** | (2006.01) |
| ***A61K 31/05*** | (2006.01) |
| ***A61K 31/12*** | (2006.01) |
| ***A61K 31/137*** | (2006.01) |
| ***A61K 31/15*** | (2006.01) |
| ***A61K 31/198*** | (2006.01) |
| ***A61K 31/24*** | (2006.01) |
| ***A61K 31/277*** | (2006.01) |
| ***A61K 31/36*** | (2006.01) |
| ***A61K 31/55*** | (2006.01) |
| ***A61K 47/14*** | (2017.01) |
| ***A61K 47/18*** | (2017.01) |
| ***A61K 47/20*** | (2006.01) |
| ***A61K 47/22*** | (2006.01) |
| ***A61K 47/59*** | (2017.01) |

(52) U.S. Cl.

CPC .......... *A61K 31/485* (2013.01); *A61K 9/0019* (2013.01); *A61K 31/05* (2013.01); *A61K 31/12* (2013.01); *A61K 31/137* (2013.01); *A61K 31/15* (2013.01); *A61K 31/198* (2013.01); *A61K 31/24* (2013.01); *A61K 31/277* (2013.01); *A61K 31/36* (2013.01); *A61K 31/55* (2013.01); *A61K 47/14* (2013.01); *A61K 47/18* (2013.01); *A61K 47/20* (2013.01); *A61K 47/22* (2013.01); *A61K 47/59* (2017.08); *A61K 47/595* (2017.08)

(58) Field of Classification Search

CPC .... A61K 31/485; A61K 9/0019; A61K 31/05; A61K 31/12; A61K 31/137; A61K 31/15; A61K 31/198; A61K 31/24; A61K 31/277; A61K 31/36; A61K 31/55; A61K 47/14; A61K 47/18; A61K 47/20; A61K 47/22; A61K 47/595

See application file for complete search history.

(56) References Cited

U.S. PATENT DOCUMENTS 5,624,677 A 4/1997 El-Rashidy et al.
8,383,093 B1 * 2/2013 Moreadith .......... A61K 9/0019 424/78.3

(Continued)

FOREIGN PATENT DOCUMENTS

| | | |
|---|---|---|
| WO | 2013067199 | 5/2013 |
| WO | 2020264505 | 12/2020 |

OTHER PUBLICATIONS

Apomorphine. PubChem. Retrieved from the Internet on Oct. 6, 2024, https://pubchem.ncbi.nlm.nih.gov/compound/Apomorphine#section=2D-Structure. (Year: 2024).*

(Continued)

*Primary Examiner* — Lauren Wells

(74) *Attorney, Agent, or Firm* — Bradley Arant Boult Cummings LLP

(57) ABSTRACT

Described are conjugates comprising a water-soluble polymer linked to a compound comprising a catechol moiety via a cleavable linkage, wherein the cleavable linkage is formed between the water-soluble polymer and a first phenolic hydroxyl group of the catechol moiety and a second phenolic hydroxyl group of the catechol moiety is linked to a blocking group wherein the rate of hydrolytic release of the compound comprising the catechol moiety is controlled, at least in part, through structure or design of the blocking group on the second phenolic hydroxyl group of the catechol moiety. Therefore, the rate of hydrolytic release of the compound comprising the catechol moiety can be tuned through structural design of the group on the second phenolic hydroxyl group of the catechol moiety. Compounds used in the synthesis of the described conjugates and methods of using the described conjugate and other compounds in the treatment of dopamine-responsive disorders are also described.

27 Claims, 5 Drawing Sheets

(56) References Cited

U.S. PATENT DOCUMENTS

| | | | | |
|---|---|---|---|---|
| 8,597,633 | B2 | 12/2013 | Moreadith et al. | |
| 10,314,837 | B2 * | 6/2019 | Moreadith | A61K 31/7048 |
| 10,426,768 | B2 * | 10/2019 | Moreadith | A61P 25/08 |
| 11,224,595 | B2 * | 1/2022 | Moreadith | A61K 31/4045 |
| 11,298,350 | B2 * | 4/2022 | Moreadith | A61K 47/59 |
| 11,766,432 | B2 * | 9/2023 | Bentley | A61K 47/20 514/217.02 |
| 11,944,618 | B2 * | 4/2024 | Moreadith | A61K 47/542 |
| 2015/0246958 | A1 | 9/2015 | Han | |
| 2016/0303250 | A1 | 10/2016 | Moreadith et al. | |

OTHER PUBLICATIONS

Seeman P, Guan HC. Dopamine D1 and D2 receptors are sensitive to the cationic form of apomorphine. Mol Pharmacol. Dec. 1987; 32(6):760-3. PMID: 2961976. (Year: 1987).*

Extended European Search Report dated Nov. 22, 2022 of corresponding European Patent Application No. 19841823.8.

Baldessarini, Ross J. et al., "Hydrolysis of Diester Prodrugs of Apomorphine", Biochemical Pharmacology, vol. 26, pp. 1749-1756, 1977.

Di Stefano A, Sozio P, Cerasa L.S. Antiparkinson prodrugs, Molecules, Jan. 16, 2008;13(1):46-68, doi: 10.3390/molecules 13010046. PMID: 18259129; PMCID: PMC6244951. (Year: 2008).

Ashenhurst, J. Nucleophiles and Electrophiles, Master Organic Chemistry, Published Dec. 20, 2019, Retrieved from the internet on Jul. 20, 2022, https://www.studocu.com/row/document/jamaa%D8% A9-alkof%D8%A9/microelectronics-and-devices-and-ci/nucleophiles-and-electrophiles-master-organic-chemistry/11033686. (Year: 2019).

Young, Lee, "International Search Report and Written Opinion for PCT/US2019/043820" International Searching Authority; dated Oct. 24, 2019.

* cited by examiner

CLEAVABLE CONJUGATES OF CATECHOL COMPOUNDS AND WATER-SOLUBLE POLYMERS AND METHODS OF TREATMENT USING THE SAME

FIELD OF THE DISCLOSURE

The present disclosure relates generally to conjugates comprising a water-soluble polymer and a compound, wherein the compound is linked to the water-soluble polymer via a cleavable linkage. The present disclosure relates more specifically to conjugates comprising a water-soluble polymer and a compound comprising a catechol moiety, wherein the compound is linked to the water-soluble polymer via a cleavable linkage involving one of the two phenolic hydroxyl groups of the catechol moiety on the compound and the release of the compound from the conjugate is controlled, at least in part, by the structure of a group on the other of the two phenolic hydroxyl groups of the catechol moiety on the compound. The present disclosure also relates to intermediates useful in the synthesis of such conjugates, compounds with a catechol moiety comprising at least one blocking group, and methods of using such conjugates and compounds for the treatment of diseases and conditions, including, but not limited to, dopamine-responsive disorders.

BACKGROUND OF THE INVENTION

Compounds comprising a catechol moiety have been documented to have a number of beneficial properties and to be useful in the treatment of human disease. A particular class of compounds comprising a catechol moiety are dopamine receptor agonists. A representative compound is apomorphine. Apomorphine and other dopamine agonists are useful in treatment of dopamine-responsive disorders, such as, but not limited to, Parkinson's disease.

The common early treatment for Parkinson's disease utilizes levodopa. However, treatment with levodopa frequently leads to motor complications and "on-off" periods due to the short-acting nature of levodopa (and other orally administered drugs for the treatment of Parkinson's disease). Subcutaneous apomorphine has proven to be very effective in rapid reversal of these "off-periods," but apomorphine delivered in this manner is effective for only a limited period since apomorphine has a very short half-life in-vivo.

Oral administration of apomorphine is not effective as the oral bioavailability is only 1.7%, primarily due to hepatic first pass metabolism. A buccal delivery formulation for apomorphine has also been developed, but this formulation requires frequent use and can result in stomatitis and dental caries. Lipid-based prodrugs have also been shown to improve drug half-life in-vivo but have not significantly improved hydrolysis profiles (for example, due to hepatic metabolism).

The period of delivery of apomorphine can be extended through use of a microneedle pump patch (available under the brand Apo-Go in Europe). The use of the microneedle pump patch requires daily re-localization of the patch and the involvement of a healthcare professional. This approach is obviously inconvenient at best and is likely to be uncomfortable due to the use of the microneedle patch. In addition, this approach may cause a burning sensation in the skin of the user, skin nodules and skin infections.

There is clearly a need for improvement in the delivery of compounds containing catechol moieties (as exemplified by apomorphine) for the treatment of diseases and conditions, including, but not limited to, dopamine-responsive disorders. The present disclosure provides a solution to the problems in the art by providing compounds comprising a catechol moiety comprising at least one blocking group on a phenolic hydroxyl of the catechol moiety, polymer conjugates of compounds comprising a catechol moiety that provides for sustained pharmacokinetics, increased bioavailability, ease of administration and/or decreased side effects when administered to a subject.

DETAILED DESCRIPTION

Definitions

Figure 1:
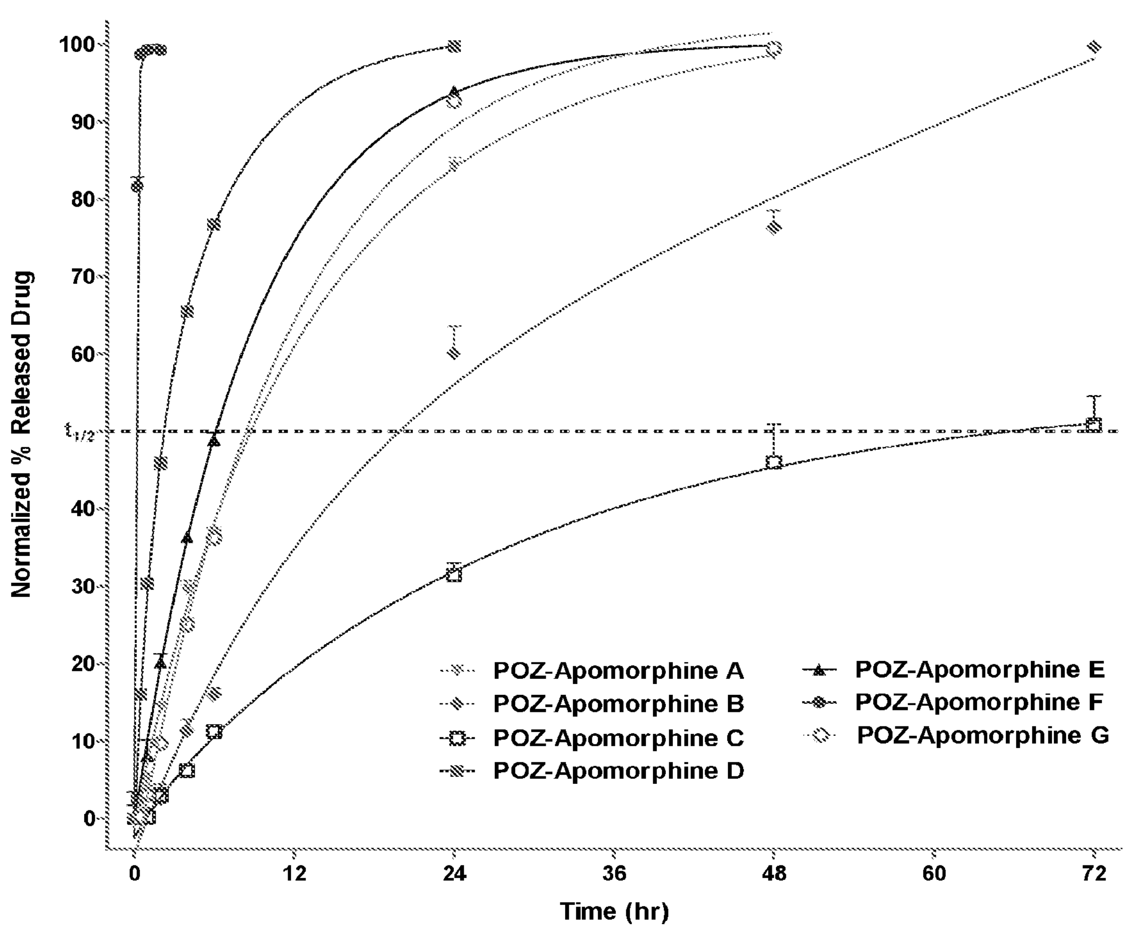
FIG. 1 shows the hydrolysis rates of the POZ-Apomorphine conjugates of Examples 6 (Apo-A; inverted triangle), Example 7 (Apo-B; diamond), Example 8 (Apo-C; empty square), Example 9 (Apo-F; filled circle), Example 12 (Apo-D; filled square), Example 13 (Apo-E; triangle), and Example 15 (Apo-G; empty circle). The calculated $t_{1/2}$ values are also shown for each POZ-Apomorphine conjugate.

As used herein, the term "active" or "activated" when used in conjunction with a particular functional group refers to a reactive functional group that reacts readily with an electrophile or a nucleophile on another molecule. This is in contrast to those groups that require catalysts or impractical reaction conditions in order to react (i.e., a "non-reactive" or "inert" group).

As used herein, the term "bond", "link", "linked" or "linkage" when used with respect to a polymer or compound described herein, or components thereof, refers to bonds that normally are formed as the result of a chemical reaction and typically are covalent bonds.

As used herein, the term "cleavable linkage", "cleavable linker", "hydrolysable linker", "hydrolysable functionality", "releasable linker" or "releasable functionality" refers to a chemical linkage containing a cleavable moiety. The terms hydrolysable and releasable do not imply any particular mechanism by which the linker is cleaved.

As used herein, the term "cleavable moiety" refers to a group (such as in a cleavable linkage) that is cleavable in a subject in-vivo under physiological conditions in the subject after a conjugate of the present disclosure has been administered to the subject. In one embodiment, the cleavable moiety is cleaved by a chemical reaction. In one aspect of this embodiment, the cleavage is by hydrolysis of an ester group or reduction, such as, but not limited to, reduction of a disulfide. In one embodiment, the cleavable moiety is cleaved by a substance that is naturally present or induced to be present in the subject. In one aspect of this embodiment, such a substance is an enzyme or polypeptide. Therefore, in one embodiment, the cleavable moiety is cleaved by an enzymatic reaction. In one embodiment, the cleavable moiety is cleaved by a combination of the foregoing.

As used herein, the term "inert" or "non-reactive" when used in conjunction with a particular functional group refers to a functional group that does not reacts readily with an electrophile or a nucleophile on another molecule and require catalysts or impractical reaction conditions in order to react.

As used herein, the term "first phenolic hydroxyl" or "first hydroxyl" refers to the hydroxyl group on the catechol moiety that is linked to the water-soluble polymer, including a polyoxazoline polymer, via a direct linkage or a linking group. It is understood that the terms "first phenolic hydroxyl" or "first hydroxyl" do not refer to a specific hydroxyl group of the catechol moiety or refer to a specific location of the hydroxyl group on the compound.

As used herein, the term "second phenolic hydroxyl" or "second hydroxyl" refers to the hydroxyl group on the catechol moiety that is adjacent to (i.e., ortho to) the first phenolic hydroxyl group. It is understood that the terms "second phenolic hydroxyl" or "second hydroxyl" do not refer to a specific hydroxyl group of the catechol moiety or refer to a specific location of the hydroxyl group on the compound.

As used herein, the term "alkyl", whether used alone or as part of a substituent group, is a term of art and refers to saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight-chain or branched-chain alkyl has about 30 or fewer carbon atoms in its backbone (e.g., $C_1$-$C_{30}$ for straight chain, $C_3$-$C_{30}$ for branched chain), and alternatively, about 20 or fewer, or 10 or fewer. In certain embodiments, the term "alkyl" refers to a $C_1$-$C_{10}$ straight-chain alkyl group. In certain embodiments, the term "alkyl" refers to a $C_1$-$C_6$ straight-chain alkyl group. In certain embodiments, the term "alkyl" refers to a $C_3$-$C_{12}$ branched-chain alkyl group. In certain embodiments, the term "alkyl" refers to a $C_3$-$C_8$ branched-chain alkyl group. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

As used herein, the term "heteroalkyl" refers to a straight- or branched-chain alkyl group preferably having from 2 to 14 carbons in the chain, one or more of which has been replaced by a heteroatom selected from S, O, and N. Exemplary heteroalkyls include alkyl ethers, secondary and tertiary alkyl amines, amides, alkyl sulfides, and the like, wherein the heteroatom may be optionally substituted.

As used herein, the term "alkenyl", whether used alone or as part of a substituent group, is a term of art and refers to unsaturated aliphatic groups, including, a straight or branched chain hydrocarbon radical containing from 2 to 30 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl. The unsaturated bond(s) of the alkenyl group can be located anywhere in the moiety and can have either the (Z) or the (E) configuration about the double bond(s). An alkenyl group may be optionally substituted.

As used herein, the term "alkynyl", whether used alone or as part of a substituent group, is a term of art and refers to unsaturated aliphatic groups, including, straight or branched chain hydrocarbon radical containing from 2 to 30 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl. An alkynyl group may be optionally substituted.

The phrase "substituted alkyl", "substituted heteroalkyl", "substituted alkenyl", and "substituted alkynyl" refers to alkyl, heteroalkyl, alkenyl and alkynyl groups as defined above in which one or more bonds to a carbon(s) or hydrogen(s) are replaced by a bond to non-hydrogen or non-carbon atoms such as, but not limited to, a halogen atom in halides such as F, Cl, Br, and I; and oxygen atom in groups such as carbonyl, carboxyl, hydroxyl groups, alkoxy groups, aryloxy groups, heterocyclyloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, enamines imines, oximes, hydrazones, heterocyclylamine, (alkyl)(heterocyclyl)-amine, (aryl)(heterocyclyl)amine, diheterocyclylamine, and nitriles; a silicon atom in groups such as in trialkylsilyl groups, dialkylarylsilyl groups, alkyldiarylsilyl groups, and triarylsilyl groups; and other heteroatoms in various other groups. In certain embodiments, the term "substituted alkyl" or "substituted heteroalkyl" refers to a $C_1$-$C_{14}$ straight- or branched-chain alkyl or heteroalkyl group that is substituted with up to 5 groups selected from the group consisting of —OH, $—NH_2$, $—NH—NH_2$, =O(OH), substituted aryl, and =0.

The term "halo" or "halogen" whether used alone or as part of a substituent group, is a term of art and refers to —F, —Cl, —Br, or —I.

The term "alkoxy", whether used alone or as part of a substituent group, is a term of art and refers to an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "aralkyl" or "arylalkyl", whether used alone or as part of a substituent group, is a term of art and refers to an alkyl group substituted with an aryl group, wherein the moiety is appended to the parent molecule through the alkyl group. An arylalkyl group may be optionally substituted. A "substituted aralkyl" has the same meaning with respect to unsubstituted aralkyl groups that substituted aryl groups had with respect to unsubstituted aryl groups. However, a substituted aralkyl group also includes groups in which a carbon or hydrogen bond of the alkyl part of the group is replaced by a bond to a non-carbon or a non-hydrogen atom.

The term "heteroaralkyl" or "heteroarylalkyl", whether used alone or as part of a substituent group, is a term of art and refers to an alkyl group substituted with a heteroaryl group, wherein the moiety is appended to the parent molecular moiety through the alkyl group. A heteroarylalkyl may be optionally substituted. The term "substituted heteroarylalkyl" has the same meaning with respect to unsubstituted heteroarylalkyl groups that substituted aryl groups had with respect to unsubstituted aryl groups.

The term "heterocyclylalkyl", whether used alone or as part of a substituent group, is a term of art and refers to unsubstituted or substituted alkyl, alkenyl or alkynyl groups in which a hydrogen or carbon bond of the unsubstituted or substituted alkyl, alkenyl or alkynyl group is replaced with a bond to a heterocyclyl group. A heterocyclylalkyl may be optionally substituted. The term "substituted heterocyclylalkyl" has the same meaning with respect to unsubstituted heterocyclylalkyl groups that substituted aryl groups had with respect to unsubstituted aryl groups. However, a substituted heterocyclylalkyl group also includes groups in which a non-hydrogen atom is bonded to a heteroatom in the heterocyclyl group of the heterocyclylalkyl group such as, but not limited to, a nitrogen atom in the piperidine ring of a piperidinylalkyl group.

The term "aryl", whether used alone or as part of a substituent group, is a term of art and refers to includes monocyclic, bicyclic and polycyclic aromatic hydrocarbon groups, for example, benzene, naphthalene, anthracene, and pyrene. The aromatic ring may be substituted at one or more ring positions with one or more substituents, such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. The term "aryl" also includes polycyclic ring systems having two or more cyclic rings in which two or more carbons are common to two adjoining rings (the rings are "fused rings") wherein at least one of the rings is an aromatic hydrocarbon, e.g., the other cyclic rings may be cycloalkyls, cycloalkenyls, cycloalkynyls, aryls, heteroaryls, and/or heterocyclyls. In certain embodiments, the term "aryl" refers to a phenyl group. The aryl group may be optionally substituted. A "substituted aryl" includes aryl groups in which one of the aromatic carbons is bonded to a non-carbon or non-hydrogen atom, such as, but not limited to, those atoms described above with respect to a substituted alkyl, and also includes aryl groups in which one or more aromatic carbons of the aryl group is bonded to a substituted and/or unsubstituted alkyl, alkenyl, or alkynyl group as defined herein. This includes bonding arrangements in which two carbon atoms of an aryl group are bonded to two atoms of an alkyl, alkenyl, or alkynyl group to define a fused ring system (e.g. dihydronaphthyl or tetrahydronaphthyl). Thus, the phrase "substituted aryl" includes, but is not limited to tolyl, and hydroxyphenyl among others.

The term "cycloalkyl", whether used alone or as part of a substituent group, is a term of art and refers to a saturated carbocyclic group containing from three to six ring carbon atoms, wherein such ring may optionally be substituted with a substituted or unsubstituted alkyl group or a substituent as described for a substituted alkyl group. Exemplary cycloalkyl groups include, but are not limited to, cyclopropyl, cyclobutyl, cyclopentyl, cyclohexyl, 2-methylcyclobutyl and 4-ethylcyclohexyl.

The term "heteroaryl", whether used alone or as part of a substituent group, is a term of art and refers to a monocyclic, bicyclic, and polycyclic aromatic group having 3 to 30 total atoms including one or more heteroatoms such as nitrogen, oxygen, or sulfur in the ring structure. Exemplary heteroaryl groups include azaindolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl, and the like. The "heteroaryl" may be substituted at one or more ring positions with one or more substituents such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. The term "heteroaryl" also includes polycyclic ring systems having two or more cyclic rings in which two or more carbons are common to two adjoining rings (the rings are "fused rings") wherein at least one of the rings is an aromatic group having one or more heteroatoms in the ring structure, e.g., the other cyclic rings may be cycloalkyls, cycloalkenyls, cycloalkynyls, aryls, heteroaryls, and/or heterocyclyls.

The term "heterocyclyl", whether used alone or as part of a substituent group, is a term of art and refers to a radical of a non-aromatic ring system, including, but not limited to, monocyclic, bicyclic, and tricyclic rings, which can be completely saturated or which can contain one or more units of unsaturation, for the avoidance of doubt, the degree of unsaturation does not result in an aromatic ring system, and having 3 to 15 atoms including at least one heteroatom, such as nitrogen, oxygen, or sulfur. For purposes of exemplification, which should not be construed as limiting the scope of this invention, the following are examples of heterocyclic rings: aziridinyl, azirinyl, oxiranyl, thiiranyl, thiirenyl, dioxiranyl, diazirinyl, diazepanyl, 1,3-dioxanyl, 1,3-dioxolanyl, 1,3-dithiolanyl, 1,3-dithianyl, imidazolidinyl, isothiazolinyl, isothiazolidinyl, isoxazolinyl, isoxazolidinyl, azetyl, oxetanyl, oxetyl, thietanyl, thietyl, diazetidinyl, dioxetanyl, dioxetenyl, dithietanyl, dithietyl, dioxalanyl, oxazolyl, thiazolyl, triazinyl, isothiazolyl, isoxazolyl, azepines, azetidinyl, morpholinyl, oxadiazolinyl, oxadiazolidinyl, oxazolinyl, oxazolidinyl, oxopiperidinyl, oxopyrrolidinyl, piperazinyl, piperidinyl, pyranyl, pyrazolinyl, pyrazolidinyl, pyrrolinyl, pyrrolidinyl, quinuclidinyl, thiomorpholinyl, tetrahydropyranyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. A heterocyclyl group may be substituted at one or more ring positions with one or more substituents such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like.

The terms "treatment", "treat" and "treating" refers a course of action (such as administering a conjugate as described herein or pharmaceutical composition comprising a conjugate as described herein) so as to prevent, eliminate, or reduce a symptom, aspect, or characteristics of a disease or condition. Such treating need not be absolute to be useful. In one embodiment, treatment includes a course of action that is initiated concurrently with or after the onset of a symptom, aspect, or characteristics of a disease or condition. In another embodiment, treatment includes a course of action that is initiated before the onset of a symptom, aspect, or characteristics of a disease or condition.

The term "in need of treatment" refers to a judgment made by a caregiver that a patient requires or will benefit from treatment. This judgment is made based on a variety of factors that are in the realm of a caregiver's expertise, but that includes the knowledge that the patient is ill, or will be ill, as the result of a disease or condition that is treatable by a method or compound of the disclosure.

The terms "individual", "subject", or "patient" refers to any animal, including mammals, such as mice, rats, other rodents, rabbits, dogs, cats, swine, cattle, sheep, horses, or primates, and humans. The terms may specify male or female or both, or exclude male or female. In a preferred embodiment, the terms "individual", "subject", or "patient" refers to a human.

The term "therapeutically effective amount" refers to an amount of a conjugate or compound, either alone or as a part of a pharmaceutical composition, that is capable of having any detectable, positive effect on any symptom, aspect, or characteristics of a disease or condition. Such effect need not be absolute to be beneficial.

Certain compounds contained in the conjugates and/or compositions of the present disclosure may exist in particular geometric or stereoisomeric forms. In addition, compounds o contained in the conjugates and/or compositions of the present disclosure may also be optically active. The present disclosure contemplates all such compounds, including cis- and trans-isomers, (R)- and (S)-enantiomers, diastereoisomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, fragmentation, decomposition, cyclization, elimination, or other reaction.

It will be understood that when a group is specified as a part of a compound, the substitution of the group may be adjusted to accommodate the particular bonds. For example, when an alkyl group is joined to two other groups, the alkyl group is considered an alkylene group.

The term "substituted" is also contemplated to include all permissible substituents of organic compounds. In a broad aspect, the permissible substituents include acyclic and cyclic, branched and unbranched substituents, carbocyclic and heterocyclyl, aromatic and nonaromatic substituents of organic compounds. Illustrative substituents include, for example, those described herein above. For purposes of this disclosure, the heteroatoms, such as oxygen or nitrogen, may have hydrogen substituents and/or any permissible substituents of organic compounds described herein which satisfy the valences of the heteroatoms. Exemplary substitutions include, but are not limited to, hydroxy, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. This invention is not intended to be limited in any manner by the permissible substituents of organic compounds.

Other chemistry terms herein are used according to conventional usage in the art, as exemplified by The McGraw-Hill Dictionary of Chemical Terms (ed. Parker, S., 1985), McGraw-Hill, San Francisco, incorporated herein by reference). Unless otherwise defined, all technical and scientific terms used herein have the same meaning as commonly understood by one of ordinary skill in the art to which this invention pertains.

The term "pharmaceutically acceptable salt" as used herein includes salts derived from inorganic or organic acids including, for example, hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2-sulfonic, and other acids. Pharmaceutically acceptable salt forms can include forms wherein the ratio of molecules comprising the salt is not 1:1. For example, the salt may comprise more than one inorganic or organic acid molecule per molecule of base, such as two hydrochloric acid molecules per molecule of conjugate. As another example, the salt may comprise less than one inorganic or organic acid molecule per molecule of base, such as two molecules of conjugate per inorganic or organic acid molecule.

The terms "carrier" and "pharmaceutically acceptable carrier" as used herein refer to a diluent, adjuvant, excipient, or vehicle with which a compound is administered or formulated for administration. Non-limiting examples of such pharmaceutically acceptable carriers include liquids, such as water, saline, and oils; and solids, such as gum acacia, gelatin, starch paste, talc, keratin, colloidal silica, urea, and the like. In addition, auxiliary, stabilizing, thickening, lubricating, flavoring, and coloring agents may be used. Other examples of suitable pharmaceutical carriers are described in *Remington's Pharmaceutical Sciences* by E. W. Martin, herein incorporated by reference in its entirety.

INTRODUCTION

Previous patents from the applicant have addressed the problems associated with the administration of dopamine agonists (exemplified by rotigotine and ropinirole) to subjects by providing a conjugate comprising a polyoxazoline polymer linked to the dopamine agonists via a linking group comprising a cleavable moiety (for example, an ester group), wherein the structure of the linking group provides controlled release of the dopamine agonist from the polyoxazoline polymer in-vivo. In animal studies and in human clinical trials, pharmacokinetics of rotigotine hydrolysis demonstrated a steady-state delivery suitable for weekly subcutaneous injections.

In additional investigations, when this approach was taken with the dopamine agonist apomorphine wherein the apomorphine was linked to the polymer via a linking group comprising an ester moiety as the cleavable moiety at one of the 2 phenolic hydroxyl groups of the catechol moiety, apomorphine was released at a much faster rate in human plasma than was expected or desired. Further, the structure of the linking group was not shown to provide the desired control over the release rate as was seen for the rotigotine polymer conjugate.

Apomorphine is a compound that comprises a catechol moiety. The structure of apomorphine is provided below, with the two adjacent phenolic hydroxyl groups characteristic of a catechol moiety present at the 10 and 11 positions of apomorphine. Therefore, apomorphine (and compounds comprising a catechol moiety in general) have a first and a second phenolic hydroxyl group.

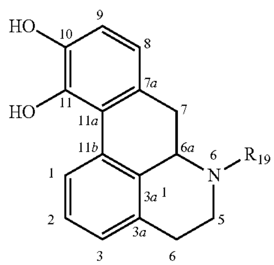

While not being bound by any particular theory, it is believed that the neighboring group participation by the free adjacent phenolic hydroxyl (the hydroxyl group not linked via the linking group to the polymer) causes, at least in part, the rapid cleavage of the cleavable moiety in the linking group (in this case an ester group) and accounts for the fact that the structure of the linking group failed to provide the desired control over the release rate of apomorphine from the polyoxazoline polymer.

In the present disclosure, a novel approach for the administration of compounds comprising a catechol moiety, including dopamine agonists, is provided. Specifically, the present disclosure provides for a conjugate comprising a water-soluble polymer and a compound comprising a catechol moiety, wherein the compound is linked to the polymer via a linkage (for example, a direct linkage between the polymer and the first hydroxyl or a linking group) comprising a first cleavable moiety to a first phenolic hydroxyl of the catechol moiety, and the cleavage of the first cleavable moiety on the linkage is controlled, at least in part, through the structure of a blocking group on a second phenolic hydroxyl of the catechol moiety. In certain embodiments, the linkage is a linking group. In certain embodiments, the first phenolic hydroxyl group is generated when the first cleavable moiety is cleaved. In certain embodiments, the blocking group contains a second cleavable moiety such that the second phenolic hydroxyl group is generated when the second cleavable moiety is cleaved. The blocking group is not linked directly to the water-soluble polymer.

In one embodiment, a free hydroxyl group is generated at the second phenolic hydroxyl of the catechol moiety when the second cleavable moiety is cleaved. In one embodiment, a free hydroxyl group is generated at the first phenolic hydroxyl of the catechol moiety when the first cleavable moiety is cleaved. In one embodiment, a free hydroxyl group is generated at both the first phenolic hydroxyl and the second phenolic hydroxyl of the catechol moiety when the first and second cleavable moieties are cleaved. In one embodiment, at least one of the first and second cleavable moieties are positioned and/or structured, such that when the first and/or second cleavable moiety is cleaved, a free hydroxyl group is generated at the first and/or second phenolic hydroxyl of the catechol moiety. In one embodiment, each of the first and second cleavable moieties are positioned and/or structured, such that when the first and second cleavable moieties are cleaved, a free hydroxyl group is generated at the first and second phenolic hydroxyl of the catechol moiety.

While not being bound by any particular theory, it is believed that the blocking group blocks or inhibits the neighboring group participation by the second phenolic hydroxyl and slows the cleavage of the first cleavable moiety in the linkage. The structure of the blocking group can be altered to provide control over the cleavage of the first cleavable moiety and the release kinetics of the compound from the polymer.

The described conjugates provide for sustained pharmacokinetics, increased bioavailability and/or ease of administration of the compound comprising a catechol moiety. In certain embodiments, the described conjugates provide for decreased side effects when administered to a subject (as compared to the unconjugated compound administered in a suitable formulation). In one aspect of this embodiment, the side effect is a dermal reaction at the site of administration.

Water-Soluble Polymer Conjugates

The present disclosure provides polymer conjugates consisting of, consisting essentially of, or comprising a water-soluble polymer and a compound comprising a catechol moiety. In one embodiment, the linkage is a direct linkage and the compound is linked to the polymer backbone via a direct linkage through a reactive group on the compound (preferably the first phenolic hydroxyl) and a reactive group on the polymer. In one embodiment, the direct linkage contains at least a first cleavable moiety such that in-vivo under physiological conditions in the body of a subject, such as, but not limited to, a human, the compound is released from the polymer after administration of the polymer conjugate to the subject. The direct linkage may form the first cleavable moiety in the reaction linking the polymer to the compound. Such cleavable moieties are discussed herein.

In an alternate embodiment, the linkage is via a linking group and the compound is linked to the polymer through a linking group to a reactive group on the compound (preferably the first phenolic hydroxyl). In one embodiment, the linking group contains at least a first cleavable moiety such that in-vivo under physiological conditions in the body of a subject, such as, but not limited to, a human, the compound is released from the polymer after administration of the polymer conjugate to the subject. Such cleavable moieties are discussed herein. In one embodiment, the linking group contains, in addition to the first cleavable moiety, a group capable of forming a linkage with a reactive group on the polymer, and a group capable of forming a linkage with a reactive group on the compound.

As discussed herein, the cleavage of first cleavable moiety of the linkage is controlled, at least in part, through the structure of a blocking group on the second phenolic hydroxyl of the catechol moiety.

For convenience and clarity, the specification describes the direct linkage or linking group reacting with the first phenolic hydroxyl and the blocking group as reacting with the second phenolic hydroxyl. The person of skill in the art would understand that the situation could be reversed.

In a general embodiment, the polymer conjugate of the present disclosure may be represented by the general formula I, or a pharmaceutically acceptable salt thereof.

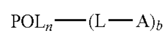

I wherein,

POL is a water-soluble polymer;

n is 1-1000 and represents the number of monomer units comprising the water-soluble polymer;

b is 1 to 50, provided that n is always greater than or equal to b;

A is a compound comprising a catechol moiety, the catechol moiety comprising at least a first and a second phenolic hydroxyl group, wherein the compound is linked to the polymer via the first phenolic hydroxyl group and the second phenolic hydroxyl group is optionally linked to a blocking group; and L is a linkage comprising a first cleavable moiety, linking the compound (A) and the polymer (POL).

In certain embodiments, L is a linking group comprising a first cleavable moiety. In certain embodiments, L is a direct linkage, wherein the direct linkage comprises the first cleavable moiety (in certain aspects, the direct linkage forms the first cleavable moiety in the reaction linking the polymer to the compound).

Exemplary compounds suitable for A are described herein. In one embodiment, A is a compound of the formula III. In one embodiment, A is a compound of the formula IV. In one embodiment, A is a compound of the formula IV where $R_{19}$ is $CH_3$.

In one embodiment, the first phenolic hydroxyl is modified by forming the linkage with the polymer portion. In one embodiment, the oxygen atom of the first phenolic hydroxyl participates in formation of the linkage with the polymer portion. Formation of the linkage may comprise the formation of a chemical bond between the first phenolic hydroxyl (for example, the oxygen atom) and an atom or group on the polymer or the linking group. In one embodiment, the second phenolic hydroxyl is modified through a reaction with the blocking group. In one embodiment, the oxygen atom of the second phenolic hydroxyl participates in formation of a bond with the blocking group. Formation of the chemical bond may be between the first phenolic hydroxyl (for example, the oxygen atom) and an atom or group on the blocking group. In each of the forgoing embodiments, the modification of the first and/or second phenolic hydroxyl may result in the formation of an ester linkage, wherein the ester linkage comprises the oxygen atom of the first and/or second phenolic hydroxyl groups. In each of the forgoing embodiments, the modification of the first and/or second phenolic hydroxyl may result in the formation of an ester linkage, wherein the ester linkage comprises the oxygen atom of the first and/or second phenolic hydroxyl groups and the ester linkage forms the first and/or second cleavable moieties. Therefore, in certain embodiments, the first and the second cleavable moieties are the same. Therefore, in certain embodiments, the first cleavable moiety is an ester linkage, the second cleavable moiety is an ester linkage, or both the first cleavable moiety and the second cleavable moiety are ester linkages.

The polymer portion of the disclosed polymer conjugates may take on a variety of forms. In certain embodiments, the polymer is a poly(oxazoline) (POZ), poly(5,6-dihydro-4h-1,3-oxazine), a dextran, a dextran modified by oxidation, a polyethylene glycol (PEG), a poly(hydroxypropylmethacrylate), a polyglutamic acid, a polylactic-polyglutamic acid mixture, a polysialic acid, a polycaprolactone, a polyvinylpyrrolidone, a glycosaminoglycans, a polyglycerol, a poly(acryloyloxyethylphosphorylcholine), or a methacrylate-based co-polymer with synthetic forms of phosphorylcholine; combinations of the foregoing are also included.

In one embodiment, the polymer is a POZ polymer. In still another embodiment, the polymer is a PEG polymer. In still another embodiment, the polymer is a dextran polymer. In still another embodiment, the polymer is a dextran polymer modified by oxidation.

In one embodiment, wherein the water-soluble polymer is a co-polymer, the co-polymer may be manufactured by reacting one of more monomer units of a first water-soluble polymer and one or more monomer units of at least a second polymer (which may optionally be a water-soluble polymer). Such a co-polymer includes both block co-polymers and random co-polymers. In a particular aspect, the co-polymer comprises a POZ polymer and at least a second polymer. In a particular aspect, the co-polymer comprises a POZ polymer and at least a second polymer, wherein the POZ polymer portion is comprises greater than 25%, 50%, 75%, 85%, 95%, 98%, 99%, or 99.5% of the polymer (on a weight to weight basis with regard to the total polymer components). In a particular aspect, the co-polymer comprises a POZ polymer and at least a second polymer, wherein the POZ polymer is comprises greater than 25%, 50%, 75%, 85%, 95%, 98%, 99%, or 99.5% of the polymer (on a weight to weight basis with regard to the total polymer components) and at least one of the additional polymers is a water-soluble polymer. In any of the foregoing, the additional water-soluble polymer(s) may be any water-soluble polymer described above. In any of the foregoing, the additional polymer(s) may be PEG, dextran, and/or dextran modified by oxidation. In a particular aspect, the co-polymer comprises a POZ polymer and at least a second polymer, wherein the POZ polymer is comprises greater than 25%, 50%, 75%, 85%, 95%, 98%, 99%, or 99.5% of the polymer (on a weight to weight basis) and the additional polymer(s) is not a water-soluble polymer.

L may form a linkage with any reactive group on the polymer and a reactive group on the compound, suitably the first phenolic hydroxyl group on the catechol moiety of the compound. In one embodiment, L is a linkage between the compound and a terminal end of the polymer. In one embodiment, L is a linkage between the compound and a side chain group of the polymer (referred to herein as a "pendent" position or a "pendent"). Furthermore, L may include component(s) of a group that was originally present on the polymer and/or the compound.

Suitable parameters for L are described herein. In a particular embodiment, L is a linking group containing a first cleavable moiety.

In a particular embodiment, the polymer conjugates of the present disclosure may be represented by the general formula II, or a pharmaceutically acceptable salt thereof.

II

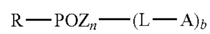

wherein,

R is an initiating group;

POZ is a polyoxazoline polymer;

n is 1-1000 and represents the number of monomer units comprising the polyoxazoline polymer;

b is 1 to 50, provided that n is always greater than or equal to b;

A is a compound comprising a catechol moiety, the catechol moiety comprising at least a first and a second phenolic hydroxyl group, wherein the compound is linked to the polymer via the first phenolic hydroxyl group and the second phenolic hydroxyl group is optionally linked to a blocking group; and L is a linkage comprising a first cleavable moiety, linking the compound (A) and the polymer (POL).

In a particular embodiment, the POZ conjugate of the present disclosure is represented by the general formula IIA, or a pharmaceutically acceptable salt thereof, wherein the linkage between the compound and the polymer is formed at the "pendent" position.

IIA

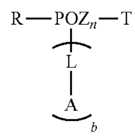

wherein

R is an initiating group;

POZ is a polyoxazoline polymer;

n is 1-1000 and represent the number of monomer units comprising the polyoxazoline polymer;

b is 1 to 50, provided that n is always greater than or equal to b;

A is a compound comprising a catechol moiety, the catechol moiety comprising at least a first and a second phenolic hydroxyl group, wherein the compound is linked to the polymer via the first phenolic hydroxyl group and the second phenolic hydroxyl group is optionally linked to a blocking group;

L is a linkage comprising a first cleavable moiety, linking the compound (A) and the polymer (POL); and T is a terminating group.

In another particular embodiment, the POZ conjugate of the present disclosure may be represented by the general formula JIB, or a pharmaceutically acceptable salt thereof, wherein the linkage between the compound and the polymer is formed at the "pendent" position.

IIB $$R\text{-}\{[N(COX)CH_2CH_2]_{o1}\text{-}[N(COY)CH_2CH_2]_{o2}\text{-}[N(COR_1)CH_2CH_2]_n\}_a\text{-}T$$

wherein

R is an initiating group;

A is a compound comprising a catechol moiety, the catechol moiety comprising at least a first and a second phenolic hydroxyl group, wherein the compound is linked to the polymer via the first phenolic hydroxyl group and the second phenolic hydroxyl group is optionally linked to a blocking group;

L is a linkage comprising a first cleavable moiety, linking the compound (A) and the polymer (POL);

$R_1$ is a non-reactive pendent moiety and is independently selected for each repeating unit;

X is independently selected for each repeating unit from -L-A;

Y is independently selected for each repeating unit from -L-A, a non-reactive pendent moiety, or a pendent moiety containing an active functional group;

a is ran which indicates a random co-polymer or block which indicates a block co-polymer o1 is an integer from 1 to 50;

o2 is and from 0 to 49, provided that the sum of o1 and o2 is less than or equal to 50;

n is an integer from 1 to 1000; and

T is a terminating group.

Unless otherwise specified, the following descriptions apply to each of the conjugates of the formula II, IIA, and IIB.

In certain embodiments, L is a linking group comprising a first cleavable moiety. In certain embodiments, L is a direct linkage, wherein the direct linkage comprises the first cleavable moiety (in certain aspects, the direct linkage forms the first cleavable moiety in the reaction linking the polymer to the compound).

Exemplary compounds suitable for A are described herein. In one embodiment, A is a compound of the formula III. In one embodiment, A is a compound of the formula IV. In one embodiment, A is a compound of the formula IV where $R_{19}$ is $CH_3$.

In one embodiment, the first phenolic hydroxyl is modified by forming a bond with L. In one embodiment, the first phenolic hydroxyl is modified through the formation of a bond between L and the oxygen atom of the first phenolic hydroxyl group. In one embodiment, the second phenolic hydroxyl is modified by forming a bond with the blocking group. In one embodiment, the second phenolic hydroxyl is modified through the formation of a bond between the oxygen atom of the second phenolic hydroxyl group and the blocking group. In each of the forgoing embodiments, the modification of the first and/or second phenolic hydroxyl may result in the formation of an ester linkage, wherein the ester linkage comprises the oxygen atom of the first and/or second phenolic hydroxyl groups. In each of the forgoing embodiments, the modification of the first and/or second phenolic hydroxyl may result in the formation of an ester linkage, wherein the ester linkage comprises the oxygen atom of the first and/or second phenolic hydroxyl groups and the ester linkage forms the first and/or second cleavable moieties. Therefore, in certain embodiments, the first cleavable moiety is an ester linkage, the second cleavable moiety is an ester linkage, or both the first cleavable moiety and the second cleavable moiety are each ester linkages.

Exemplary R groups include, but are not limited to, hydrogen, alkyl and substituted alkyl. In one embodiment, R is an alkyl group, such as a C1 to C4 alkyl group. In a specific embodiment of the foregoing, the initiating group is a methyl group. In another embodiment, the initiating group is H. In yet another embodiment, the initiating group is selected to lack a functional group. Additional exemplary initiating groups are disclosed in U.S. Pat. Nos. 7,943,141, 8,088,884, 8,110,651 and 8,101,706, each of which is incorporated herein by reference for such teachings.

L may form a linkage with any reactive group on the polymer and a reactive group on the compound, suitably the first phenolic hydroxyl group on the catechol moiety of the compound. In one embodiment, L is a linkage between the compound and a terminal end of the polymer. In one embodiment, L is a linkage between the compound and a side chain group of the polymer (referred to herein as a "pendent" position or a "pendent"). Furthermore, L may include component(s) of a group that was originally present on the polymer and/or the compound.

Suitable parameters for L are described herein. In a particular embodiment, L is a linking group containing a first cleavable moiety.

In a particular embodiment, the polymer conjugates of the present disclosure may be represented by the general formula IIB, or a pharmaceutically acceptable salt thereof.

In one embodiment of the conjugates of formula IIA and IIB, T is a thioalkyl carboxylic acid, a thiocarboxylic ester, or a hydroxyl. In one embodiment of the conjugates of formula IIA and IIB, T is Z—B-Q, wherein Z is S, O, or N; B is an optional linking group; and Q is a terminating nucleophile or a portion of a terminating nucleophile. In certain embodiments of the conjugates of formula IIA and IIB, Q is non-reactive (i.e., does not contain a functional group); in other embodiments, Q contains a functional group.

Exemplary B groups include, but are not limited to, alkylene groups. In a particular embodiment, B is $-(CH_2)_{1-16}-$. In certain embodiments, B is $-(CH_2)_{1-10}-$, $-(CH_2)_{1-8}-$, $-(CH_2)_{1-6}-$, $-(CH_2)_{1-4}-$, or $-(CH_2)_2-$. In a particular embodiment, of the conjugates of formula IIA and IIB, Z is S. Polyoxazoline conjugates containing a sulfur group as described herein may be prepared by terminating the cation at the end of the poly oxazoline polymer with a mercaptide reagent, such as, but not limited to, a mercapto-ester (for example, $-S-CH_2CH_2-CO_2CH_3$ or $-S-CH_2CH_2-CO_2H$), an amine (for example, $-S-CH_2CH_2-NH_2$) or mercapto-protected amine (for example, $-S-CH_2CH_2-$NH-tBoc). Such POZ conjugates provide for effective, large-scale purification by ion-exchange chromatography (to remove secondary amines), as well as allowing for control of polydispersity values (with polydispersity values of 1.10 or less) and for the creating of conjugates with higher molecular weight POZ polymers. In another embodiment, of the conjugates of formula IIA and IIB, Z is N. In a further embodiment, of the conjugates of formula IIA and IIB, Z is O.

As stated above, Q may be non-reactive or may contain a functional group. When Q contains a functional group, exemplary functional groups include, but are not limited to, alkyne, alkene, amine, oxyamine, aldehyde, ketone, acetal, thiol, ketal, maleimide, ester, carboxylic acid, activated carboxylic acid (such as, but not limited to, N-hydroxysuccinimidyl (NHS) and 1-benzotriazine active ester), an active carbonate, a chloroformate, alcohol, azide, vinyl sulfone, or orthopyridyl disulfide (OPSS). When Q contains a functional group, the functional group may be chemically orthogonal to one or more or all other functional groups present on the conjugate. When Q is a non-reactive group, any non-reactive group may be used, including, but not limited to unsubstituted alkyl and $-C_6H_5$.

In one embodiment of the conjugates of formulas IIA-JIB, L is a linking group and contains the first cleavable moiety, Z is S, B is $-(CH_2)_y-$ and Q is —COOH. In another specific embodiment L is a linking group and contains the first cleavable moiety, Z is O, B is $-(CH_2)_y-$ and Q is —COOH. In still another specific embodiment L is a linking group and contains the first cleavable moiety, Z is N, B is $-(CH_2)_y-$ and Q is —COOH. In any of the foregoing embodiments, the first cleavable moiety may be an ester group. In any of the foregoing, y is 2.

In one embodiment of the conjugates of formulas IIA-JIB, L is a linking group and contains the first cleavable moiety, Z is S, B is $-(CH_2)_y-$ and Q is $-COOCH_3$. In another specific embodiment L is a linking group and contains the first cleavable moiety, Z is O, B is $-(CH_2)_y-$ and Q is $-COOCH_3$. In still another specific embodiment L is a linking group and contains the first cleavable moiety, Z is N, B is $-(CH_2)_y-$ and Q is $-COOCH_3$. In any of the foregoing embodiments, the first cleavable moiety may be an ester group. In any of the foregoing, y is 2.

In one embodiment of the conjugates of formulas IIA-JIB, L is a linking group and contains the first cleavable moiety, Z is S, B is $-(CH_2)_y-$ and Q is $-NH_2$. In another specific embodiment L is a linking group and contains the first cleavable moiety, Z is O, B is $-(CH_2)_y-$ and Q is $-NH_2$. In still another specific embodiment L is a linking group and contains the first cleavable moiety, Z is N, B is $-(CH_2)_y-$ and Q is $-NH_2$. In any of the foregoing embodiments, the first cleavable moiety may be an ester group. In any of the foregoing, y is 2.

In one embodiment of the conjugates of formulas IIA-IIB, L is a linking group and contains the first cleavable moiety, Z is S, B is $-(CH_2)_y-$ and Q is NH-tBoc. In another specific embodiment L is a linking group and contains the first cleavable moiety, Z is 0, B is $-(CH_2)_y-$ and Q is NH-tBoc. In still another specific embodiment L is a linking group and contains the first cleavable moiety, Z is N, B is $-(CH_2)_y-$ and Q is —NH-tBoc. In any of the foregoing embodiments, the first cleavable moiety may be an ester group. In any of the foregoing, y is 2.

In one embodiment of the conjugate of formulas IIA-IIB, $R_1$ is independently selected for each repeating unit from an unsubstituted or substituted alkyl, an unsubstituted or substituted alkenyl, an unsubstituted or substituted aralkyl or an unsubstituted or substituted heterocyclylalkyl group. In one embodiment, $R_1$ is an unsubstituted alkyl or a substituted alkyl, such as a $C_1$-$C_4$ unsubstituted alkyl or a substituted alkyl. In a particular embodiment, $R_1$ is methyl, ethyl, propyl or butyl. Exemplary $R_1$ groups are described in U.S. Pat. Nos. 7,943,141, 8,088,884, 8,110,651 and 8,101,706, each of which is incorporated herein by reference for such teachings.

In one embodiment of the conjugate of formula IIB, Y is -L-A. When Y is -L-A, the -L-A group on Y may be the same as the -L-A group on X. When Y is -L-A, the -L-A group on Y may be different from the -L-A group on X.

In one embodiment of the conjugate of formula IIB, Y is a pendent moiety. When Y is a pendent moiety, Y may be a non-reactive pendent moiety or a pendent moiety containing an active functional group. In one embodiment when Y is a pendent moiety, Y is independently selected for each repeating unit from an unsubstituted or substituted alkyl, an unsubstituted or substituted alkenyl, an unsubstituted or substituted aralkyl or an unsubstituted or substituted heterocyclylalkyl group. In one embodiment, Y is an alkyl or a substituted alkyl. In a particular embodiment, Y is methyl, ethyl, propyl or butyl. In a particular embodiment, Y is a pendent moiety comprising an active functional group. Suitable reactive functional groups include, but are not limited to, alkyne, amine, oxyamine, aldehyde, ketone, acetal, ketal, maleimide, ester, carboxylic acid, activated carboxylic acid (such as, but not limited to, N-hydroxysuccinimidyl (NHS) and 1-benzotriazineyl active ester), an active carbonate, a chloroformate, alcohol, azide, vinyl sulfone, and orthopyridyl disulfide (OPSS). In certain embodiments, the active functional group of Y is chemically orthogonal to one or more or all other functional group on the conjugate. In certain embodiments, the active functional group of Y is not chemically orthogonal to one or more or all other functional group on the conjugate. In one embodiment, Y is an unsubstituted or substituted alkyl, an unsubstituted or substituted alkenyl, an unsubstituted or substituted aralkyl or an unsubstituted or substituted heterocyclylalkyl group.

In one embodiment of the conjugates of the formulas II-IIB, L is a linking group and contains the first cleavable moiety. In one embodiment, the first cleavable moiety is an ester group. In one embodiment, the ester group incorporates the O atom of the first phenolic hydroxyl.

In one embodiment of the conjugate of the formula IIB, o1 is from 1 to less than or equal to 20, and o2 is 0. In one embodiment, o1 is from 1 to less than or equal to 20 and o2 is from 1 to 30. In one embodiment, o1 is from 1 to less than or equal to 20 and o2 is from 1 to 30 and at least a portion of Y is a pendent moiety comprising a functional group. In one embodiment, o1 is from 1 to less than or equal to 10 and o2 is from 1 to 30 and at least a portion of Y is -L-A, wherein the -L-A of X and Y are the same as one another. In one embodiment, o1 is from 1 to less than or equal to 10 and o2 is from 1 to 30 and at least a portion of Y is -L-A, wherein the -L-A of X and Y are different from one another.

In a particular embodiment of the conjugates of the formulas IIA-IIB, T is Z—B-Q In one embodiment of the conjugates of the formulas IIA-IIB, L is a linking group and contains the first cleavable moiety, Z is S, B is —$CH_2CH_2$— and Q is —COOH. In another specific embodiment L is a linking group and contains the first cleavable moiety, Z is 0, B is —$CH_2CH_2$— and Q is —COOH. In still another specific embodiment L is a linking group and contains the first cleavable moiety, Z is N, B is —$CH_2CH_2$— and Q is —COOH. In any of the foregoing embodiments, the first cleavable moiety may be an ester group.

In the foregoing embodiments where the polymer is a polyoxazoline polymer, a variety of polyoxazoline polymers may be used in the conjugates of the present disclosure. The polyoxazoline polymer may contain a single type or class of functional groups or may contain more than one type or class of functional groups. The polyoxazoline polymer be a linear polyoxazoline polymer, a branched polyoxazoline polymer, or a multi-armed polyoxazoline polymer, wherein any of the foregoing may contain pendent groups. Various representative polyoxazoline polymers are described herein. The POZ polymer may be prepared by living cation polymerization or by other methods as is known in the art. Representative POZ polymers are described in U.S. Pat. Nos. 7,943,141, 8,088,884, 8,110,651 and 8,101,706, each of which is incorporated herein by reference for such teachings. In one embodiment, the POZ polymer is prepared by living cation polymerization.

In the foregoing embodiments where the polymer is a polyoxazoline polymer, n is from 1-500. In one embodiment, n is from 1-250. In one embodiment, n is from 1-100. In one embodiment, n is from 1 to 50. In one embodiment, n is greater than 25 and less than 250. In one embodiment, n is greater than 25 and less than 150.

In the foregoing embodiments where the polymer is a polyoxazoline polymer, the polyoxazoline polymer portion (excluding A and L) has a molecular weight between 2 kDa and 100 kDa. In one embodiment, the polyoxazoline polymer portion (excluding A and L) has a molecular weight between 10 kDa and 30 kDa. In one embodiment, the polyoxazoline polymer portion (excluding A and L) has a molecular weight between 15 kDa and 25 kDa. In one embodiment, the polyoxazoline polymer portion (excluding A and L) has a molecular weight of 20 kDa. In the current specification, when a molecular weight is provided for a polymer, particularly a polyoxazoline polymer, unless specifically stated otherwise the molecular weight is a number average molecular weight.

In the foregoing embodiments of the conjugates of formula I, II and IIA, b is from 1-40. In one embodiment, b is from 1-30. In one embodiment, b is from 1-20. In one embodiment, b is from 1 to 15. In one embodiment, b is from 1 to 10. In one embodiment, b is greater than or equal to 5 and less than or equal to 15. In one embodiment, b is 10.

In any the foregoing embodiments of the conjugates of formula I and II-IIB, L may form a linkage with any reactive group on the polymer and any reactive group on the compound (preferably the first phenolic hydroxyl). In any the foregoing embodiments, L is a linkage between the compound and a terminal end of the polymer. In any the foregoing embodiments, L is a linkage between the compound and a side chain group of the polymer (referred to herein as a "pendent" position or a "pendent"). In any the foregoing embodiments, L may include components of a group that was originally present on the polymer and/or the compound. Suitable parameters for L are described herein. In any the foregoing embodiments, L is a linking group containing a first cleavable moiety.

In any of the foregoing embodiments of the conjugates of formula I and II-IIB, regardless of the form of the linkage (whether direct or via a linking group), the linkage is a cleavable linkage that allows the compound to be released from the polymer after administration of the conjugate to a subject via cleavage of the first cleavable moiety. The cleavage of the first cleavable moiety (release kinetics) of the compound from the conjugate (which are controlled, at least in part, by the structure of the blocking group on the second phenolic hydroxyl) provides delivery of the compound that can be controlled. In any of the foregoing embodiments, the cleavage of the first cleavable moiety results in the generation of the free phenolic hydroxyl group at the first phenolic hydroxyl.

In any of the foregoing embodiments of the conjugates of formula I and II-TTB, the cleavage of the first cleavable moiety (release kinetics) of the compound from the polymer is controlled, at least in part, by the structure of the blocking group on the second phenolic hydroxyl. In any of the foregoing embodiments, the cleavage of the first cleavable moiety (release kinetics) of the compound from the polymer is controlled, at least in part, by the structure of the linking group and the structure of the blocking group on the second phenolic hydroxyl. In any of the foregoing embodiments, the blocking group comprises a second cleavable moiety, which may be the same or different as the first cleavable moiety. In any of the foregoing embodiments, the first and second cleavable moieties are the same. In any of the foregoing embodiments, the first and second cleavable moieties are different. In any of the foregoing embodiments, at least one of the first and second cleavable moieties is an ester linkages. In any of the foregoing embodiments, both of the first and second cleavable moieties are ester linkages.

In any of the foregoing embodiments of the conjugates of formula I and II-IIB, the conjugates provide for the delivery of a therapeutically effective amount of the compound to the subject over a period of time from: 12 hours to 24 hours; 24 hours to 48 hours; 24 hours to 72 hours; 24 hours to 96 hours; 24 hours to 120 hours; 24 hours to 144 hours; or 24 hours to 168 hours. In any of the foregoing embodiments, the delivery is a controllable delivery or a sustained controllable delivery. In any of the foregoing embodiments, the compound is delivered with a pharmacokinetic/release profile that lacks peaks and troughs.

In any of the foregoing embodiments of the conjugates of formula I and II-IIB, the conjugates provide for the delivery of a therapeutically effective amount of the compound to the subject over a period of one week or more. In any of the foregoing embodiments, the conjugates provide for the delivery of a therapeutically effective amount of the compound to the subject over a period of time from: one to two weeks; one to three weeks; or one to four weeks. In any of the foregoing embodiments, the delivery is a controllable delivery or a sustained controllable delivery. In any of the foregoing embodiments, the compound is delivered with a pharmacokinetic/release profile that lacks peaks and troughs.

In the embodiments described above for the conjugates of formula I and II-IIB, specific linking groups are as described below. For the sake of clarity any linking group described herein may be used in the general formulas described above.

L

In the embodiments described above, L is a linking group that forms or contains a first cleavable moiety or a direct linkage that forms or contains a first cleavable moiety. In those embodiments where L forms a first cleavable moiety, the interaction of L with a group on the polymer or the compound forms the first cleavable moiety. In certain preferred embodiments, the reaction between L and the oxygen atom on the first phenolic hydroxyl forms the first cleavable moiety. As such, L is a cleavable linkage between the compound and the polymer. In other words, the first cleavable moiety can be cleaved in-vivo in a subject after administration of a polymer conjugate of the present disclosure to the subject. In one embodiment, the cleavable moiety is cleaved by a chemical reaction. In one aspect of this embodiment, the cleavage is by hydrolysis of an ester group or reduction, such as, but not limited to, reduction of a disulfide. In one embodiment, the cleavable moiety is cleaved by a substance that is naturally present or induced to be present in the subject. In one aspect of this embodiment, such a substance is an enzyme or polypeptide. Therefore, in one embodiment, the cleavable moiety is cleaved by an enzymatic reaction. In one embodiment, the cleavable moiety is cleaved by a combination of the foregoing. L may contain portions of the polymer and/or portions of the compound as such portions have reacted to form the linking group or direct linkage to the polymer and/or compound as discussed herein.

Exemplary first cleavable moieties include, but are not limited to, an ester linkage, a carboxylate ester linkage (—C(O)—O—), a carbonate ester linkage (—O—C(O)—O—), a carbamate linkage (—O—C(O)—NH—), am amide linkage (—C(O)—NH—), and a disulfide linkage (S—S); other cleavable moieties are discussed herein. In a particular embodiment, the first cleavable moiety is an ester linkage. In another particular embodiment, the cleavable moiety is a carboxylate ester linkage. In the descriptions below, the polymer is assumed to be a polyoxazoline polymer for the purpose of exemplification. However, the reactions below are equally applicable to other polymer types.

In one embodiment, the linking group is a di-substituted triazole that contains a first cleavable moiety in one of the $R_3$ or $R_4$ groups. In one embodiment, the first cleavable moiety is present in the $R_4$ group. In a specific embodiment, the di-substituted triazole has the structure:

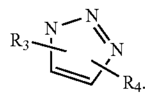

In another embodiment, the di-substituted triazole has the structure:

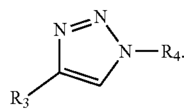

In each of the foregoing structures:

$R_3$ is a linker linking the triazole moiety to the polymer chain. $R_3$ may be defined in part by the functional group on the polymer chain; in other words, $R_3$ may contain a part of the functional group on the polymer chain. In one embodiment, $R_3$ is —C(O)—$R_5$—, where $R_5$ is absent or is an unsubstituted or substituted alkyl, an unsubstituted or substituted alkenyl, an unsubstituted or substituted aralkyl or an unsubstituted or substituted heterocyclylalkyl group. In one embodiment, $R_5$ is absent or is a substituted or unsubstituted alkyl from 1 to 10 carbons in length. In one embodiment, $R_5$ is absent or is an unsubstituted straight chain alkyl from 1 to 10 carbons in length.

$R_4$ is a linker linking the triazole moiety to the compound, where the linkage between $R_4$ and the compound occurs between the first phenolic hydroxyl on the catechol moiety of the compound. $R_4$ may be defined in part by the functional group on the compound; in other words, $R_4$ may contain a part of the group/functional group on the compound, such as the O atom of the first phenolic hydroxyl group. In one embodiment, $R_4$ is —$R_6$—$R_7$—$R_8$—, where $R_6$ is a substituted or unsubstituted alkyl, substituted or unsubstituted aralkyl or a oligo(ethylene oxide) (for example, —$(CH_2CH_2O)_e$— where e is 1-10 or 1-4), $R_7$ is a group containing the first cleavable moiety or a portion of the first cleavable moiety and $R_8$ is absent or O. In certain embodiments, $R_7$ and $R_8$ may combine to form the first cleavable moiety. In certain embodiments, $R_7$ forms the first cleavable moiety. In one embodiment, $R_7$ is —$R_a$—C(O)—$R_b$—, —$R_a$—O—C(O)—$R_b$—, —$R_a$—C(O)—O—$R_b$, —$R_a$—C(O)—NH-cyclic-O—C(O)—$R_b$— (where cyclic represents substituted or unsubstituted aryl, heterocylalkyl, heteroaryl, heterocyclyl or cycloalkyl), —$R_a$—C(O)—NH—$(C_6H_4)$—O—C(O)—$R_b$—, —$R_a$—O—C(O)—$NR_{10}$—$R_b$—, —$R_a$—CH(OH)—O—$R_b$—, $R_a$—S—S—$R_b$—, $R_a$—O—P(O)$(OR_{10})$—O—$R_b$—, or —$R_a$—C(O)—$NR_{10}$—$R_b$—, where $R_{10}$ is a is H or a substituted or unsubstituted C1-C5 alkyl) and $R_a$ and $R_b$ are each independently absent or substituted or unsubstituted alkyl. In another embodiment, $R_a$ and $R_b$ are each independently absent or a C1-C16 substituted or unsubstituted alkyl.

In one embodiment of the foregoing, $R_6$ is a straight chain substituted or unsubstituted C1-C10 alkyl or a branched substituted or unsubstituted C1-C10 alkyl, $R_7$ is —$R_a$—C(O)—$R_b$— and $R_8$ is —O—. In one embodiment of the foregoing, $R_6$ is a straight chain substituted or unsubstituted C1-C10 alkyl or a branched substituted or unsubstituted C1-C10 alkyl, $R_7$ is —$R_a$—C(O)—O—$R_b$— and $R_8$ is absent.

In one embodiment of the foregoing, $R_6$ is a straight chain substituted or unsubstituted C1-C4 alkyl or a branched substituted or unsubstituted C1-C4 alkyl, $R_7$ is —$R_a$—C(O)—$R_b$— and $R_8$ is —O—. In one embodiment of the foregoing, $R_6$ is a straight chain substituted or unsubstituted C1-C4 alkyl or a branched substituted or unsubstituted C1-C4 alkyl, $R_7$ is —$R_a$—C(O)—O—$R_b$— and $R_8$ is absent.

In a particular embodiment, $R_3$ is —C(O)—$(CH_2)_3$ and $R_4$ is —$(CH_2)_d$—C(O)—O—, —$CH_2$—C(O)—O—, —$CH_2$—$CH_2$—C(O)—O—, —$CH_2$—$CH_2$—$CH_2$—C(O)—O—, or —$CH_2(CH_3)$—C(O)—O—, wherein d is an integer from 1 to 10.

In a particular embodiment, $R_3$ is —C(O)—$(CH_2)_3$ and $R_4$ is —$(CH_2)_d$—C(O)—, —$CH_2$—C(O)—, —$CH_2$—$CH_2$—C(O)—, —$CH_2$—$CH_2$—$CH_2$—C(O)—, or —$CH_2(CH_3)$—C(O)—, wherein d is an integer from 1 to 10.

In each of the foregoing, the first cleavable moiety may be cleaved chemically under physiological conditions in-vivo in the subject, cleaved by a substance that is naturally present or induced to be present in the subject under physiological conditions in-vivo in the subject or by a combination of the foregoing. In one embodiment, such substance is an enzyme or polypeptide and the cleavage is an enzymatic cleavage.

Compound Comprising a Catechol Moiety

In the embodiments described above for the general formulas I, II, IIA, and IIB, specific compounds (A) are as described below. For the sake of clarity any compound (A) described herein may be used in the general formulas described above.

The compound comprising a catechol moiety may be any compound known in the art that is useful in the diagnosis or treatment of a disease or condition. Compounds comprising a catechol moiety have been reported to have a wide range of activities, including, but not limited to, adrenergic agonists, antiviral, anti-inflammatory, emetic, cardiotonic, antiasthmatic, enzyme inhibition, antibiotic, antineoplastic, anticholinergic, antispasmodic, bronchodilator, antihypertensive, dopamine receptor agonist, antioxidant, spermaticide, and insecticide activity. The compound comprising a catechol moiety may be a diagnostic agent or a therapeutic agent.

In one embodiment, the compound comprising a catechol moiety is represented by the formula III, or a pharmaceutically acceptable salt thereof:

III

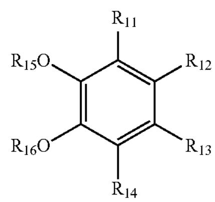

wherein $R_{11}$, $R_{12}$, $R_{13}$ and $R_{14}$ are independently selected from H, OH, halogen, alkoxy, $NO_2$, unsubstituted alkyl, heteroalkyl, alkenyl, or alkynyl, substituted alkyl, heteroalkyl, alkenyl, or alkynyl, aryl, substituted aryl, cycloalkyl, substituted cycloalkyl, heterocyclyl, substituted heterocyclyl, heteroaryl, substituted heteroaryl, heterocyclylalkyl, substituted heterocyclylalkyl, heteroarylalkyl, substituted heteroarylalkyl, or any two of $R_{11}$, $R_{12}$, $R_{13}$ and $R_{14}$ that are adjacent to one another, taken together with the carbons to which they are attached, may form an optionally substituted aryl, heteroaryl, heterocyclyl ring; one of $R_{15}$ or $R_{16}$ is L; and the other of $R_{15}$ or $R_{16}$ is a blocking group.

In certain embodiments, a "substituted alkyl" or "substituted heteroalkyl" refers to a $C_1$-$C_{14}$ straight- or branched-chain alkyl or heteroalkyl group that is substituted with up to 5 groups selected from the group consisting of —OH, —$NH_2$, —NH—$NH_2$, =O(OH), substituted aryl, and =O.

As discussed herein, in one embodiment, the first phenolic hydroxyl (represented by $R_{15}$ or $R_{16}$) is modified by forming a linkage with L. In one embodiment, the oxygen atom of the first phenolic hydroxyl participates in formation of the linkage with L. Formation of the linkage may comprise the formation of a chemical bond between the first phenolic hydroxyl (for example, the oxygen atom) and an atom or group on the polymer or the linking group. In one embodiment, the second phenolic hydroxyl (represented the other of $R_{15}$ or $R_{16}$) is modified by forming a bond with the blocking group. In one embodiment, the oxygen atom of the second phenolic hydroxyl participates in formation of a bond with the blocking group. Formation of the chemical bond may be between the first phenolic hydroxyl (for example, the oxygen atom) and an atom or group on the blocking group. In each of the forgoing embodiments, the modification of the first and/or second phenolic hydroxyl may results in the formation of an ester linkage, wherein the ester linkage comprises the oxygen atom of the first and/or second phenolic hydroxyl groups. In each of the forgoing embodiments, the modification of the first and/or second phenolic hydroxyl may result in the formation of an ester linkage, wherein the ester linkage comprises the oxygen atom of the first and/or second phenolic hydroxyl groups and the ester linkage forms the first and/or second cleavable moieties. Therefore, in certain embodiments, the first and the second cleavable moieties are the same. Therefore, in certain embodiments, the first cleavable moiety is an ester linkage, the second cleavable moiety is an ester linkage, or both the first cleavable moiety and the second cleavable moiety are each ester linkages.

In one embodiment, the blocking group contains a second cleavable moiety or forms a second cleavable moiety when forming a bond with (i.e., modifying) the second phenolic hydroxyl. In one embodiment, the blocking group forms the second cleavable moiety when forming a bond with the second phenolic hydroxyl. In one embodiment, the cleavable moiety is cleaved by a chemical reaction. In one aspect of this embodiment, the cleavage is by hydrolysis of an ester group or reduction, such as, but not limited to, reduction of a disulfide. In one embodiment, the cleavable moiety is cleaved by a substance that is naturally present or induced to be present in the subject. In one aspect of this embodiment, such a substance is an enzyme or polypeptide. Therefore, in one embodiment, the cleavable moiety is cleaved by an enzymatic reaction. In one embodiment, the cleavable moiety is cleaved by a combination of the foregoing.

Exemplary second cleavable moieties include, but are not limited to, an ester linkage, a carboxylate ester linkage (—C(O)—O—), a carbonate ester linkage (—O—C(O)—O—), a carbamate linkage (—O—C(O)—NH—), am amide linkage (—C(O)—NH—), and a disulfide linkage (S—S); other cleavable moieties are discussed herein. In a particular embodiment, the first cleavable moiety is an ester linkage. In another particular embodiment, the cleavable moiety is a carboxylate ester linkage.

In one embodiment, the blocking group is —$R_{17}$—$R_{18}$, where $R_{17}$ is —C(O)—, —C(O)—O—, —C(O)—NH-cyclic-O—C(O)— (where cyclic represents substituted or unsubstituted aryl, heterocylalkyl, heteroaryl, heterocyclyl or cycloalkyl), —C(O)—NH—($C6H_4$)—O—C(O)—, $CH_3(CH_2)_{1-4}$—O—C(O)—$(CH_2)_{1-4}$—C(O)— or —O—P(O)$(OR_9)$(O)— (where $R_9$ is H or a substituted or unsubstituted C1-C5 alkyl) and $R_{18}$ is an unsubstituted or substituted alkyl, an unsubstituted or substituted alkenyl, an unsubstituted or substituted aralkyl or an unsubstituted or substituted aryl group.

In one embodiment, $R_{17}$ forms a bond with the oxygen atom of the second phenolic hydroxyl group and $R_{17}$ and the O to which it is linked forms the second cleavable moiety. In one embodiment, the second cleavable moiety is —C(O)—O.

In one embodiment, $R_{18}$ is a substituted or unsubstituted alkyl. In one embodiment, $R_{18}$ is a substituted or unsubstituted C1-C6 alkyl. In one embodiment, $R_{18}$ is a substituted or unsubstituted C1-C6 straight chain alkyl. In one embodiment, $R_{18}$ is a substituted or unsubstituted C1-C6 branched chain alkyl. In one embodiment, $R_{18}$ is a substituted or unsubstituted aralkyl. In one embodiment, $R_{18}$ is a substituted or unsubstituted aryl.

In one embodiment, the blocking group has the structure $(CH_3)_y$—$(CH_x)$—$(CH_2)_{0-6}$—C(O)—O-compound, wherein when y is 1, x is 2, when y is 2, x is 1, or when y is 3, x is 0. In one embodiment, the blocking group has the structure $(CH_3)_y$—$(CH_x)$—C(O)—<u>O</u>-compound, wherein when y is 1, x is 2, when y is 2, x is 1, or when y is 3, x is 0. In one embodiment, the blocking group has the structure $CH_3$—$(CH_2)_{0-6}$—C(O)—<u>O</u>-compound. In one embodiment, the blocking group has the structure $CH_3$—$(CH_2)_{0-6}$—C(O)—$(CH_2)_{0-6}$—<u>O</u>-compound. In the foregoing, the underlined portion represents a portion of the compound comprising a catechol moiety and is not considered a part of the blocking group.

In one embodiment, the blocking group has the structure $CH_3$—C(O)—<u>O</u>-compound. In one embodiment, the blocking group has the structure $CH_3$—$(CH_2)_2$—C(O)—<u>O</u>-compound. In one embodiment, the blocking group has the structure $CH_3$—$CH_2$—C(O)—<u>O</u>-compound. In one embodiment, the blocking group has the structure $(CH_3)_2$—CH—C(O)—<u>O</u>-compound. In one embodiment, the blocking group has the structure $(CH_3)_3$—C—C(O)—<u>O</u>-compound. In one embodiment, the blocking group has the structure $CH_3CH_2$—O—C(O)—$CH_2CH_2$—C(O)—<u>O</u>-compound. In one embodiment, the blocking group has the structure

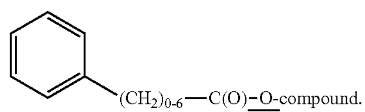

In one embodiment, the blocking group has the structure

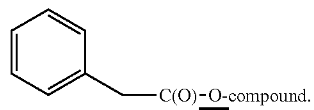

In the foregoing, the underlined portion represents a portion of the compound comprising a catechol moiety and is not considered a part of the blocking group.

Therefore, in certain embodiments, the present disclosure provides for conjugates of the formula I, II, IIA, and IIB comprising a water-soluble-polymer and a compound of the formula III. In certain preferred aspects, the water-soluble polymer is a polyoxazoline polymer. Such conjugates are useful in treating a disease or condition as described herein, including, but not limited to, a dopamine-responsive disorder, such as, but not limited to, Parkinson's disease.

In one embodiment, the compound is a compound described in Yang et al. (Molecules, 2007, 12, 878-884, including in particular, FIG. 1 and Table Si). In one embodiment, the compound is apomorphine, dopamine, norepinephrine, levodopa, levonordefrin, isoproterenol, epinephrine, nordefrin, (r)-(+)-fenoldopam, fenoldopam, isoetharine, carbidopa, dobutamine, tolcapone, and entacapone. In one embodiment, the compound is a compound described in Yang et al. (including in particular, FIG. 1 and Table Si) that is useful in treating a dopamine responsive condition, such as, but not limited to, Parkinson's disease. In one embodiment, the compound is apomorphine, arbutamine, carbidopa, dobutamine, dopamine, entacapone, epinephrine, fenoldopam, isoetharine, isoproterenol, levopoda, levonordefrin, masaprocol, methyldopa, methyldopate, norepinephrine, protokylol, tolcapone, or (r)-(+)-fenoldopam. In another embodiment, the compound is apomorphine, fenoldopam, entacapone, tolcapone, chf-1303, dopamantine, dopamine, droxipoda, etilevodopa, exifone, or levodopa. In another embodiment, the compound is apomorphine, fenoldopam, entacapone, tolcapone, or levodopa. In the foregoing list of exemplary compounds, it is understood that the first phenolic hydroxyl of the catechol moiety is modified by one of $R_{18}$ or $R_{16}$, and the second phenolic hydroxyl of the catechol moiety is modified by the other of $R_{15}$ and $R_{16}$. As an example, consider the compound entacapone having the structure below:

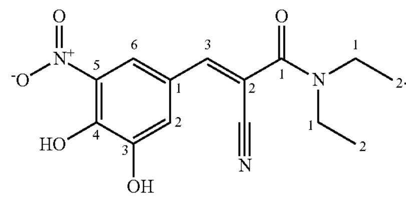

When entacapone is a compound (A) as described herein, the conjugate is understood to include both:

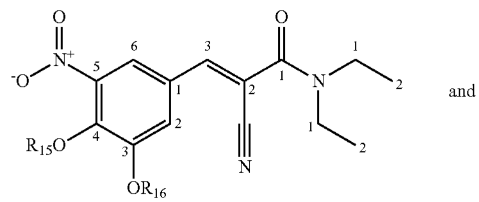

and

-continued

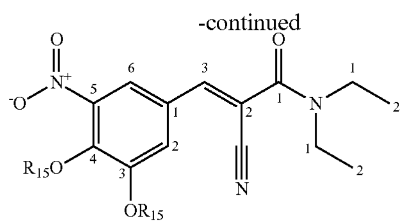

unless a particular form of entacapone is isolated prior to reaction with the polymer portion of the conjugate.

In certain embodiments, the compound is used to treat a dopamine-responsive disorder. Representative dopamine-responsive disorders are described herein and include, but are not Parkinson's disease. Parkinson's disease is a central nervous system disorder resulting from loss of dopamine neurons in the substantia nigra pars *compacta*. The loss of these neurons in the brain leads to a deficiency of dopamine, a neurotransmitter that is essential for normal coordination and movement. Striatal dopaminergic neurons fire in a random, but continuous fashion due to stable levels of dopamine, allowing for precisely coordinated movements. In Parkinson's disease patients, the pre-synaptic neurons degenerate. Administration of dopaminergic agents (for example, dopamine agonists) in an attempt to control symptoms leads to discontinuous stimulation of the post-synaptic neurons (caused for example by pulsatile stimulation of striatal dopamine receptors), promoting motor fluctuations that can worsen as the disease progresses (dyskinesia). Early symptoms of dopamine deficiency in Parkinson's disease include tremors, rigidity, bradykinesia, and gait problems. Cognitive and behavioral problems as well as dementia occur in later stages of Parkinson's disease.

While there is no cure for Parkinson's disease at this time, symptoms of this disease are treated with a variety of drugs aimed at maintaining dopaminergic tone. Drugs currently used for the treatment of Parkinson's disease include levodopa, dopamine agonists, adenosine $A_{2A}$ antagonist, anticholinergics, monoamine oxidase-B inhibitors and catechol-O-methyl transferase inhibitors and other drugs. There are challenges associated with these drugs, including limited bioavailability, short half-lives in-vivo and high rates of first pass and/or peripheral metabolism. The short half-lives of these drugs require frequent dosing of several times daily which results in pulsatile stimulation of striatal dopamine receptors, which may actually accelerate the demise of dopaminergic neurons in the CNS.

Apomorphine is a compound comprising a catechol group. Apomorphine's R-enantiomer is an agonist of both $D_1$ and $D_2$ dopamine receptors, with higher activity against $D_2$. The members of the $D_2$ subfamily, consisting of $D_2$, $D_3$, and $D_4$ receptors, are inhibitory G protein-coupled receptors. The $D_4$ receptor in particular is an important target in the signaling pathway, and is implicated in the pathogenesis of several neurological disorders. Apomorphine improves motor function by activating dopamine receptors in the nigrostriatal pathway, the limbic system, the hypothalamus, and the pituitary gland. It also increases blood flow to the supplementary motor area and to the dorsolateral prefrontal cortex (stimulation of which has been found to reduce the tardive dyskinesia effects of L-DOPA). Subjects with Parkinson's disease have also been found to have excess iron at sites of neurodegeneration; both the R- and S-enantiomers of apomorphine are potent iron chelators and radical scavengers. Apomorphine also reduces the breakdown of dopamine in the brain as well as inhibiting its synthesis.

Apomorphine is typically delivered to patient via subcutaneous injection. A common side effect of administering apomorphine by subcutaneous injection is the development of subcutaneous nodules at the injection site and a burning sensation at the site of injection. As apomorphine is delivered at least one time per day and different injection sites, patients often develop subcutaneous nodule in multiple places on the body. These subcutaneous nodule may develop into open wounds or sores which can become infected requiring further treatment. Surgery ray also be required in certain cases. As a result, patients are frequently in need of additional treatment to treat the side effects of apomorphine administration. The presence of the subcutaneous nodules is painful, limits available infusion sites and interfere with absorption of the drug over time. Through the use of the conjugates of the present invention, the side effects of apomorphine administration, including, but not limited to, the development of subcutaneous nodules, is eliminated or reduced.

In certain embodiments the compound is represented by the formula IV, or a pharmaceutically acceptable salt thereof:

IV

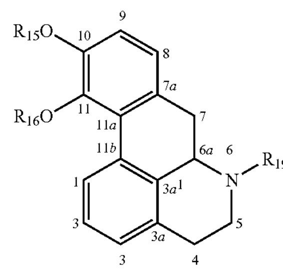

wherein $R_{15}$ and $R_{16}$ are as described for the compound of formula III; and $R_{19}$ is H, unsubstituted alkyl, alkenyl, or alkynyl, substituted alkyl, alkenyl, or alkynyl, benzyl, substituted benzyl, cycloalkyl, substituted cycloalkyl, aryl, substituted aryl, acyl, tetrahydrofuranyl, tetrahydropyranyl, nicotinyl or a 1-aryltetrazolyl. In one embodiment, $R_{19}$ is straight chain substituted or unsubstituted alkyl group of 1 to 5 carbons in length. In one embodiment, $R_{19}$ is selected from the group consisting of —H, $—CH_3$, $—CH_2—CH_3$, $—CH_2—CH_2—CH_3$, $—CH(CH_3)_2—CH_2—CH_2—CH_2—CH_3$, and

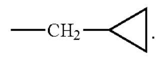

In one embodiment, $R_{19}$ is $CH_3$. When $R_{19}$ is $CH_3$, and $R_{15}$ and $R_{16}$ are both H, the compound is apomorphine (sold under the brand names Apokyn, Ixense, Spontane, and Uprima).

Therefore, in certain embodiments, the present disclosure provides for conjugates of the formula I, II, IIA, and IIB comprising a water-soluble-polymer and a compound of the formula IV. In certain preferred aspects, the water-soluble polymer is a polyoxazoline polymer. Such conjugates are useful in treating a dopamine-responsive disorder, such as, but not limited to, Parkinson's disease. In certain embodiments, the present disclosure provides for conjugates of the formula I, II, IIA, or IIB comprising a water-soluble-polymer and a compound of the formula IV, wherein $R_{19}$ is $CH_3$. In certain preferred aspects, the water-soluble polymer is a polyoxazoline polymer. Such conjugates are useful in treating a disease or condition as described herein, including, but not limited to, a dopamine-responsive disorder, such as, but not limited to, Parkinson's disease.

Representative Polymer Conjugates

The following are representative polymer conjugates according to the present disclosure.

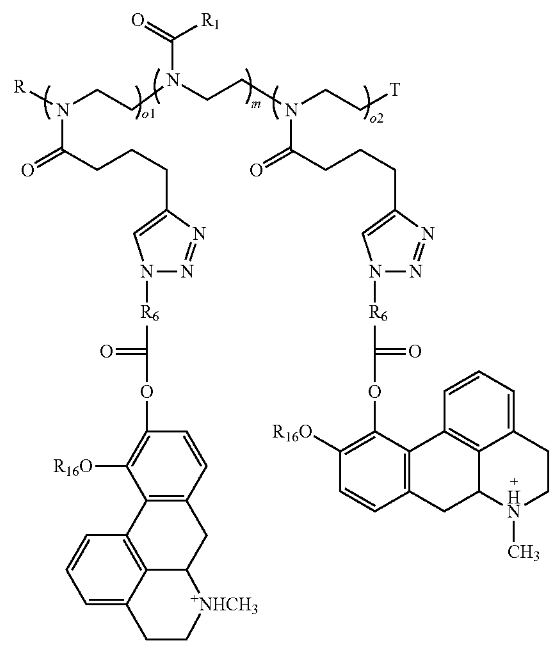

,

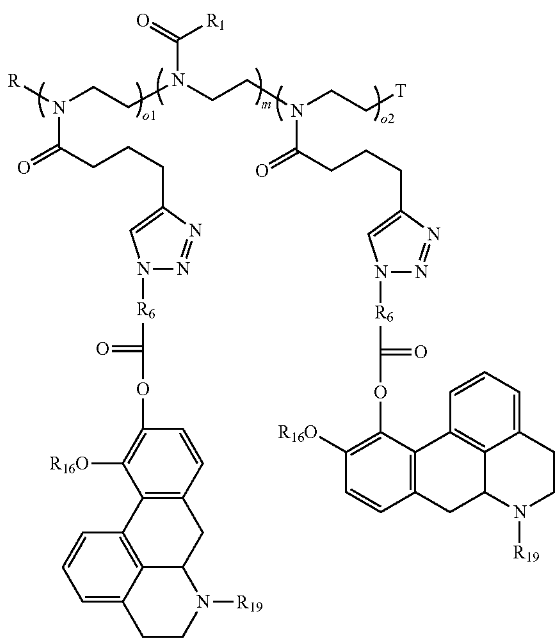

,

-continued

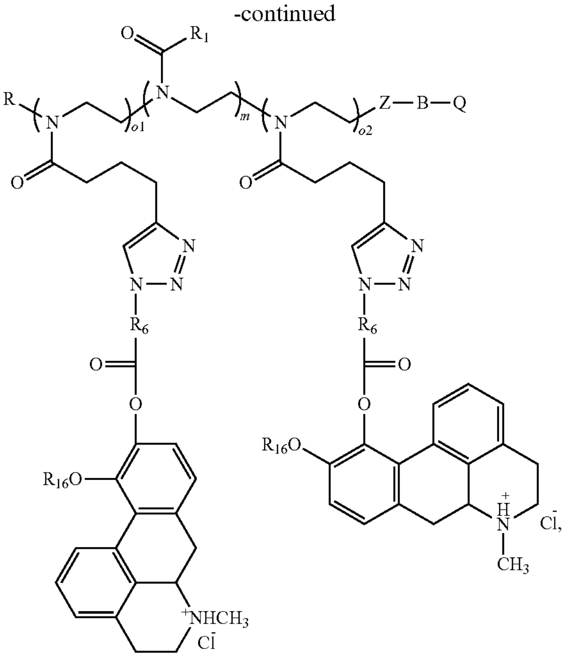

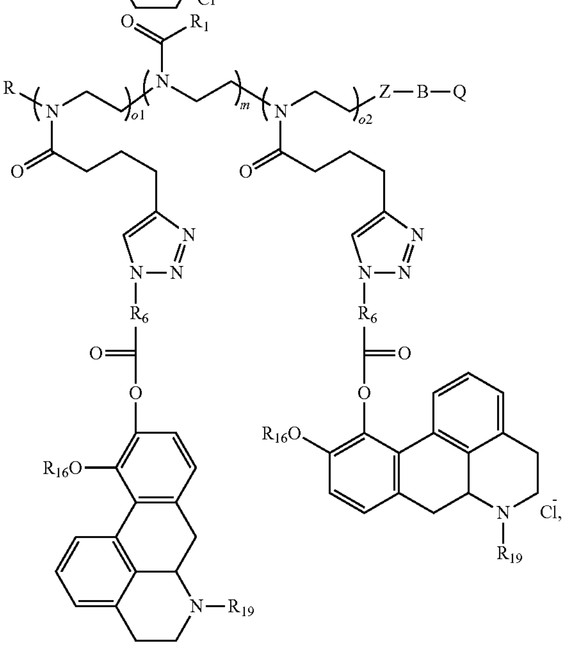

and the conjugates of the examples. In any of the foregoing, o2 may be 0 and the polymer subunits of o1 may contain a mixture of the enantiomeric forms of the compound.

In the foregoing embodiments, any of the groups for R, $R_1$, $R_6$, $R_{16}$, and $R_{19}$ may be used. In certain preferred embodiments, the variables are selected as set forth below.

R is selected from the group consisting of hydrogen, unsubstituted and substituted alkyl, C1 to C4 unsubstituted alkyl, and H.

$R_1$ for each repeating unit is selected from the group consisting of unsubstituted or substituted alkyl, unsubstituted or substituted alkenyl, unsubstituted or substituted aralkyl, unsubstituted or substituted heterocyclylalkyl group, unsubstituted C1 to C4 alkyl, and substituted C1 to C4. $R_6$ is selected from the group consisting of substituted or unsubstituted alkyl, straight chain substituted or unsubstituted C1-C4 alkyl, a branched substituted or unsubstituted C1-C4 alkyl, $-(CH_2)_d-$, $-CH_2-$, $-CH_2-CH_2-$, $-CH_2-CH_2-CH_2-$, and $-CH_2(CH_3)-$, wherein d is an integer from 1 to 10.

T is a thioalkyl carboxylic acid, a thiocarboxylic ester, or a hydroxyl.

Z is S, O, or N.

B is an optional linking group.

Q is a terminating nucleophile or a terminating portion of a nucleophile.

Certain preferred combinations of Z, B and Q are: Z is S, B is $-(CH_2)_y-$ and Q is —NH-tBoc, —COOH, $-COOCH_3$, or $-NH_2$, wherein y is 1 to 4.

In certain embodiments, $R_{16}$ is selected from the group consisting of $CH_3)_y-(CH_x)-(CH_2)_{0-6}-C(O)-$, wherein when y is 1, x is 2, when y is 2, x is 1, or when y is 3, x is 0. In one embodiment, the blocking group has the structure $(CH_3)_y-(CH_x)-C(O)-$, wherein when y is 1, x is 2, when y is 2, x is 1, or when y is 3, x is 0. In one embodiment, the blocking group has the structure $CH_3-(CH_2)_{0-6}-C(O)-$. In one embodiment, the blocking group has the structure $CH_3-(CH_2)_{0-6}-C(O)-(CH_2)_{0-6}-$. In certain embodiments, $R_{16}$ is selected from the group consisting of $(CH_3)-C(O)-$, $CH_3-(CH_2)_2-C(O)-$, $CH_3-CH_2-C(O)-$, $(CH_3)_2-CH-C(O)-$, $(CH_3)_3-C-C(O)-$, $CH_3CH_2-O-C(O)-CH_2CH_2-C(O)-$ and

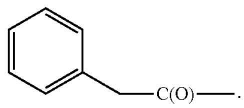

$R_{19}$ is selected from the group consisting of —H, $-CH_3$, $-CH_2-CH_3$, $-CH_2-CH_2-CH_3$, $-CH(CH_3)_2-CH_2-CH_2-CH_2-CH_3$, and

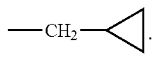

In certain embodiments, R is C1 to C4 unsubstituted alkyl or H, $R_1$ is unsubstituted C1 to C4 alkyl, $R_6$ is $(CH_2)_d-$, $-CH_2-$, $-CH_2-CH_2-$, $-CH_2-CH_2-CH_2-$, or $-CH_2(CH_3)-$, wherein d is an integer from 1 to 10, Z is S, B is $-(CH_2)_2-$ and Q is —NH-tBoc, —COOH, $-COOCH_3$, or $-NH_2$, $R_{16}$ is $(CH_3)-C(O)-$, $CH_3-(CH_2)_2-C(O)-$, $CH_3-CH_2-C(O)-$, $(CH_3)_2-CH-C(O)-$, $CH_3CH_2-O-C(O)-CH_2CH_2-C(O)-$, and

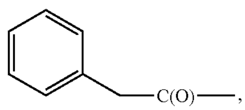

and $R_{19}$ is —H, $-CH_3$, $-CH_2-CH_3$.

Additional Compounds

The present disclosure also provides for various compounds that are useful in the preparation of the polymer conjugates described (i.e., intermediates). Such compounds may also be used as active agents on their own (i.e., without being linked to a water-soluble polymer as a component of a polymer conjugate).

In one embodiment, the present disclosure provides an intermediate of the formula V, or a pharmaceutically acceptable salt thereof:

V

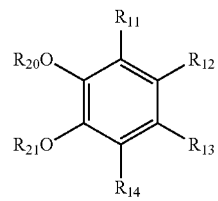

wherein $R_{11}$, $R_{12}$, $R_{13}$ and $R_{14}$ are independently selected from H, OH, halogen, alkoxy, $NO_2$, unsubstituted alkyl, heteroalkyl, alkenyl, or alkynyl, substituted alkyl, heteroalkyl, alkenyl, or alkynyl, aryl, substituted aryl, cycloalkyl, substituted cycloalkyl, heterocyclyl, substituted heterocyclyl, heteroaryl, substituted heteroaryl, heterocyclylalkyl, substituted heterocyclylalkyl, heteroarylalkyl, substituted heteroarylalkyl, or any two of Rn, $R_{12}$, $R_{13}$ and $R_{14}$ that are adjacent to one another, taken together with the carbons to which they are attached, may form an optionally substituted aryl, heteroaryl, heterocyclyl ring; and one of $R_{20}$ and $R_{21}$ is H or a blocking group and the other of $R_{20}$ and $R_{21}$ is H, a group comprising an active functional group, or a blocking group, provided that both $R_{20}$ and $R_{21}$ are not each H.

In certain embodiments, a "substituted alkyl" or "substituted heteroalkyl" refers to a $C_1$-$C_{14}$ straight- or branched-chain alkyl or heteroalkyl group that is substituted with up to 5 groups selected from the group consisting of —OH, $-NH_2$, $-NH-NH_2$, =O(OH), substituted aryl, and =O.

In one embodiment, one of $R_{20}$ and $R_{21}$ is a blocking group and the other of $R_{20}$ and $R_{21}$ is a group comprising an active functional group. In one embodiment, one of $R_{20}$ and $R_{21}$ is H and the other of $R_{20}$ and $R_{21}$ is a group comprising an active functional group. In one embodiment, one of $R_{20}$ and $R_{21}$ is H and the other of $R_{20}$ and $R_{21}$ is a blocking group. In one embodiment, each of $R_{20}$ and $R_{21}$ is a blocking group.

When one of $R_{20}$ and $R_{21}$ is a blocking group and the other of $R_{20}$ and $R_{21}$ is a group comprising an active functional group, the compound is suitably used as an intermediate in the production of the disclosed polymer conjugates.

When one of $R_{20}$ and $R_{21}$ is a blocking group and the other of $R_{20}$ and $R_{21}$ is H or when both of $R_{20}$ and $R_{21}$ are each a blocking group, the compound is suitably used as an active agent in the treatment methods disclosed herein. Without being bound by any particular theory, it is believed that the administration of a compound that has a blocking group on one or both of the first or second phenolic hydroxyl groups (i.e., $R_{20}$ and/or $R_{21}$) results in a compound that produces less skin irritation (as compared to a compound with free hydroxyl groups on both the first and second phenolic hydroxyl groups).

In those embodiments in which both $R_{20}$ and $R_{21}$ are a blocking group, the blocking groups on $R_{20}$ and $R_{21}$ may be the same or may be different. In those embodiments in which both $R_{20}$ and $R_{21}$ are a blocking group, the blocking groups on $R_{20}$ and $R_{21}$ may contain the same cleavable moiety or a different cleavable moiety. In those embodiments in which both $R_{20}$ and $R_{21}$ are a blocking group, the blocking groups on $R_{20}$ and $R_{21}$ contain the same cleavable moiety which may be an ester linkage.

Exemplary cleavable moieties include, but are not limited to, an ester linkage, a carboxylate ester linkage (—C(O)—O—), a carbonate ester linkage (—O—C(O)—O—), a carbamate linkage (—O—C(O)—NH—), am amide linkage (—C(O)—NH—), and a disulfide linkage (S—S); other cleavable moieties are discussed herein. In a particular embodiment, the first cleavable moiety is an ester linkage. In another particular embodiment, the cleavable moiety is a carboxylate ester linkage.

In one embodiment, the blocking group contains a second cleavable moiety or forms a second cleavable moiety when the blocking group forms a bond with the O atom of $R_{20}$ and/or $R_{21}$. In one embodiment, the blocking group forms the second cleavable moiety when the blocking group forms a bond with the O atom of $R_{20}$ and/or $R_{21}$. In one embodiment, the cleavable moiety is cleaved by a chemical reaction. In one aspect of this embodiment, the cleavage is by hydrolysis of an ester group or reduction, such as, but not limited to, reduction of a disulfide. In one embodiment, the cleavable moiety is cleaved by a substance that is naturally present or induced to be present in the subject. In one aspect of this embodiment, such a substance is an enzyme or polypeptide. Therefore, in one embodiment, the cleavable moiety is cleaved by an enzymatic reaction. In one embodiment, the cleavable moiety is cleaved by a combination of the foregoing.

In one embodiment, the blocking group of $R_{20}$ and/or $R_{21}$ is —$R_{22}$—$R_{23}$—, where $R_{22}$ is —C(O)—, —O—C(O)—, —C(O)—NH-cyclic-O—C(O)— (where cyclic represents substituted or unsubstituted aryl, heterocylalkyl, heteroaryl, heterocyclyl or cycloalkyl), —C(O)—NH—($C_6H_4$)—O—C(O)—, or —O—P(O)($OR_9$)(O)— (where $R_9$ is H or a substituted or unsubstituted C1-C5 alkyl) and $R_{23}$ is an unsubstituted or substituted alkyl, an unsubstituted or substituted alkenyl, an unsubstituted or substituted aralkyl or an unsubstituted or substituted aryl group.

In one embodiment, $R_{22}$ forms a bond with the oxygen atom of $R_{20}$ and/or $R_{21}$ and $R_{22}$ and the O to which it is linked forms a cleavable moiety. In one embodiment, the cleavable moiety is —C(O)—O.

In one embodiment, $R_{23}$ is a substituted or unsubstituted alkyl. In one embodiment, $R_{23}$ is a substituted or unsubstituted C1-C6 alkyl. In one embodiment, $R_{23}$ is a substituted or unsubstituted C1-C6 straight chain alkyl. In one embodiment, $R_{23}$ is a substituted or unsubstituted C1-C6 branched chain alkyl. In one embodiment, $R_{23}$ is a substituted or unsubstituted aralkyl. In one embodiment, $R_{23}$ is a substituted or unsubstituted aryl.

In one embodiment, the blocking group has the structure $(CH_3)_y$—$(CH_x)$—$(CH_2)_{0\text{-}6}$—C(O)—O-compound, wherein when y is 1, x is 2, when y is 2, x is 1, or when y is 3, x is 0. In one embodiment, the blocking group has the structure $(CH_3)_y$—$(CH_x)$—C(O)—O-compound, wherein when y is 1, x is 2, when y is 2, x is 1, or when y is 3, x is 0. In one embodiment, the blocking group has the structure $CH_3$—$(CH_2)_{0\text{-}6}$—C(O)—O-compound. In one embodiment, the blocking group has the structure $CH_3$—$(CH_2)_{0\text{-}6}$—C(O)—$(CH_2)_{0\text{-}6}$—O-compound. In the foregoing, the underlined portion represents a portion of the compound comprising a catechol moiety and is not considered a part of the blocking group.

In one embodiment, the blocking group has the structure $(CH_3)$—C(O)—O-compound. In one embodiment, the blocking group has the structure $CH_3$—$(CH_2)_2$—C(O)—O-compound. In one embodiment, the blocking group has the structure $CH_3$—$CH_2$—C(O)—O-compound. In one embodiment, the blocking group has the structure $(CH_3)_2$—CH—C(O)—O-compound. In one embodiment, the blocking group has the structure $(CH_3)_3$—C—C(O)—O-compound. In one embodiment, the blocking group has the structure $CH_3CH_2$—O—C(O)—$CH_2CH_2$—C(O)—O-compound. In one embodiment, the blocking group has the structure

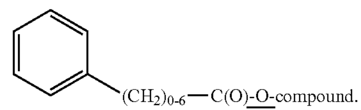

In one embodiment, the blocking group has the structure

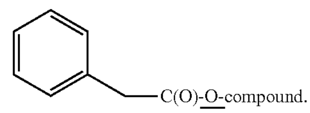

In the foregoing, the underlined portion represents a portion of the compound comprising a catechol moiety and is not considered a part of the blocking group.

In one embodiment, the group comprising an active functional group is $R_{24}$—$R_{25}$—$R_{26}$, wherein $R_{24}$ is —C(O)—, —O—C(O)—, —C(O)—NH-cyclic-O—C(O)— (where cyclic represents substituted or unsubstituted aryl, heterocylalkyl, heteroaryl, heterocyclyl or cycloalkyl), —C(O)—NH—($C_6H_4$)—O—C(O)—, or —O—P(O)($OR_9$)(O)— (where $R_9$ is H or a substituted or unsubstituted C1-C5 alkyl), $R_{25}$ is an unsubstituted or substituted alkyl, an unsubstituted or substituted alkenyl, an unsubstituted or substituted aralkyl or an unsubstituted or substituted aryl group, and $R_{26}$ is an active functional group or a moiety comprising an active functional group capable of forming a linkage with a group on the polymer, including a group at the pendent position of the polymer. In one embodiment, $R_{26}$ is an alkyne, amine, oxyamine, aldehyde, ketone, acetal, ketal, maleimide, ester, carboxylic acid, activated carboxylic acid (such as, but not limited to, N-hydroxysuccinimidyl (NHS) and 1-benzotriazineyl active ester), an active carbonate, a chloroformate, alcohol, azide, vinyl sulfone, and orthopyridyl disulfide (OPSS). In one embodiment, $R_{26}$ is an azide group ($N_3$) or an alkyne group. In one embodiment, $R_{24}$ forms a bond with the oxygen atom of the first phenolic hydroxyl group and $R_{24}$ and the O to which it is linked forms the first cleavable moiety. In one embodiment, the first cleavable moiety is —C(O)—O.

In one embodiment, $R_{25}$ is a substituted or unsubstituted alkyl. In one embodiment, $R_{25}$ is a substituted or unsubstituted C1-C6 alkyl. In one embodiment, $R_{25}$ is a substituted or unsubstituted C1-C6 straight chain alkyl. In one embodiment, $R_{25}$ is a substituted or unsubstituted C1-C6 branched chain alkyl.

In one embodiment, $R_{26}$ is $N_3$. When $R_{26}$ is $N_3$, the compound of formula V may be linked to a polymer comprising an alkyne group (such as but not limited to, acetylene), via copper(I) catalyzed azide-acetylene click chemistry. In such a reaction, the compound of formula V is linked to an azide group as described herein and a copper(I) catalyzed click reaction is executed with an alkyne group on the polymer. In one embodiment of the foregoing, the alkyne group is in a pendent position on the polymer. In one embodiment of the foregoing, the polymer is a polyoxazoline polymer and the alkyne group is in a pendent position on the polyoxazoline polymer.

In one embodiment, $R_{26}$ is an alkyne. When $R_{26}$ is an alkyne (such as but not limited to, acetylene), the compound of formula V may be linked to a polymer comprising a $N_3$ group, via copper(I) catalyzed azide-acetylene click chemistry. In such a reaction, the compound of formula V is linked to an alkyne group as described herein and a copper(I) catalyzed click reaction is executed with an azide group on the polymer. In one embodiment of the foregoing, the azide group is in a pendent position on the polymer. In one embodiment of the foregoing, the polymer is a polyoxazoline polymer and the azide group is in a pendent position on the polyoxazoline polymer.

In one embodiment, the group comprising an active functional group has the structure $N_3$—$(CH_2)_{1-6}$—C(O)—<u>O</u>-compound. In one embodiment, the group comprising an active functional group has the structure C≡C—$(CH_2)_{1-6}$—C(O)—<u>O</u>-compound. In one embodiment, the group comprising an active functional group has the structure $N_3$—$(CH_2)_3$—C(O)—<u>O</u>-compound. In one embodiment, the group comprising an active functional group has the structure C≡C—$(CH_2)_3$—C(O)—<u>O</u>-compound. In the foregoing, the underlined portion represents a portion of the compound comprising a catechol moiety and is not considered a part of the group comprising an active functional group.

In one embodiment, one of $R_{20}$ and $R_{21}$ is a blocking group and the other of $R_{20}$ and $R_{21}$ is H. In another embodiment, each of $R_{20}$ and $R_{21}$ is a blocking group the blocking groups on $R_{20}$ and $R_{21}$ are the same. In another embodiment, each of $R_{20}$ and $R_{21}$ is a blocking group the blocking groups on $R_{20}$ and $R_{21}$ are different. In those embodiments in which both $R_{20}$ and $R_{21}$ are a blocking group, the blocking groups on $R_{20}$ and $R_{21}$ contain the same cleavable moiety. In those embodiments in which both $R_{20}$ and $R_{21}$ are a blocking group, the blocking groups on $R_{20}$ and $R_{21}$ contain a different cleavable moiety. In those embodiments in which both $R_{20}$ and $R_{21}$ are a blocking group, the blocking groups on $R_{20}$ and $R_{21}$ contain an ester linkage as the cleavable moiety. Those embodiments in which one or both of $R_{20}$ and $R_{21}$ are a blocking group may be used as active agents in the methods of treatment described herein without being linked to a water-soluble polymer (i.e., not a component of a polymer conjugate as described above).

In one embodiment, the present disclosure provides an intermediate of the formula VI, or a pharmaceutically acceptable salt thereof.

VI

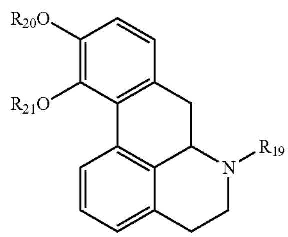

wherein $R_{19}$ is H, unsubstituted alkyl, alkenyl, or alkynyl, substituted alkyl, alkenyl, or alkynyl, benzyl, substituted benzyl, cycloalkyl, substituted cycloalkyl, aryl, substituted aryl, acyl, tetrahydrofuranyl, tetrahydropyranyl, nicotinyl or a 1-aryltetrazolyl; and one of $R_{20}$ and $R_{21}$ is H or a blocking group and the other of $R_{20}$ and $R_{21}$ is H, a group comprising an active functional group, or a blocking group, provided that both $R_{20}$ and $R_{21}$ are not each H.

In one embodiment, $R_{19}$ is straight chain substituted or unsubstituted alkyl group of 1 to 5 carbons in length. In one embodiment, $R_{19}$ is selected from the group consisting of —H, —$CH_3$, —$CH_2$—$CH_3$, —$CH_2$—$CH_2$—$CH_3$, —CH$(CH_3)_2$—$CH_2$—$CH_2$—$CH_2$—$CH_3$, and

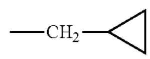

In one embodiment, $R_{19}$ is $CH_3$.

In one embodiment, one of $R_{20}$ and $R_{21}$ is a blocking group and the other of $R_{20}$ and $R_{21}$ is a group comprising an active functional group. In one embodiment, one of $R_{20}$ and $R_{21}$ is H and the other of $R_{20}$ and $R_{21}$ is a group comprising an active functional group. In one embodiment, one of $R_{20}$ and $R_{21}$ is H and the other of $R_{20}$ and $R_{21}$ is a blocking group. In one embodiment, each of $R_{20}$ and $R_{21}$ is a blocking group.

In those embodiments in which both $R_{20}$ and $R_{21}$ are a blocking group, the blocking groups on $R_{20}$ and $R_{21}$ may be the same or may be different. In those embodiments in which both $R_{20}$ and $R_{21}$ are a blocking group, the blocking groups on $R_{20}$ and $R_{21}$ may contain the same cleavable moiety or a different cleavable moiety. In those embodiments in which both $R_{20}$ and $R_{21}$ are a blocking group, the blocking groups on $R_{20}$ and $R_{21}$ contain the same cleavable moiety, which may be an ester linkage.

Exemplary cleavable moieties include, but are not limited to, an ester linkage, a carboxylate ester linkage (—C(O)—O—), a carbonate ester linkage (—O—C(O)—O—), a carbamate linkage (—O—C(O)—NH—), am amide linkage (—C(O)—NH—), and a disulfide linkage (S—S); other cleavable moieties are discussed herein. In a particular embodiment, the first cleavable moiety is an ester linkage. In another particular embodiment, the cleavable moiety is a carboxylate ester linkage.

In one embodiment, the blocking group contains a second cleavable moiety or forms a second cleavable moiety when the blocking group forms a bond with the O atom of $R_{20}$ and/or $R_{21}$. In one embodiment, the blocking group forms the second cleavable moiety when the blocking group forms a bond with the O atom of $R_{20}$ and/or $R_{21}$. In one embodiment, the cleavable moiety is cleaved by a chemical reaction. In one aspect of this embodiment, the cleavage is by hydrolysis of an ester group or reduction, such as, but not limited to, reduction of a disulfide. In one embodiment, the cleavable moiety is cleaved by a substance that is naturally present or induced to be present in the subject. In one aspect of this embodiment, such a substance is an enzyme or polypeptide. Therefore, in one embodiment, the cleavable moiety is cleaved by an enzymatic reaction. In one embodiment, the cleavable moiety is cleaved by a combination of the foregoing.

In one embodiment, the blocking group is —$R_{22}$—$R_{23}$—, where $R_{22}$ is —C(O)—, —O—C(O)—, —C(O)—NH-cyclic-O—C(O)— (where cyclic represents substituted or unsubstituted aryl, heterocylalkyl, heteroaryl, heterocyclyl or cycloalkyl), —C(O)—NH—(C6$H_4$)—O—C(O)—, or —O—P(O)($OR_9$)(O)— (where $R_9$ is H or a substituted or unsubstituted C1-C5 alkyl) and $R_{23}$ is an unsubstituted or substituted alkyl, an unsubstituted or substituted alkenyl, an unsubstituted or substituted aralkyl or an unsubstituted or substituted aryl group In one embodiment, $R_{22}$ forms a bond with the oxygen atom of the second phenolic hydroxyl group and $R_{22}$ and the O to which it is linked forms the second cleavable moiety. In one embodiment, the second cleavable moiety is —C(O)—O.

In one embodiment, $R_{23}$ is a substituted or unsubstituted alkyl. In one embodiment, $R_{23}$ is a substituted or unsubstituted C1-C6 alkyl. In one embodiment, $R_{23}$ is a substituted or unsubstituted C1-C6 straight chain alkyl. In one embodiment, $R_{23}$ is a substituted or unsubstituted C1-C6 branched chain alkyl. In one embodiment, $R_{23}$ is a substituted or unsubstituted aralkyl. In one embodiment, $R_{23}$ is a substituted or unsubstituted aryl.

In one embodiment, the blocking group has the structure $(CH_3)_y$—$(CH_x)$—$(CH_2)_{0\text{-}6}$—C(O)—O-compound, wherein when y is 1, x is 2, when y is 2, x is 1, or when y is 3, x is 0. In one embodiment, the blocking group has the structure $(CH_3)_y$—$(CH_x)$—C(O)—O-compound, wherein when y is 1, x is 2, when y is 2, x is 1, or when y is 3, x is 0. In one embodiment, the blocking group has the structure $CH_3$—$(CH_2)_{0\text{-}6}$—C(O)—O-compound. In one embodiment, the blocking group has the structure $CH_3$—$(CH_2)_{0\text{-}6}$—C(O)—$(CH_2)_{0\text{-}6}$—O-compound. In the foregoing, the underlined portion represents a portion of the compound comprising a catechol moiety and is not considered a part of the blocking group.

In one embodiment, the blocking group has the structure $(CH_3)$—C(O)—O-compound. In one embodiment, the blocking group has the structure $CH_3$—$(CH_2)_2$—C(O)—O-compound. In one embodiment, the blocking group has the structure $CH_3$—$CH_2$—C(O)—O-compound. In one embodiment, the blocking group has the structure $(CH_3)_2$—CH—C(O)—O-compound. In one embodiment, the blocking group has the structure $(CH_3)_3$—C—C(O)—O-compound. In one embodiment, the blocking group has the structure $CH_3CH_2$—O—C(O)—$CH_2CH_2$—C(O)—O-compound. In one embodiment, the blocking group has the structure

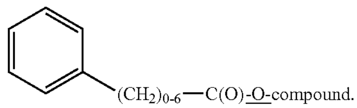

In one embodiment, the blocking group has the structure

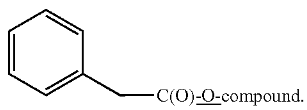

In the foregoing, the underlined portion represents a portion of the compound comprising a catechol moiety. In the foregoing, the underlined portion represents a portion of the compound comprising a catechol moiety and is not considered a part of the blocking group.

In one embodiment, the group comprising an active functional group is $R_{24}$—$R_{25}$—$R_{26}$, wherein $R_{24}$ is —C(O)—, —O—C(O)—, —C(O)—NH-cyclic-O—C(O)— (where cyclic represents substituted or unsubstituted aryl, heterocycloalkyl, heteroaryl, heterocyclyl or cycloalkyl), —C(O)—NH—(C6$H_4$)—O—C(O)—, or —O—P(O)($OR_9$)(O)— (where $R_9$ is H or a substituted or unsubstituted C1-C5 alkyl), $R_{25}$ is an unsubstituted or substituted alkyl, an unsubstituted or substituted alkenyl, an unsubstituted or substituted aralkyl or an unsubstituted or substituted aryl group, and $R_{26}$ is a moiety comprising a reactive group capable of forming a linkage with a group on the polymer, including a group at the pendent position of the polymer. In one embodiment, $R_{26}$ is an alkyne, amine, oxyamine, aldehyde, ketone, acetal, ketal, maleimide, ester, carboxylic acid, activated carboxylic acid (such as, but not limited to, N-hydroxysuccinimidyl (NHS) and 1-benzotriazineyl active ester), an active carbonate, a chloroformate, alcohol, azide, vinyl sulfone, and orthopyridyl disulfide (OPSS). In one embodiment, $R_{26}$ is an azide group ($N_3$) or an alkyne group. In one embodiment, $R_{24}$ forms a bond with the oxygen atom of the first phenolic hydroxyl group and $R_{24}$ and the O to which it is linked forms the first cleavable moiety. In one embodiment, the second cleavable moiety is —C(O)—O.

In one embodiment, $R_{25}$ is a substituted or unsubstituted alkyl. In one embodiment, $R_{25}$ is a substituted or unsubstituted C1-C6 alkyl. In one embodiment, $R_{25}$ is a substituted or unsubstituted C1-C6 straight chain alkyl. In one embodiment, $R_{25}$ is a substituted or unsubstituted C1-C6 branched chain alkyl.

In one embodiment, $R_{26}$ is $N_3$. When $R_{26}$ is $N_3$, the compound of formula V may be linked to a polymer comprising an alkyne group (such as but not limited to, acetylene), via copper(I) catalyzed azide-acetylene click chemistry. In such a reaction, the compound of formula V is linked to an azide group as described herein and a copper(I) catalyzed click reaction is executed with an alkyne group on the polymer. In one embodiment of the foregoing, the alkyne group is in a pendent position on the polymer. In one embodiment of the foregoing, the polymer is a polyoxazoline polymer and the alkyne group is in a pendent position on the polyoxazoline polymer.

In one embodiment, $R_{26}$ is an alkyne. When $R_{26}$ is an alkyne (such as but not limited to, acetylene), the compound of formula V may be linked to a polymer comprising a $N_3$ group, via copper(I) catalyzed azide-acetylene click chemistry. In such a reaction, the compound of formula V is linked to an alkyne group as described herein and a copper(I) catalyzed click reaction is executed with an azide group on the polymer. In one embodiment of the foregoing, the azide group is in a pendent position on the polymer. In one embodiment of the foregoing, the polymer is a polyoxazoline polymer and the azide group is in a pendent position on the polyoxazoline polymer.

In one embodiment, the group comprising an active functional group has the structure $N_3$—$(CH_2)_{1\text{-}6}$—C(O)—O-compound. In one embodiment, the blocking group has the structure C≡C—$(CH_2)_{1\text{-}6}$—C(O)—O-compound. In one embodiment, the group comprising an active functional group has the structure $N_3$—$(CH_2)_3$—C(O)—O-compound. In one embodiment, the blocking group has the structure C≡C—$(CH_2)_3$—C(O)—O-compound. In the foregoing, the underlined portion represents a portion of the compound comprising a catechol moiety and is not considered a part of the group comprising an active functional group.

Certain preferred compounds according to the present disclosure for use as intermediates are provided below.

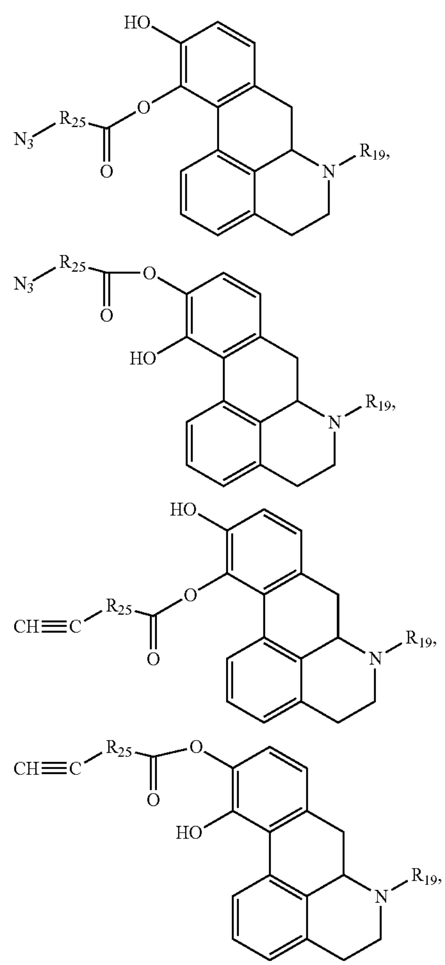

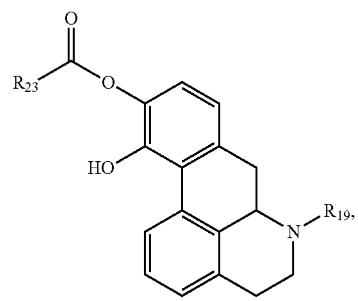

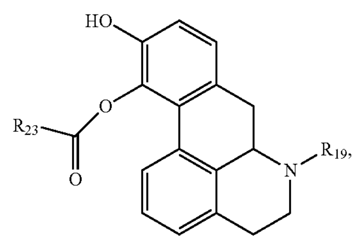

-continued

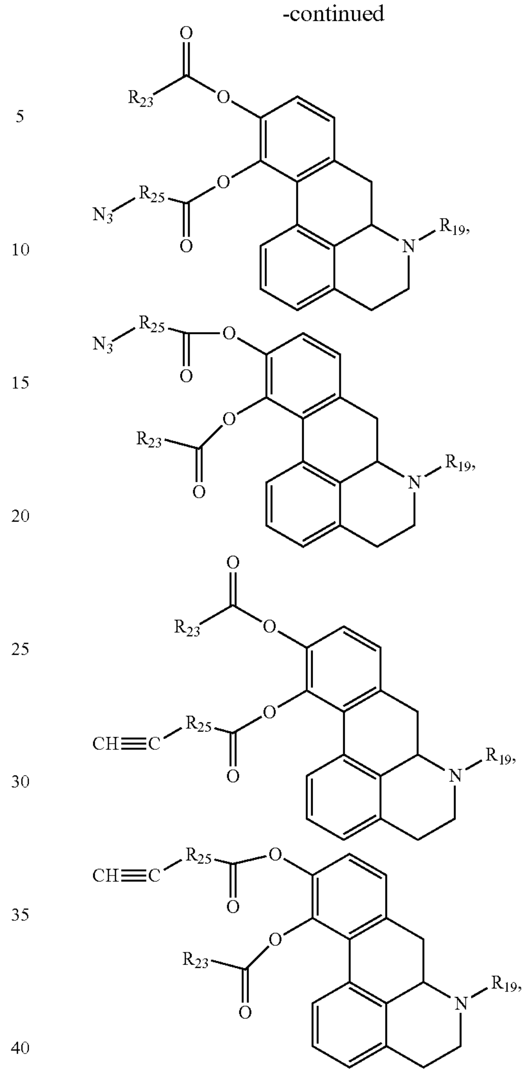

and the compounds of the examples.

In the foregoing preferred compounds according to the present disclosure, $R_{19}$, $R_{23}$, and $R_{25}$ may be as described herein.

In one embodiment, $R_{19}$ is selected from the group consisting of —H, $CH_3$, $—CH_2—CH_3$, $—CH_2—CH_2—CH_3$, and

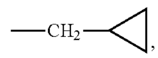

$R_{23}$ (when present) is an unsubstituted or substituted alkyl, an unsubstituted or substituted alkenyl, an unsubstituted or substituted aralkyl or an unsubstituted or substituted aryl group, and $R_{25}$ (when present) is $—(CH_2)_{1-6}—$ or $—(CH_2)_3—$.

In one embodiment, $R_{10}$ is selected from the group consisting of —H, $CH_3$, $—CH_2—CH_3$, $—CH_2—CH_2—CH_3$, and

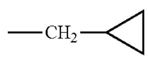

$R_{23}$ (when present) is $(CH_3)_y$—$(CH_x)$—$(CH_2)_{0-6}$—C(O)—, wherein when y is 1, x is 2, when y is 2, x is 1, or when y is 3, x is 0, $(CH_3)_y$—$(CH_x)$—C(O)—, wherein when y is 1, x is 2, when y is 2, x is 1, or when y is 3, x is 0, $CH_3$—$(CH_2)_{0-6}$—C(O)—, or $CH_3$—$(CH_2)_{0-6}$—C(O)—$(CH_2)_{0-6}$—, and $R_{25}$ (when present) is —$(CH_2)_{1-6}$— or —$(CH_2)_3$—.

In one embodiment, $R_{19}$ is selected from the group consisting of —H, $CH_3$, —$CH_2$—$CH_3$, —$CH_2$—$CH_2$—$CH_3$, and

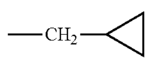

$R_{23}$ (when present) is $CH_3$—, $CH_3$—$(CH_2)_2$—, $CH_3$—$CH_2$—, $(CH_3)_2$—CH—, $(CH_3)_3$—C—, or

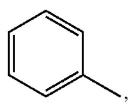

and $R_{25}$ (when present) is —$(CH_2)_{1-6}$— or —$(CH_2)_3$—.

In any of the foregoing, $R_{19}$ is $CH_3$.

Certain preferred compounds according to the present disclosure for use as active agents are provided below.

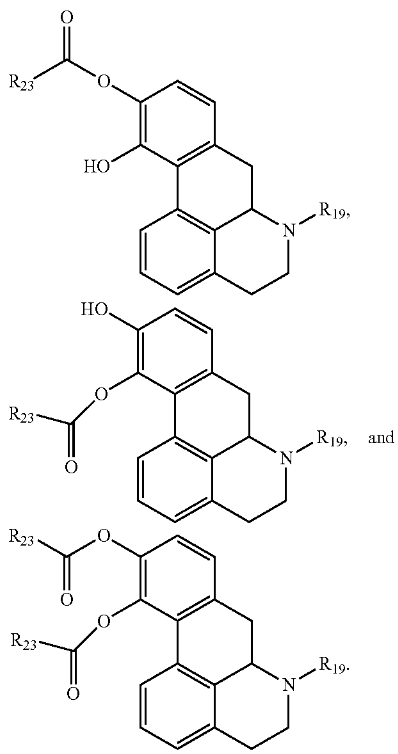

In the foregoing preferred compounds according to the present disclosure, $R_{19}$ and $R_{23}$ may be as described herein.

Without being bound by any particular theory, it is believed that the administration of a compound that has a blocking group on at least one of the first or second phenolic hydroxyl groups results in a compound that produces less skin irritation (as compared to a compound with free hydroxyl groups on both the first and second phenolic hydroxyl groups).

In one embodiment, Rig is selected from the group consisting of —H, $CH_3$, —$CH_2$—$CH_3$, —$CH_2$—$CH_2$—$CH_3$, and

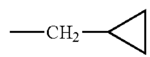

and $R_{23}$ is (or when two $R_{23}$ groups are present, are independently selected from) an unsubstituted or substituted alkyl, an unsubstituted or substituted alkenyl, an unsubstituted or substituted aralkyl or an unsubstituted or substituted aryl group.

In one embodiment, $R_{19}$ is selected from the group consisting of —H, $CH_3$, —$CH_2$—$CH_3$, —$CH_2$—$CH_2$—$CH_3$, and

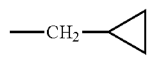

and $R_{23}$ is (or when two $R_{23}$ groups are present, are independently selected from) $(CH_3)_y$—$(CH_x)$—$(CH_2)_{0-6}$—C(O)—, wherein when y is 1, x is 2, when y is 2, x is 1, or when y is 3, x is 0, $(CH_3)_y$—$(CH_x)$—C(O)—, wherein when y is 1, x is 2, when y is 2, x is 1, or when y is 3, x is 0, $CH_3$—$(CH_2)_{0-6}$—C(O)—, or $CH_3$—$(CH_2)_{0-6}$—C(O)—$(CH_2)_{0-6}$—.

In one embodiment, Rig is selected from the group consisting of —H, $CH_3$, —$CH_2$—$CH_3$, —$CH_2$—$CH_2$—$CH_3$, and

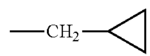

and $R_{23}$ is (or when two $R_{23}$ groups are present, are independently selected from) $CH_3$—, $CH_3$—$(CH_2)_2$—, $CH_3$—$CH_2$—, $(CH_3)_2$—CH—, $(CH_3)_3$—C—, or

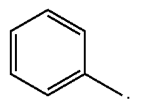

In any of the foregoing, $R_{19}$ is $CH_3$.

Methods of Treatment

The present disclosure also provides polymer conjugates of the formula I, II, IIA, and IIB for use as active agents in the methods of treatment described herein. Such conjugates comprise polymer portion linked to a compound comprising a catechol moiety via a first cleavable linkage, wherein the cleavable linkage is formed between the polymer and a first phenolic hydroxyl group of the catechol moiety and a second phenolic hydroxyl group of the catechol moiety is linked to a blocking group, wherein the cleavage (i.e., the release rate) of the compound comprising the catechol moiety is controlled, at least in part, through the structure and/or design of the blocking group. The present disclosure further shows that the release of the compound from the polymer conjugate can be controlled. In one aspect, the compound is delivered with a pharmacokinetic/release profile that lacks peaks and troughs as seen in prior art treatments. In one aspect, a near steady state release of the compound from the polymer conjugate is achieved over a period of time (for example 12 hours to 168 hours).

In one embodiment, the conjugates provide for the delivery of a therapeutically effective amount of the compound to the subject over a period of time from: 12 hours to 24 hours; 24 hours to 48 hours; 24 hours to 72 hours; 24 hours to 96 hours; 24 hours to 120 hours; 24 hours to 144 hours; or 24 hours to 168 hours. In any of the foregoing embodiments, the delivery is a controllable delivery or a sustained controllable delivery. In any of the foregoing embodiments, the compound is delivered with a pharmacokinetic/release profile that lacks peaks and troughs.

In one embodiment, the conjugates provide for the delivery of a therapeutically effective amount of the compound to the subject over a period of one week or more. In one embodiment, the conjugates provide for the delivery of a therapeutically effective amount of the compound to the subject over a period of time from: one to two weeks; one to three weeks; or one to four weeks. In any of the foregoing embodiments, the delivery is a controllable delivery or a sustained controllable delivery. In any of the foregoing embodiments, the compound is delivered with a pharmacokinetic/release profile that lacks peaks and troughs.

In one embodiment, the delivery provides a release profile that provides a therapeutically effective amount of the compound over such time periods. As a result, the polymer conjugates of the present disclosure are useful for treating human disease through appropriate selection of the compound and/blocking group. Furthermore, the polymer conjugates of the present disclosure allow for less frequent administration as compared to the art to achieve therapeutically effective amount of the compound in a subject. In one embodiment, polymer conjugates of the present disclosure are administered once a day, once every other day, once a week, once every two weeks, once every three weeks, once a month, or at other desired intervals.

The present disclosure also provides compounds of the formula V or VI for use as active agents in the methods of treatment described herein. The generation of one or both free hydroxy groups on the compounds of formula V or IV is controlled, at least in part, through the structure of the blocking group on the first and/or second hydroxyl groups.

The present disclosure provides for a variety of treatment methods using the conjugates and compounds of the present disclosure. The present disclosure provides a method of treating a disease or condition, the method comprising the step of administering to the subject an amount of a polymer conjugate or compound (for example, a compound of the formula V and/or VI) of the present disclosure to a subject, wherein the disease or condition is selected based on the compound that is a part of the polymer conjugate. For example, when the compound is a dopamine agonist, the disease or condition to be treated may be a disease or condition related to dopamine insufficiency in the peripheral or central nervous system. In another example, when the compound is a dopamine agonist, the disease or condition to be treated may be a hypodopaminergic condition, pituitary tumors (prolactinoma), Parkinson's disease, restless leg syndrome, schizophrenia, attention-deficit hyperactivity disorder, hypodopaminergic conditions, SSRI-induced sexual dysfunction, depression, obesity, and type TT diabetes. Other diseases and conditions that may be treated are described in Rubi et al. (Endocrinology, 151(12), 5570-5581, 2010, which reference is incorporated by reference for such teaching).

The compounds comprising a catechol moiety have been reported to treat a variety of diseases and conditions as recited in Yang et al. (Molecules, 2007, 12, 878-884), which reference is incorporated by reference for such teaching.

The present disclosure provides a method of treating a dopamine-responsive disease or condition, the method comprising the step of administering to the subject an amount of a polymer conjugate or compound (for example, a compound of the formula V and/or VI) of the present disclosure to a subject, wherein the agent is a dopamine agonist. In one embodiment, the dopamine-responsive disease or condition is a hypodopaminergic condition, pituitary tumors (prolactinoma) Parkinson's disease, restless leg syndrome, schizophrenia, attention-deficit hyperactivity disorder, hypodopaminergic conditions, SSRI-induced sexual dysfunction, depression, obesity, and type II diabetes. In another embodiment, such disease or condition is Parkinson's disease. In another embodiment, such disease or condition is restless leg syndrome.

The present disclosure provides a method of treating Parkinson's disease, the method comprising the step of administering to the subject an amount of a polymer conjugate or compound (for example, a compound of the formula V and/or VI) of the present disclosure to a subject, wherein the agent is a dopamine agonist.

The present disclosure provides a method of treating dopamine insufficiency in the peripheral or central nervous system, the method comprising the step of administering to the subject an amount of a polymer conjugate or compound (for example, a compound of the formula V and/or VI) of the present disclosure to a subject wherein the agent is a dopamine agonist.

In any of the foregoing methods of treatment, one or more of the following may apply to each method of treatment described.

In any of the foregoing embodiments, any polymer conjugate described herein may be used and the compound may be selected based on the disease or condition to be treated.

In any of the foregoing embodiments where the polymer conjugate is a poly(oxazoline) polymer conjugate, the poly (oxazoline) polymer conjugate may have the general formula as shown for formula II-IIB.

In any of the foregoing embodiments, the polymer is a polyoxazoline polymer.

In any of the foregoing embodiments, the compound is a compound of formula III or IV or a compound in FIG. 1 or Table 1S of Yang et al. (Molecules, 2007, 12, 878-884). In one embodiment, the compound comprising a catechol moiety is a compound described in Yang et al. (including in particular, FIG. 1 and Table S 1) that is useful in treating a dopamine responsive condition, such as, but not limited to, Parkinson's disease. In one embodiment, the compound comprising a catechol moiety is apomorphine, fenoldopam, entacapone, or tolcapone.

In any of the foregoing embodiments, the polymer is a polyoxazoline polymer and the compound is a compound of formula III or IV or a compound in FIG. 1 or Table 1S of Yang et al. (Molecules, 2007, 12, 878-884). In any of the foregoing embodiments, the polymer is a polyoxazoline polymer and the compound is a compound of formula III or IV or a compound described in Yang et al. (including in particular, FIG. 1 and Table Si) that is useful in treating a dopamine responsive condition, such as, but not limited to, Parkinson's disease. In one embodiment, the compound is apomorphine, arbutamine, carbidopa, dobutamine, dopamine, entacapone, epinephrine, fenoldopam, isoetharine, isoproterenol, levopoda, levonordefrin, masaprocol, methyldopa, methyldopate, norepinephrine, protokylol, tolcapone, or (r)-(+)-fenoldopam. In another embodiment, the compound is apomorphine, fenoldopam, entacapone, tolcapone, chf-1303, dopamantine, dopamine, droxipoda, etilevodopa, exifone, or levodopa. In another embodiment, the compound is apomorphine, fenoldopam, entacapone, tolcapone, or levodopa. In the foregoing list of exemplary compounds, it is understood that the first phenolic hydroxyl of the catechol moiety is modified by $R_{15}$, resulting in $OR_{15}$, and the second phenolic hydroxyl of the catechol moiety is modified by $R_{16}$, resulting in $OR_{16}$. In any of the foregoing embodiments, the polymer is a polyoxazoline polymer and the compound is a compound of formula III or IV or is apomorphine, fenoldopam, entacapone, or tolcapone.

In any of the foregoing embodiments, the polymer is a polyoxazoline polymer.

In any of the foregoing embodiments, the compound is a dopamine agonist, such as, but not limited to, apomorphine.

In any of the foregoing embodiments, the compound is fenoldopam, entacapone, or tolcapone.

In any of the foregoing embodiments, the polymer is a polyoxazoline polymer and the compound is a dopamine agonist, such as, but not limited to, apomorphine.

In any of the foregoing embodiments, the polymer is a polyoxazoline polymer and the compound is fenoldopam, entacapone, or tolcapone.

In any of the foregoing embodiments, the compound is apomorphine.

In any of the foregoing embodiments, the polymer is a polyoxazoline polymer and the compound is apomorphine.

In any of the foregoing embodiments, the polymer conjugate or compound (for example, a compound of the formula V and/or VI) may be administered alone or as a part of a pharmaceutical composition as described herein. In any of the foregoing embodiments, the subject may be determined to be in need of such treatment. In any of the foregoing embodiments, the polymer conjugate or compound (for example, a compound of the formula V and/or VI) is administered in a therapeutically effective amount. In any of the foregoing embodiments, the subject may be a mammal. In the foregoing embodiments, the subject may be a human.

In any of the foregoing embodiments, the methods of treatment may be accomplished by subcutaneous administration (for example, subcutaneous injection) of a polymer conjugate or compound (for example, a compound of the formula V and/or VI) of the present disclosure or pharmaceutical compositions containing such polymer conjugate or compound.

In any of the foregoing embodiments, the methods of treatment may be accomplished by subcutaneous administration of a compound (for example, a compound of the formula V and/or VI) of the present disclosure or pharmaceutical compositions containing such compound. Suitable routes of subcutaneous administration include, but are not limited to, subcutaneous injection or subcutaneous infusion. In a particular embodiment, the compounds of formula V and/or VI are compounds comprising a blocking group on one or both (preferably both) of the first and second phenolic hydroxyls, wherein the cleavable moiety on the blocking group(s) is an ester linkage. In another particular embodiment, the compound of formula V and/or VI is apomorphine comprising a blocking group on one or both (preferably both) of the first and second phenolic hydroxyls, wherein the cleavable moiety on the blocking group(s) is an ester linkage. Without being limited to any particular theory, compounds of the formula V and VI comprising a blocking group on one or both (preferably both) of the first and second phenolic hydroxyls, wherein the cleavable moiety on the blocking group(s) is an ester linkage, are advantageously administered to a subject via subcutaneous infusion without the side effects (such as, but not limited to, skin irritation) seen with the administration of prior art compounds. As the enzymes required for cleavage of an ester linkage are not present in the blood of a human subject, the cleavable moiety on the blocking group(s) is not cleaved on subcutaneous administration (including subcutaneous injection or subcutaneous infusion). As a result, the hydroxyl groups of the catechol moiety are not exposed on the compound until the compound exits the subcutaneous space, thereby reducing the side effects of administration seen in the prior art (particularly when the compound is apomorphine).

Preferred apomorphine compounds for administration by subcutaneous injection or subcutaneous infusion include, but are not limited to, the compounds below:

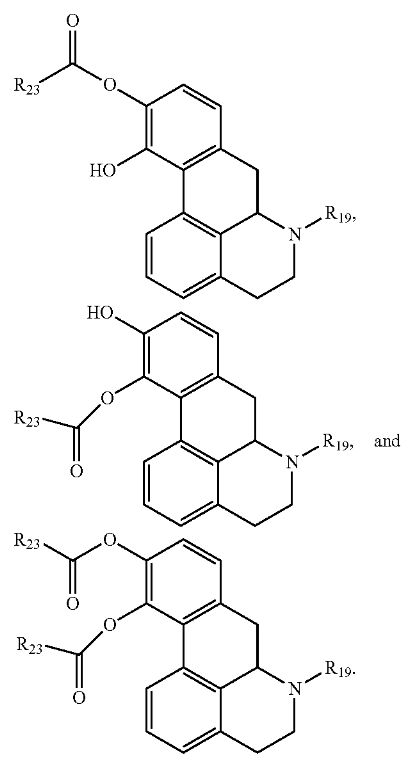

and

In any of the foregoing embodiments, the polymer conjugate, either alone or as a part of a pharmaceutical composition, is administered once a day. In any of the foregoing embodiments, the polymer conjugate, either alone or as a part of a pharmaceutical composition, is administered once every other day. In any of the foregoing embodiments, the polymer conjugate, either alone or as a part of a pharmaceutical composition, is administered every third day, every fourth day, every fifth day or every sixth day. In any of the foregoing embodiments, the polymer conjugate, either alone or as a part of a pharmaceutical composition, is administered once a week. In any of the foregoing embodiments, the polymer conjugate, either alone or as a part of a pharmaceutical composition, is administered once every two weeks. In any of the foregoing embodiments, the polymer conjugate, either alone or as a part of a pharmaceutical composition, is administered once every four weeks. Other dosing frequencies may also be used based on the nature of the polymer conjugate selected and the release kinetics of the compound.

In any of the foregoing embodiments, the polymer conjugate, either alone or as a part of a pharmaceutical composition, is administered once a day by subcutaneous administration. In any of the foregoing embodiments, the polymer conjugate, either alone or as a part of a pharmaceutical composition, is administered once every other day by subcutaneous administration. In any of the foregoing embodiments, the polymer conjugate, either alone or as a part of a pharmaceutical composition, is administered every third day, every fourth day, every fifth day or every sixth day by subcutaneous administration. In any of the foregoing embodiments, the polymer conjugate, either alone or as a part of a pharmaceutical composition, is administered once a week by subcutaneous administration. In any of the foregoing embodiments, the polymer conjugate, either alone or as a part of a pharmaceutical composition, is administered once every two weeks by subcutaneous administration. In any of the foregoing embodiments, the polymer conjugate, either alone or as a part of a pharmaceutical composition, is administered once every four weeks by subcutaneous administration. Other dosing frequencies may also be used based on the nature of the polymer conjugate selected and the release kinetics of the compound.

In any of the foregoing embodiments, the polymer conjugate is a polyoxazoline polymer and the compound is apomorphine and the polymer conjugate, either alone or as a part of a pharmaceutical composition, is administered once a day by subcutaneous administration. In any of the foregoing embodiments, the polymer conjugate is a polyoxazoline polymer and the compound is apomorphine and the polymer conjugate, either alone or as a part of a pharmaceutical composition, is administered once every other day by subcutaneous administration. In any of the foregoing embodiments, the polymer conjugate is a polyoxazoline polymer and the compound is apomorphine and the polymer conjugate, either alone or as a part of a pharmaceutical composition, is administered every third day, every fourth day, every fifth day or every sixth day by subcutaneous administration. In any of the foregoing embodiments, the polymer conjugate is a polyoxazoline polymer and the compound is apomorphine and the polymer conjugate, either alone or as a part of a pharmaceutical composition, is administered once a week by subcutaneous administration. In any of the foregoing embodiments, the polymer conjugate is a polyoxazoline polymer and the compound is apomorphine and the polymer conjugate, either alone or as a part of a pharmaceutical composition, is administered once every two weeks by subcutaneous administration. In any of the foregoing embodiments, the polymer conjugate is a polyoxazoline polymer and the compound is apomorphine and the polymer conjugate, either alone or as a part of a pharmaceutical composition, is administered once every four weeks by subcutaneous administration. Other dosing frequencies may also be used based on the nature of the polymer conjugate selected and the release kinetics of the compound.

In any of the foregoing embodiments, the polymer conjugates described herein can also be administered in combination with other therapeutic agents, for example, other agents that are useful for treatment of a dopamine responsive disorder, such as, but not limited to, Parkinson's disease or any other condition recited herein. When administered with other therapeutic agents, the polymer conjugates of the present disclosure may be administered before, after or at the same time as the additional therapeutic agent. Accordingly, in one embodiment the present disclosure also provides a composition comprising a polymer conjugate described herein, at least one other therapeutic agent, and a pharmaceutically acceptable diluent or carrier.

Kits

The present disclosure provides a kit comprising, consisting essentially of or consisting of a water-soluble polymer, including, but not limited to, a polyoxazoline polymer, and an compound of the general formula V or VI and one or more of the following: reagents for the coupling of the intermediate to the polymer, packaging material and instructions for coupling of the intermediate to the polymer.

The present disclosure provides a kit comprising, consisting essentially of or consisting of a compound comprising a catechol moiety, reagents for forming a blocking group one of the phenolic hydroxyl groups of the catechol moiety and/or a functional group on the other of phenolic hydroxyl groups of the catechol moiety and one or more of the following: a water-soluble polymer, including, but not limited to, a polyoxazoline polymer, packaging material and instructions for forming a blocking group one of the phenolic hydroxyl groups of the catechol moiety and/or a functional group on the other of phenolic hydroxyl groups of the catechol moiety.

The present disclosure provides a kit comprising, consisting essentially of or consisting of a polymer conjugate of the present disclosure and one or more of the following: packaging material and instructions for administering the polymer conjugate to a subject for the treatment of a disease or condition, wherein the disease or condition is selected based on the compound that is a part of the polymer conjugate. For example, when the compound is a dopamine agonist, the disease or condition to be treated may be Parkinson's disease. The compounds comprising a catechol moiety have been reported to treat a variety of diseases and conditions as recited in Yang et al. (Molecules, 2007, 12, 878-884), which reference is incorporated by reference for such teaching.

The present disclosure provides a kit comprising, consisting essentially of or consisting of a polymer conjugate of the present disclosure and one or more of the following: packaging material and instructions for administering the polymer conjugate to a subject for the treatment of a dopamine-responsive disease or condition. In one embodiment, the dopamine-responsive disease or condition is a hypodopaminergic condition, Parkinson's disease, restless leg syndrome, schizophrenia, attention-deficit hyperactivity disorder, pituitary tumors (prolactinoma), hypodopaminergic conditions, SSRI-induced sexual dysfunction, depression, obesity, and type II diabetes. In one embodiment, such disease or condition is Parkinson's disease. In one embodiment, such disease or condition is restless leg syndrome.

The present disclosure provides a kit comprising, consisting essentially of or consisting of a polymer conjugate of the present disclosure and one or more of the following: packaging material and instructions for administering the polymer conjugate to a subject for the treatment of a hypodopaminergic condition.

The present disclosure provides a kit comprising, consisting essentially of or consisting of a polymer conjugate of the present disclosure and one or more of the following: packaging material and instructions for administering the polymer conjugate to a subject for the treatment of Parkinson's disease.

The present disclosure provides a kit comprising, consisting essentially of or consisting of a polymer conjugate of the present disclosure and one or more of the following: packaging material and instructions for administering the polymer conjugate to a subject for the treatment of restless leg syndrome.

In any of the kits described above, one or more of the following may also apply: i) the kit further comprises an additional active agent; ii) the kit further comprises an additional active agent and the instructions specify the administration of the additional active agent in relation to the administration of the polymer conjugate; iii) the instructions specify that the polymer conjugate is to administered by subcutaneous administration; iv) the instructions specify that the polymer conjugate is to administered by subcutaneous administration once a day, one every other day, once every third day, every fourth day, every fifth day or every sixth day, once a week, once every two weeks, or once every four weeks; v) the kit further comprises a delivery system, or a portion thereof, for the administration of the polymer conjugate; vi) the polymer conjugate is a poly(oxazoline) polymer conjugate, in one embodiment of the general formula as shown for formula II or III; vii) the compound is a compound of formula II or III or a compound in FIG. 1 or Table 1S of Yang et al. (Molecules, 2007, 12, 878-884); viii) the polymer is a polyoxazoline polymer and the compound is a compound of formula II or III or a compound in FIG. 1 or Table 1S of Yang et al. (Molecules, 2007, 12, 878-884); ix) the compound is fenoldopam, entacapone, or tolcapone; x) the compound is fenoldopam, entacapone, or tolcapone and the polymer is a polyoxazoline polymer; xi) the compound is apomorphine; xii) the compound is apomorphine and the polymer is a polyoxazoline polymer; xiii) the compound is a dopamine agonist; xiv) the compound is a dopamine agonist and the polymer is a polyoxazoline polymer;

In certain embodiments, all of i) to xiv) apply. In certain embodiments, one, two, three or four or more of i) to xiv) apply. In certain embodiments, at least one of iii), iv), and vi) to xiv) apply. In certain embodiments, two of iii), iv), and vi) to xii) apply.

Pharmaceutical Compositions and Routes of Administration

Pharmaceutical compositions are provided that comprise an amount of a polymer conjugate or compound (for example, a compound of the formula V and/or VI) of the present disclosure. In one embodiment, such pharmaceutical compositions contain a therapeutically effective amount of a conjugate or compound (for example, a compound of the formula V and/or VI) of the present disclosure. In a particular embodiment, the conjugate of the present disclosure is a conjugate of the formula I, II, IIA, or IIB. In a particular embodiment, the conjugate of the present disclosure is a conjugate of the formula I, II, IIA, or IIB and the polymer is a polyoxazoline polymer. In addition, other active agents may be included in such pharmaceutical compositions. Additional active agents to be included may be selected based on the disease or condition to be treated.

The pharmaceutical compositions disclosed may comprise one or more conjugates or compounds (for example, a compound of the formula V and/or VI) of the present disclosure, alone or in combination with additional active agents, in combination with a pharmaceutically acceptable carrier. Examples of such carriers and methods of formulation may be found in Remington: The Science and Practice of Pharmacy (20$^{th}$ Ed., Lippincott, Williams & Wilkins, Daniel Limmer, editor). Such conjugates and pharmaceutical compositions may be used in the manufacture of a medicament for use in the methods of treatment described herein. The conjugates or compounds (for example, a compound of the formula V and/or VI) of the disclosure are useful in both free form and in the form of pharmaceutically acceptable salts.

The pharmaceutically acceptable carriers described herein, including, but not limited to, vehicles, adjuvants, excipients, or diluents, are well-known to those who are skilled in the art. Pharmaceutically acceptable excipients are also well-known to those who are skilled in the art. The choice of excipient will be determined in part by the particular conjugate(s), as well as by the particular method used to administer the formulation. Accordingly, there is a wide variety of suitable formulations of the pharmaceutical composition. The following methods and excipients are merely exemplary and are in no way limiting. Suitable carriers and excipients include solvents such as water, alcohol, and propylene glycol, solid absorbents and diluents, surface active agents, suspending agent, tableting binders, lubricants, flavors, and coloring agents. The pharmaceutically acceptable carriers can include polymers and polymer matrices. Examples of acceptable pharmaceutical carriers include carboxymethyl cellulose, crystalline cellulose, glycerin, gum arabic, lactose, magnesium stearate, methyl cellulose, powders, saline, sodium alginate, sucrose, starch, talc and water, among others. Typically, the pharmaceutically acceptable carrier is chemically inert to the active agents in the composition and has no detrimental side effects or toxicity under the conditions of use. In some embodiments, the term "pharmaceutically acceptable" means approved by a regulatory agency of the Federal or a state government or listed in the U.S. Pharmacopeia or other generally recognized pharmacopeia for use in animals, and more particularly in humans.

In one embodiment, such pharmaceutical compositions contain a therapeutically effective amount of a conjugate or compound (for example, a compound of the formula V and/or VI) of the present disclosure. In a particular embodiment, the conjugate is a conjugate of formula I, II, IIA, or IIB. In addition, other active agents may be included in such pharmaceutical compositions. Additional active agents to be included may be selected based on the disease or condition to be treated.

The pharmaceutical compositions disclosed may comprise one or more conjugates or compounds (for example, a compound of the formula V and/or VI) of the present disclosure, alone or in combination with additional active agents, in combination with a pharmaceutically acceptable carrier.

The conjugates of the present disclosure and pharmaceutical compositions containing such conjugates or compounds (for example, a compound of the formula V and/or VI) can be administered by any conventional method available for use in conjunction with pharmaceuticals, either as individual therapeutic agents or in combination with additional therapeutic agents. One skilled in the art will appreciate that suitable methods of administering a conjugates of the present disclosure, either alone or in a pharmaceutical formulation, to an patient are available, and, although more than one route can be used and a particular route can provide a more immediate and more effective reaction than another route.

In one embodiment, the conjugates or compounds (for example, a compound of the formula V and/or VI) of the present disclosure are administered in therapeutically effective amount, whether alone or as a part of a pharmaceutical composition. The therapeutically effective amount and the dosage administered will, of course, vary depending upon known factors, such as the pharmacodynamic characteristics of the particular agent and its mode and route of administration, the age, health and weight of the recipient; the severity and stage of the disease state or condition; the kind of concurrent treatment; the frequency of treatment; and the effect desired.

The total amount of the conjugate or compound (for example, a compound of the formula V and/or VI) administered, whether alone or as a part of a pharmaceutical composition, will also be determined by the route, timing and frequency of administration as well as the existence, nature, and extent of any adverse side effects that might accompany the administration of the conjugate or compound and the desired physiological effect. It will be appreciated by one skilled in the art that various conditions or disease states, in particular chronic conditions or disease states, may require prolonged treatment involving multiple administrations.

In one embodiment of the pharmaceutical compositions, the conjugate(s) or compound(s) (for example, a compound of the formula V and/or VI) of the present disclosure will ordinarily be present in an amount of about 0.5-95% weight based on the total weight of the composition. Multiple dosage forms may be administered as part of a single treatment.

The conjugates or compounds (for example, a compound of the formula V and/or VI) of the present disclosure, either alone or as a part of a pharmaceutical composition, can be administered enterally in solid dosage forms, such as capsules, tablets, and powders, or in liquid dosage forms, such as milk, elixirs, syrups and suspensions. The conjugates or compounds (for example, a compound of the formula V and/or VI) of the present disclosure, either alone or as a part of a pharmaceutical composition, can also be administered parenterally, in sterile liquid dosage forms, intranasally (nose drops) or by inhalation via the pulmonary system, such as by propellant based metered dose inhalers or dry powders inhalation devices. Other dosage forms include topical administration, such as administration transdermally, via patch mechanism or ointment.

Formulations suitable for enteral or oral administration may be liquid solutions, such as a therapeutically effective amount of a conjugate or compound (for example, a compound of the formula V and/or VI) dissolved in diluents, such as milk, water, saline, buffered solutions, infant formula, other suitable carriers, or combinations thereof. The conjugate or compound can then be mixed to the diluent just prior to administration. In an altemate embodiment, formulations suitable for enteral or oral administration may be capsules, sachets, tablets, lozenges, and troches. In each embodiment, the formulation may contain a predetermined amount of the conjugate or compound of the present disclosure, as solids or granules, powders, suspensions and suitable emulsions. Liquid formulations may include diluents, such as water and alcohols, for example, ethanol, benzyl alcohol, propylene glycol, glycerin, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers.

Lozenge forms can comprise a conjugate in a flavor, usually sucrose and acacia or tragacanth, as well as pastilles comprising the active ingredient in an inert base, such as gelatin and glycerin, or sucrose and acadia, emulsions, and gels containing, in addition to the active ingredient, such carriers as are known in the art.

Formulations suitable for parenteral administration include aqueous and non-aqueous, isotonic sterile injection solutions, which can contain anti-oxidants, buffers, bacteriostats, and solutes that render the formulation isotonic with the blood of the patient, and aqueous and non-aqueous sterile suspensions that can include suspending agents, solubilizers, thickening agents, stabilizers, and preservatives. The conjugate or compound, either alone or as a part of a pharmaceutical composition, can be administered in a physiologically acceptable diluent in a pharmaceutically acceptable carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyldialkylammonium halides, and alkylpyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl .beta.-aminopropionates, and 2-alkylimidazoline quaternary ammonium salts, and (e) mixtures thereof.

The parenteral formulations typically contain from about 0.5% to about 50% by weight of the conjugate or compound in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

EXAMPLES

The following examples provide a description of methods for the preparation of the conjugates and compound of the present disclosure using polyoxazoline as an exemplary polymer and apomorphine as an exemplary compound comprising a catechol moiety. The polymer conjugates are illustrated as containing two different linkages of the compound to the polymer portion (i.e., for apomorphine, the compound is illustrated as linked to the polymer portion via a linkage between both the hydroxyl groups at the 10 and 11 positions) as a result of certain methods of synthesizing the compounds with the required linkage and blocking group. For example, in Example 4 apomorphine-10,11-[(4'-azidobutyrate)(isobutyrate)]hydrochloride is synthesized comprising a linking group and a isobutyrate blocking group, wherein the linking group is at position 10 and the blocking group is at position 11 of the apomorphine molecule in compound 3a (and reversed in compound 3b). Linking compounds 3a and 3b to the polymer portion (see Example 7) results in the apomorphine being linked to the polymer portion via the hydroxyl at both the 10 and 11 positions. However, if a particular form of a compound is desired (for example, one of 3a or 3b), then the compounds can be separated using convention techniques (for example, chromatography). The following examples also provide for methods of analysis of these conjugates, and measurements of hydrolysis rates of these conjugates in human plasma.

Materials

Apomorphine hydrochloride was obtained from Johnson Matthey. POZ 10p-Acid 20K and 4-azidobutyryl chloride was synthesized by Serina Therapeutics, Inc. Butyryl chloride, isobutyl chloride, benzoyl chloride, triethylamine (TEA) were purchased from Sigma-Aldrich. Trifluroacetic acid (TFA), hydrochloric acid (HCl), anhydrous sodium sulfate, dichloromethane (DCM), acetonitrile (ACN), and diethyl ether were purchased from EMD Millipore. L(+)-Ascorbic acid sodium salt, cupric sulfate pentahydrate ($CuSO_4·5H_2O$), and sodium chloride (NaCl) were purchased from Fluka. Dimethyl sulfoxide (DMSO) was purchased from Acros Organics. Ambersep M4195 (or Dowex M4195) was purchased from Supelco. The SNAP Ultra C18 30 g column and Isolera System for column purification were from Biotage.

Example 1—Synthesis of Apomorphine mono-(4'-azidobutyrate) hydrochloride

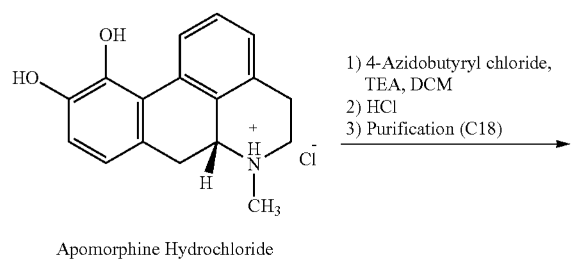

Apomorphine Hydrochloride

-continued

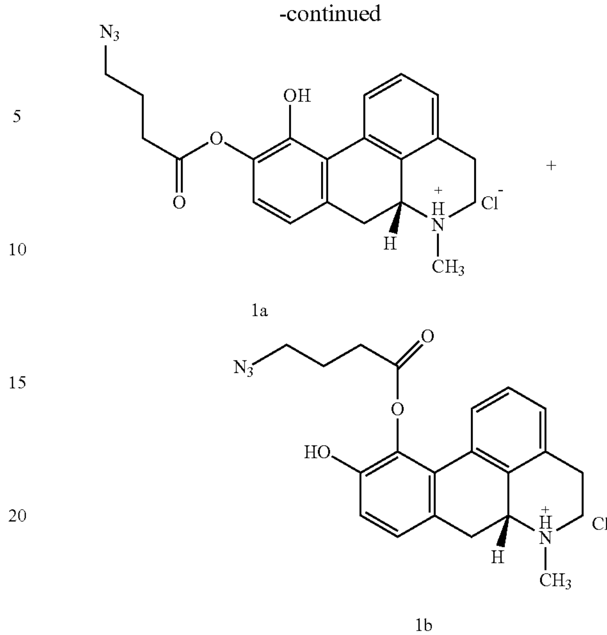

1a

1b

Apomorphine hydrochloride (4.00 gm, 12.72 mmol, 1 eq.) was weighed into a 500 mL RB flask with 385 mL DCM. Under argon, triethylamine (3.546 mL, 25.44 mmol, 2 eq.) was added, followed by addition of a solution of 4-azidobutyryl chloride (1.877 gm, 12.72 mmol, 1 eq.) in 15 mL DCM into the reaction mixture. The solution was allowed to stir at room temperature under argon for 30 minutes after which the solution was washed with 0.1 N HCl (1271 mL). Following phase separation, NaCl (147 gm) was added into the aqueous phase, which was extracted by DCM (3×200 mL). Following phase separation, the DCM phase was dried over anhydrous sodium sulfate (200 gm). After filtration to remove sodium sulfate, the filtrate was evaporated to dryness. The residue was further dried in vacuum, which afforded 2.90 gm of off-white crude product. Reversed phase HPLC analysis of the crude product showed 97.8% of apomorphine mono-(4'-azidobutyrate) hydrochloride. The crude product was purified with a Biotage SNAP Ultra C18 30 g column on a Biotage Isolera System using 2 mM HCl and ACN as mobile phases. Following column purification, ACN in the product fraction was evaporated, and NaCl was added to the remaining aqueous solution to make 15% brine. The solution was extracted with DCM (4×200 mL). The DCM phase was dried over anhydrous sodium sulfate (150 gm). After filtration, the filtrate was concentrated to dryness by rotary evaporation, and further dried in vacuum overnight, which afforded 2.65 gm of light grayish colored solid (1a+1b, 50% yield). Purity by HPLC was >99.9%.

Example 2—Synthesis of Apomorphine-10,11-[(4'-azidobutyrate)(butyrate)]hydrochloride 1a + 1b

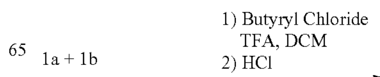

-continued

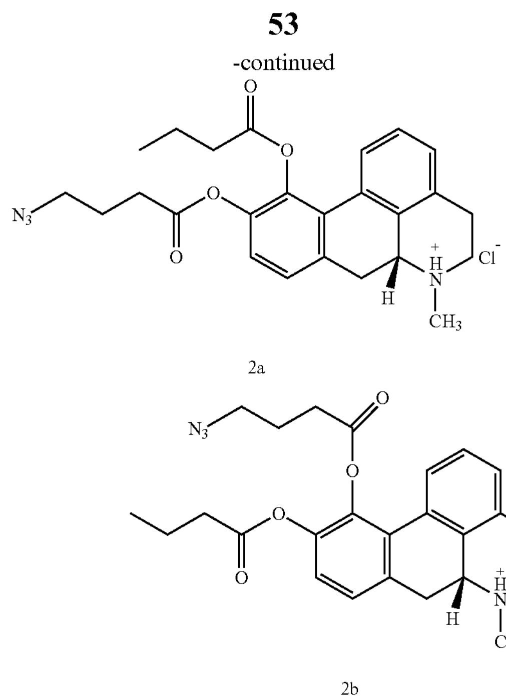

2a

2b

Apomorphine-(4'-azidobutyrate) hydrochloride (1a+1b, 0.40 gm, 0.964 mmol) was weighed into a 100 mL round bottom flask with anhydrous DCM (40 mL). Under argon, trifluoroacetic acid (4 mL) was added to the solution, followed by addition of butyryl chloride (1.00 mL, 9.64 mmol, 10 eq.). The solution was allowed to stir at room temperature under argon overnight. Reversed phase HPLC analysis of the reaction mixture indicated that the reaction went to completion. The solution was evaporated to dryness, the remaining syrup was dissolved in DCM (100 mL), washed with deionized water (200 mL), and then 0.1 N HCl (200 mL). The DCM phase was dried over anhydrous sodium sulfate (40 gm), and then filtered. The filtrate was evaporated to dryness. The residual was further dried in vacuum which afforded 0.58 gm amber colored wax-like solid (2a+2b).

Example 3—Synthesis of Apomorphine-10,11-[(4'-azidobutyrate)(isobutyrate)]hydrochloride

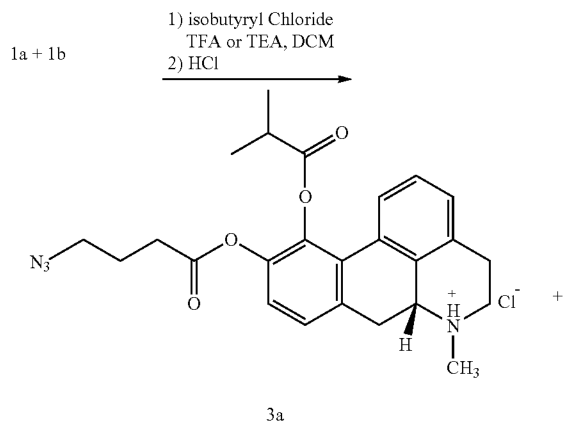

3a

-continued

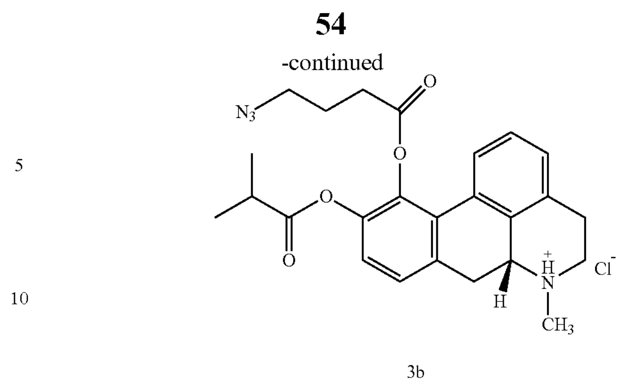

3b

Apomorphine-(4'-Azidobutyrate) hydrochloride (1a+1b, 0.10 gm, 0.241 mmol) was weighed into a 25 mL round bottom flask with anhydrous DCM (10 mL). Under argon, trifluoroacetic acid (1 mL) was added, followed by addition of isobutyryl chloride (0.25 mL, 2.41 mmol, 10 eq.). The solution was allowed to stir overnight at room temperature under argon then evaporated to dryness. The remaining syrup was dissolved in DCM (25 mL), which was washed with 0.1 N HCl (50 mL). The DCM phase was dried over anhydrous sodium sulfate (10 gm) and filtered. The filtrate was evaporated to dryness and further drying under vacuum, afforded 0.12 gm of amber residue (3a+3b). HPLC analysis of the product showed the purity to be 100%.

Example 4—Synthesis of Apomorphine-10,11-[(4'-azidobutyrate)(isobutyrate)]hydrochloride

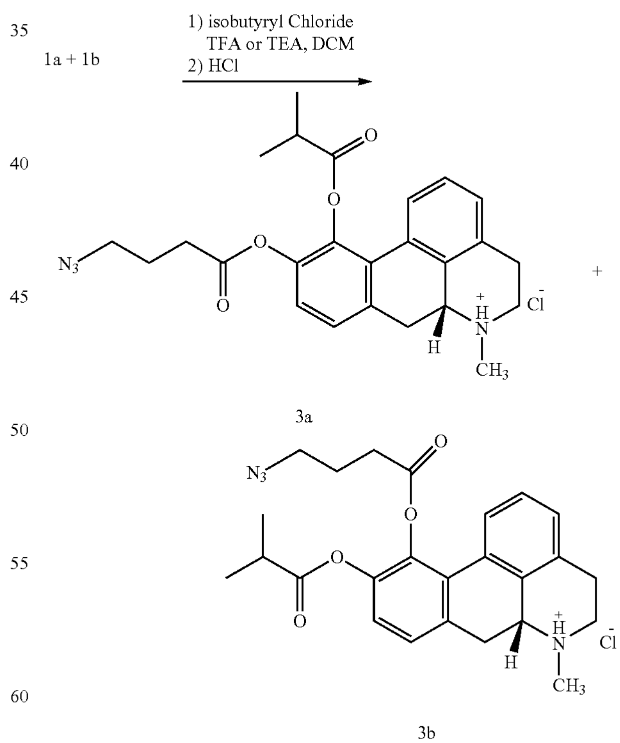

3a

3b

Apomorphine-(4'-azidobutyrate) hydrochloride (1a+1b, 0.50 gm, 1.205 mmol) was weighed into a 100 mL round bottom flask with anhydrous DCM (50 mL). Under argon, triethylamine (0.34 mL, 2.410 mmol, 2 eq.) was added, followed by addition of isobutyryl chloride (0.155 mL, 1.446 mmol, 1.2 eq.). The solution was allowed to stir overnight at room temperature under argon atmosphere. Subsequently, the solution was washed with 0.1 N HCl (145 mL) twice. The DCM phase was dried over anhydrous sodium sulfate (25 gm), and then filtered. The filtrate was evaporated to dryness. Further drying under vacuum afforded 0.49 gm of amber colored residual (3a+3b). HPLC analysis of the product showed a purity of 99.4%.

Example 5—Synthesis of Apomorphine-10,11-[(4'-azidobutyrate)(benzoate)]hydrochloride

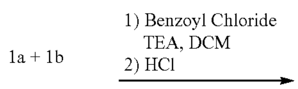

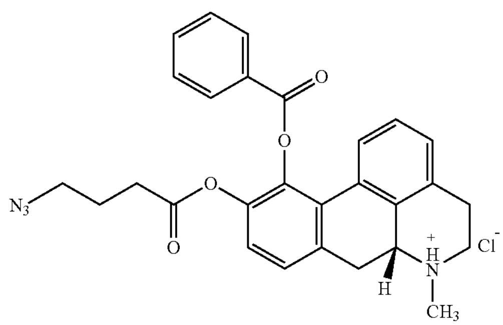

+

4a

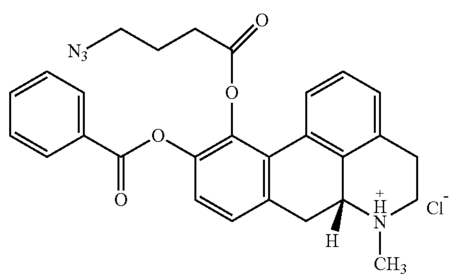

4b

Apomorphine-(4'-azidobutyrate) hydrochloride (1a+1b, 0.50 gm, 1.205 mmol) was weighed into a 100 mL round bottom flask with anhydrous DCM (50 mL). Under argon, triethylamine (0.34 mL, 2.410 mmol, 2 eq.) was added, followed by addition of benzoyl chloride (0.168 mL, 1.446 mmol, 1.2 eq.). The solution was allowed to stir overnight at room temperature under argon. Following 30 minutes of reaction, the solution was washed with 0.1 N HCl (145 mL) twice. The DCM phase was dried over anhydrous sodium sulfate (25 gm), and then filtered. The filtrate was evaporated to dryness. Further drying under vacuum afforded 0.55 gm amber colored residual (4a+4b). HPLC analysis of the product showed a purity of 97.7%.

Example 6—Synthesis of POZ10p20k[Apo(4-butanoate)(4-triazolebutanoate)]$_{10}$ by Click Reaction (5)

Apomorphine-10,11-[(4'-azidobutyrate)(butyrate)] hydrochloride (2a+2b, 0.10 gm, 0.21 mmol, 11.6 eq.) and POZ 10p-Acid 20K (0.37 gm, 0.018 mmol, 1 eq.) was dissolved in DMSO (10 mL) and deionized water (5 mL) in a 50 mL round bottom flask. Under argon, Na ascorbate (0.017 gm, 0.085 mmol, 4.64 eq.) was then added to the flask, followed by immediate addition of CuSO4·5H2O (0.021 gm, 0.085 mmol, 4.64 eq.). The solution was then stirred overnight at room temperature under argon. The reaction mixture was diluted with 5 mM HCl with 10 wt % NaCl (150 mL), which was extracted twice by DCM (50 mL). The DCM phase was evaporated to dryness, and the residual was dissolved in 2 mM HCl (10 mL). Copper in the aqueous solution was removed by passing the aqueous solution through Ambersep M4195 media packed in a glass column. The column was eluted with 2 mM HCl (50 mL). NaCl (9 gm) was added into the collected eluent (60 mL), and the cloudy solution was extracted with DCM (2×50 mL). Following phase separation, the DCM phase was dried over anhydrous sodium sulfate (30 gm). Following filtration to remove sodium sulfate, the filtrate was concentrated to near dryness by rotary evaporation. The residual was dissolved in DCM (4 mL), followed by precipitation in diethyl ether (60 mL). The precipitate was collected after filtration, and dried in vacuum, which afforded 0.39 gm of white powder (POZ10p20k[Apo(4-butanoate)(4-triazolebutanoate)]$_{10}$, 5; POZ-Apomorphine A).

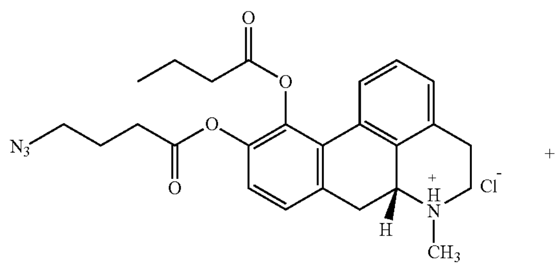

+

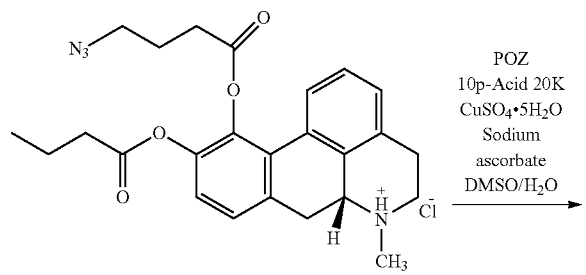

-continued

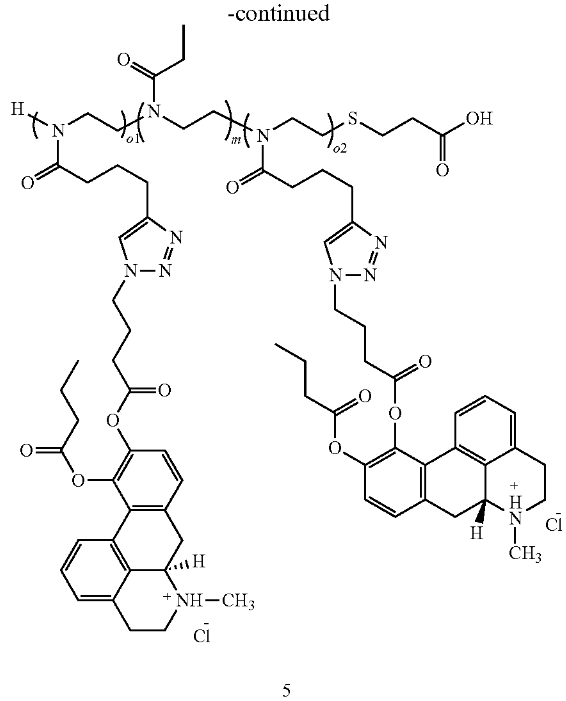

5

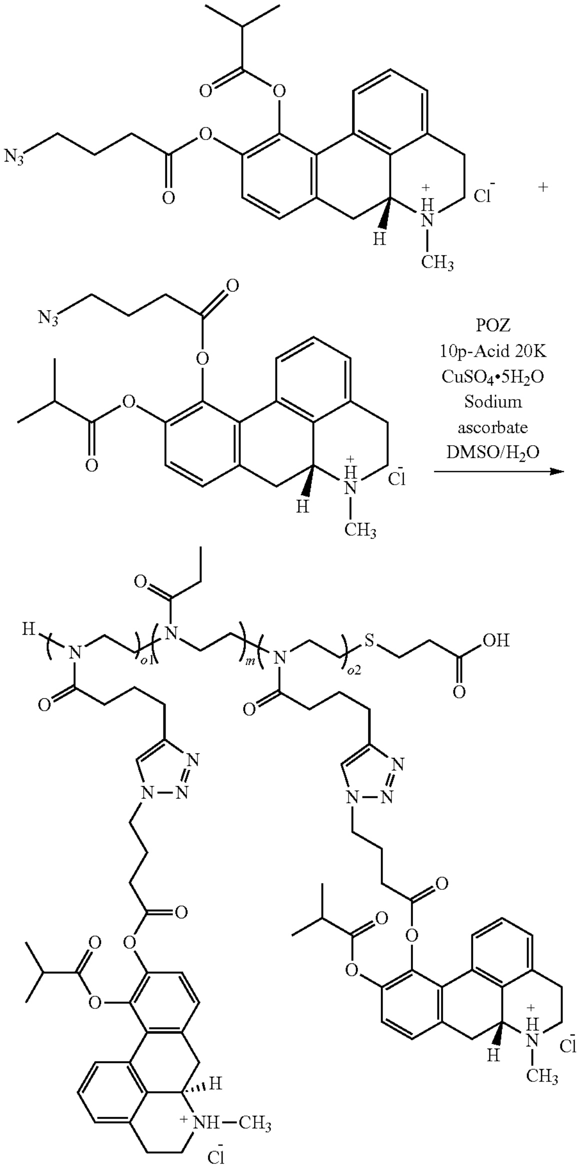

6

Example 7—Synthesis of POZ10p20k[Apo(2-methylpropanoate)(4-triazolebutanoate)]$_{10}$ by Click Reaction (6)

Apomorphine-10,11-[(4'-azidobutyrate)(isobutyrate)] hydrochloride (3a+3b, 0.086 gm, 0.178 mmol, 11.6 eq.) and POZ 10p-Acid 20K (0.31 gm, 0.015 mmol, 1 eq.) was dissolved in DMSO (8 mL) and deionized water (4 ml) in a 50 mL round bottom flask. Under argon, Na ascorbate (0.014 gm, 0.071 mmol, 4.64 eq.) was then added to the flask followed by immediate addition of CuSO4·5H2O (0.018 gm, 0.071 mmol, 4.64 eq.). The solution was then stirred overnight at room temperature under argon. The reaction mixture was diluted with 5 mM HCl with 10 wt % NaCl (150 mL), which was extracted twice with DCM (50 mL). The DCM phase was evaporated to dryness, and the residual was dissolved in 2 mM HCl (10 mL). Copper in the aqueous solution was removed by passing the aqueous solution through Ambersep M4195 media packed in a glass column. The column was eluted with 2 mM HCl (40 mL). NaCl (7.5 gm) was added into the collected eluent (50 mL), and the cloudy solution was extracted with DCM (2×50 mL). Following phase separation, the DCM phase was dried over anhydrous sodium sulfate (30 gm). Following filtration to remove sodium sulfate, the filtrate was concentrated to near dryness by rotary evaporation. The residual was dissolved in DCM (4 mL), followed by precipitation in diethyl ether (50 mL). The precipitate was collected after filtration, and dried in vacuum, which afforded 0.36 gm of white powder (POZ10p20k[Apo(2-methylpropanoate)(4-triazolebutanoate)]$_{10}$, 6; POZ-Apomorphine B).

Example 8—Synthesis of POZ10p20k[Apo(4-benzoate)(4-triazolebutanoate)]$_{10}$ by Click Reaction (7)

Apomorphine-10,11-[(4'-azidobutyrate)(benzoate)] hydrochloride (4a+4b, 0.129 gm, 0.238 mmol, 11.6 eq.) and POZ 10p-Acid 20K (0.42 gm, 0.021 mmol, 1 eq.) was dissolved in DMSO (10 mL) and deionized water (5 mL) in a 50 mL round bottom flask. Under argon, Na ascorbate (0.019 gm, 0.095 mmol, 4.64 eq.) was then added to the flask, followed by immediate addition of CuSO4·5H2O (0.024 gm, 0.095 mmol, 4.64 eq.). The solution was then stirred overnight at room temperature under argon. The reaction mixture was diluted by 5 mM HCl with 10 wt % NaCl (150 mL), which was extracted twice by DCM (50 mL). The DCM phase was evaporated to dryness, and the residual was dissolved in 2 mM HCl (10 mL). Copper in the aqueous solution was removed by passing it through Ambersep M4195 media packed in a glass column. The column was eluted with 2 mM HCl. NaCl (11.3 gm) was added into the collected eluent (75 mL), and the cloudy solution was extracted with DCM (2×50 mL). Following phase separation, the DCM phase was dried over anhydrous sodium sulfate (50 gm). Following filtration to remove sodium sulfate, the filtrate was concentrated to near dryness by rotary evaporation. The residual was dissolved in DCM (5 mL), followed by precipitation in diethyl ether (50 mL). The precipitate was collected after filtration, and dried in vacuum, which afforded 0.5 gm of white powder (POZ10p20k[Apo(4-benzoate)(4-triazolebutanoate)]$_{10}$, 7; POZ-Apomorphine C).

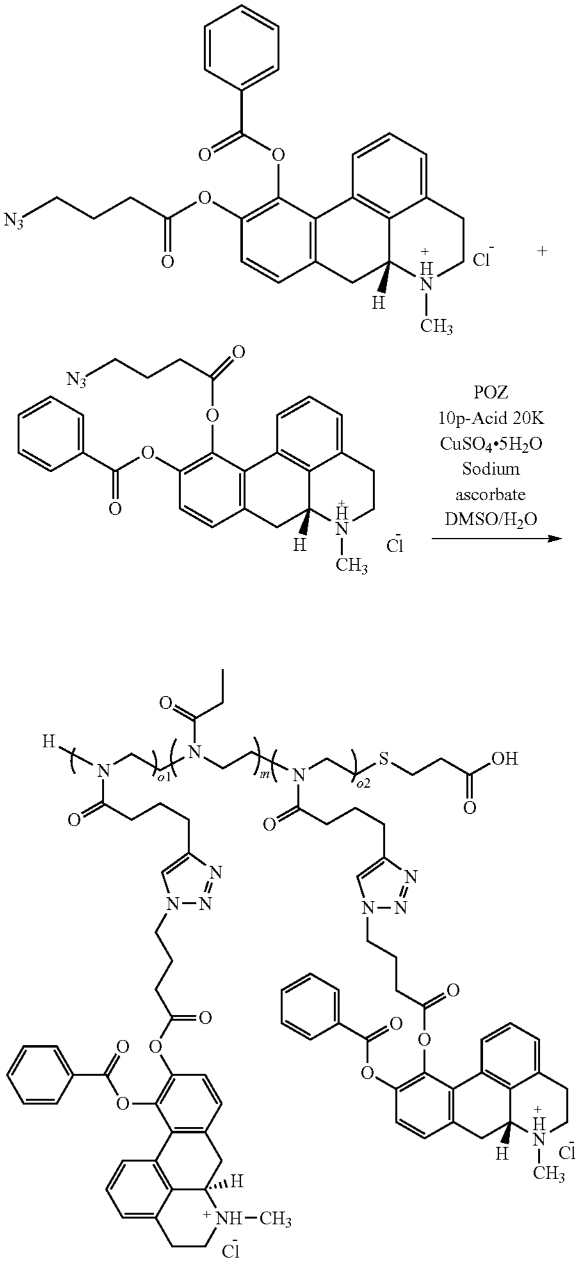

7

Example 9—Synthesis of POZ10p20k[Apo(4-triazole-4-butanoate)]$_{10}$ by Click Reaction (8)

Apomorphine-(4'-azidobutyrate) hydrochloride (1a+1b, 0.069 gm, 0.166 mmol, 11.3 eq.) and POZ 10p-Acid 20K (0.30 gm, 0.0146 mmol, 1 eq.) was dissolved in deionized water (10 mL) in a 50 mL round bottom flask. Under argon atmosphere, Na Ascorbate (0.013 gm, 0.066 mmol, 4.54 eq.) was then added to the flask, followed by immediate addition of $CuSO_4 \cdot 5H_2O$ (0.017 gm, 0.066 mmol, 4.54 eq.). The solution was then stirred overnight at room temperature under argon atmosphere. Copper in the aqueous solution was removed by passing the aqueous solution through Ambersep M4195 media packed in a glass column. The column was eluted with 2 mM HCl. NaCl (7.5 gm) was added into the collected eluent (75 mL), and the cloudy solution was extracted with DCM (4×20 mL). Following phase separation, the DCM phase was dried over anhydrous sodium sulfate (30 gm). Following filtration to remove sodium sulfate, the filtrate was concentrated to near dryness by rotary evaporation. The residual was dissolved in DCM (5 mL), followed by precipitation in diethyl ether (60 mL). The precipitate was collected after filtration, and dried in vacuum, which afforded 0.3 gm of white powder (POZ10p20k[Apo(4-triazole-4-butanoate)]$_{10}$, 8; POZ-Apomorphine F).

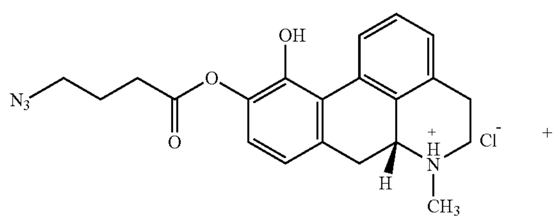

1a

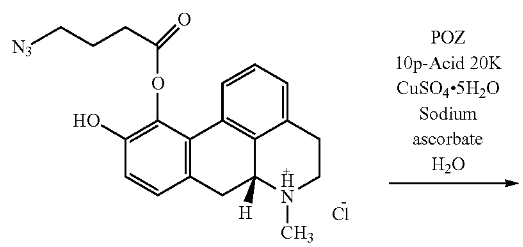

1b

-continued

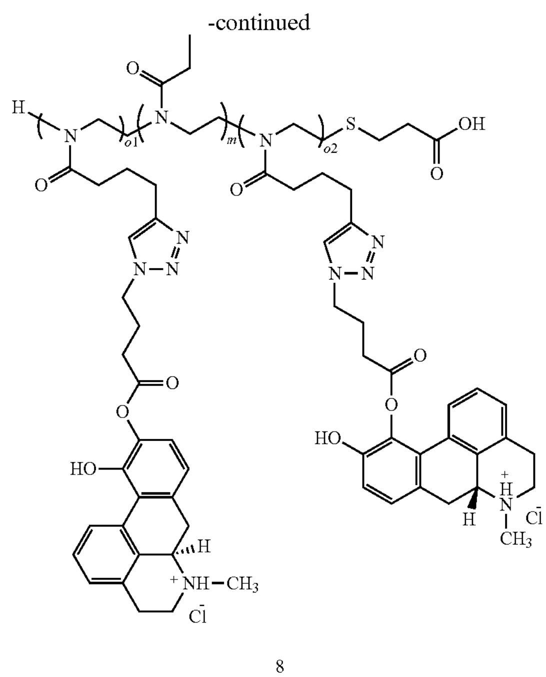

8

Example 10—Synthesis of Apomorphine-10,11-[(4'-azidobutyrate)(acetate)]hydrochloride

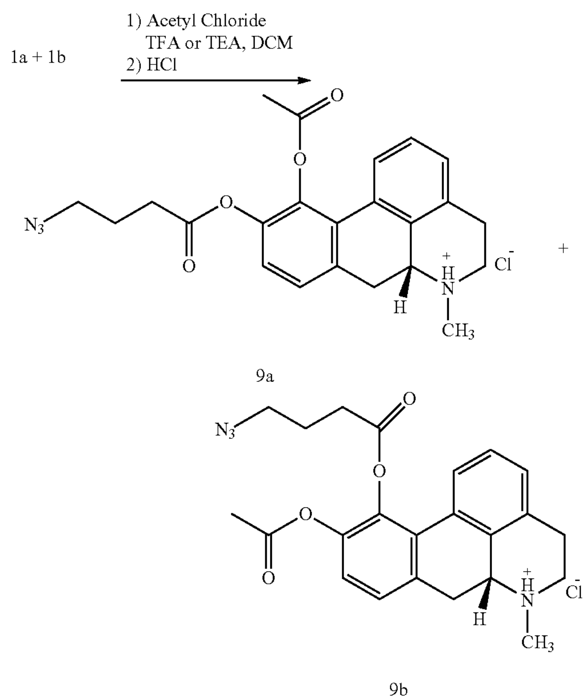

9a

9b

Apomorphine-(4'-azidobutyrate) hydrochloride (1a+1b, 0.18 gm, 0.434 mmol) was weighed into a 50 mL round bottom flask with anhydrous DCM (20 mL). Under argon, triethylamine (0.12 mL, 0.868 mmol, 2 eq.) was added, followed by addition of acetyl chloride (0.035 mL, 0.477 mmol, 1.1 eq.). The solution was allowed to stir for thirty minutes at room temperature under argon atmosphere. Subsequently, the solution was washed with 0.1 N HCl (87 mL) twice. The DCM phase was dried over anhydrous sodium sulfate (10 gm), and then filtered. The filtrate was evaporated to dryness. Further drying under vacuum afforded 0.13 gm of off white colored residual (9a+9b). HPLC analysis of the product showed a purity of 99.8%.

Example 11—Synthesis of Apomorphine-10,11-[(4'-azidobutyrate)(propionate)]hydrochloride

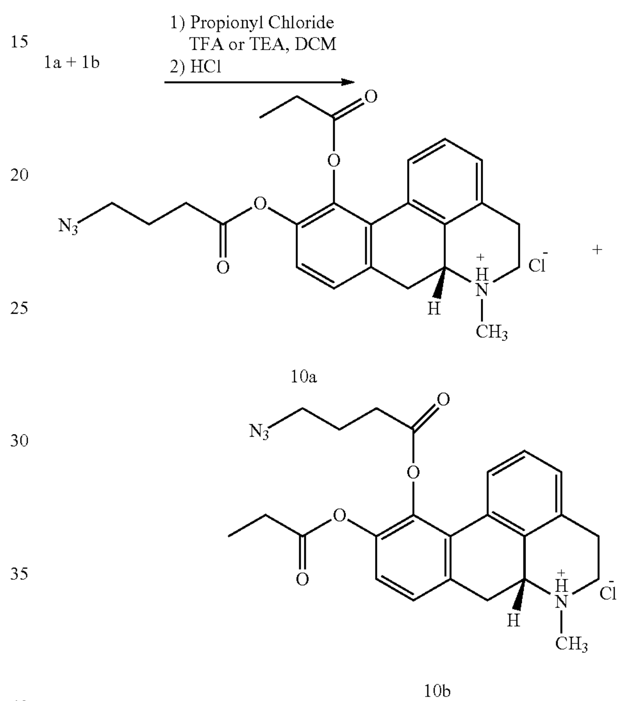

10a

10b

Apomorphine-(4'-azidobutyrate) hydrochloride (1a+1b, 0.20 gm, 0.482 mmol) was weighed into a 50 mL round bottom flask with anhydrous DCM (20 mL). Under argon, triethylamine (0.13 mL, 0.964 mmol, 2 eq.) was added, followed by addition of propionyl chloride (0.047 mL, 0.530 mmol, 1.1 eq.). The solution was allowed to stir for thirty minutes at room temperature under argon atmosphere. Subsequently, the solution was washed with 0.1 N HCl (96 mL) twice. The DCM phase was dried over anhydrous sodium sulfate (10 gm), and then filtered. The filtrate was evaporated to dryness. Further drying under vacuum afforded 0.19 gm of off white colored residual (6a+6b). HPLC analysis of the product showed a purity of 98.8%.

Example 12—Synthesis of POZ10p20k[Apo(acetate)(4-triazolebutanoate)]$_{10}$ by Click Reaction (11)

Apomorphine-10,11-[(4'-azidobutyrate)(acetate)] hydrochloride (9a+9b, 0.13 gm, 0.27 mmol, 11.6 eq.) and POZ 10p-Acid 20K (0.48 gm, 0.024 mmol, 1 eq.) was dissolved in DMSO (8 mL) and deionized water (4 mL) in a 50 mL round bottom flask. Under argon, Na ascorbate (0.022 gm, 0.110 mmol, 4.66 eq.) was then added to the flask, followed by immediate addition of $CuSO4 \cdot 5H_2O$ (0.027 gm, 0.110 mmol, 4.66 eq.). The solution was then stirred overnight at room temperature under argon. The reaction mixture was diluted with 5 mM HCl with 10 wt % NaCl (84 mL), which was extracted twice by DCM (30 mL). The DCM phase was evaporated to dryness, and the residual was dissolved in 2 mM HCl (10 mL). Copper in the aqueous solution was removed by passing the aqueous solution through Ambersep M4195 media packed in a glass column. The column was eluted with 2 mM HCl (90 mL). NaCl (10 gm) was added into the collected eluent (100 mL), and the cloudy solution was extracted with DCM (2×40 mL). Following phase separation, the DCM phase was dried over anhydrous sodium sulfate (40 gm). Following filtration to remove sodium sulfate, the filtrate was concentrated to near dryness by rotary evaporation. The residual was dissolved in DCM (5 mL), followed by precipitation in diethyl ether (55 mL). The precipitate was collected after filtration, and dried in vacuum, which afforded 0.44 gm of white powder (POZ10p20k[Apo(acetate)(4-triazolebutanoate)]$_{10}$, 11; POZ-Apomorphine D).

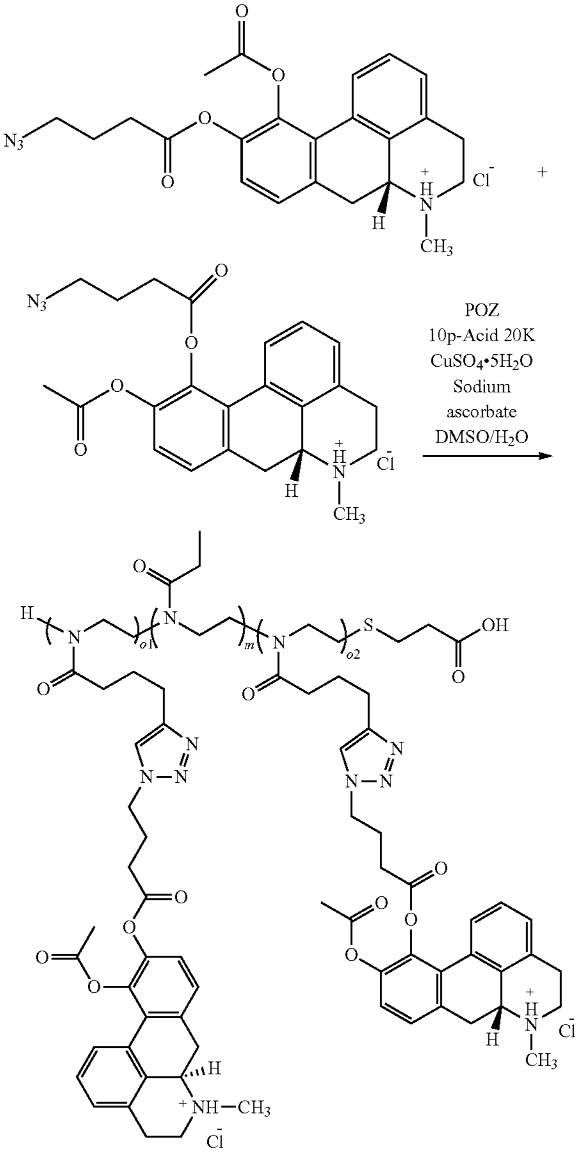

11

Example 13—Synthesis of POZ10p20k[Apo(propionate)(4-triazolebutanoate)]$_{10}$ by Click Reaction (12)

Apomorphine-10,11-[(4'-azidobutyrate)(propionate)] hydrochloride (10a+10b, 0.19 gm, 0.39 mmol, 11.7 eq.) and POZ 10p-Acid 20K (0.68 gm, 0.033 mmol, 1 eq.) was dissolved in DMSO (11 mL) and deionized water (5.5 mL) in a 50 mL round bottom flask. Under argon, Na ascorbate (0.031 gm, 0.156 mmol, 4.66 eq.) was then added to the flask, followed by immediate addition of CuSO4·$5H_2O$ (0.039 gm, 0.156 mmol, 4.66 eq.). The solution was then stirred overnight at room temperature under argon. The reaction mixture was diluted with 5 mM HCl with 10 wt % NaCl (120 mL), which was extracted twice by DCM (40 mL). The DCM phase was evaporated to dryness, and the residual was dissolved in 2 mM HCl (14 mL). Copper in the aqueous solution was removed by passing the aqueous solution through Ambersep M4195 media packed in a glass column. The column was eluted with 2 mM HCl. NaCl (11 gm) was added into the collected eluent (110 mL), and the cloudy solution was extracted with DCM (2×40 mL). Following phase separation, the DCM phase was dried over anhydrous sodium sulfate (40 gm). Following filtration to remove sodium sulfate, the filtrate was concentrated to near dryness by rotary evaporation. The residual was dissolved in DCM (7 mL), followed by precipitation in diethyl ether (76 mL). The precipitate was collected after filtration, and dried in vacuum, which afforded 0.70 gm of white powder (POZ10p20k[Apo(propionate)(4-triazolebutanoate)]$_{10}$, 12; POZ-Apomorphine E).

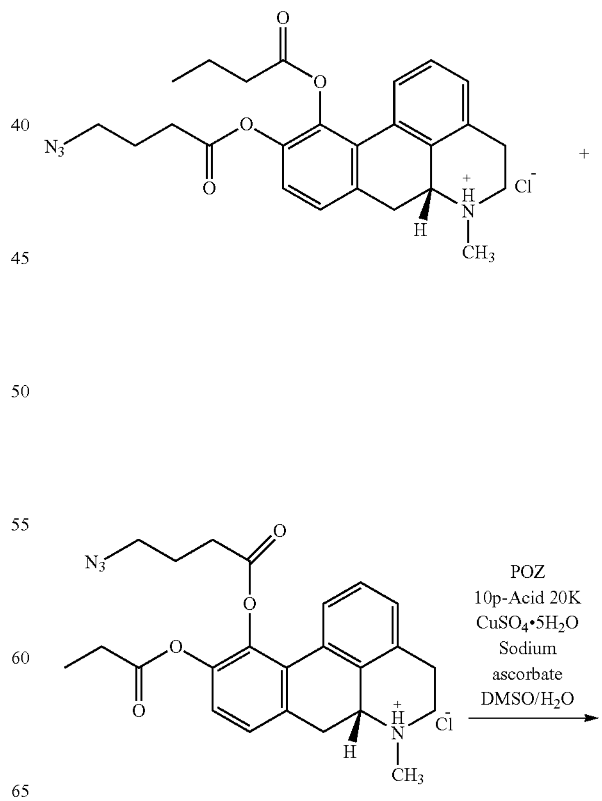

-continued

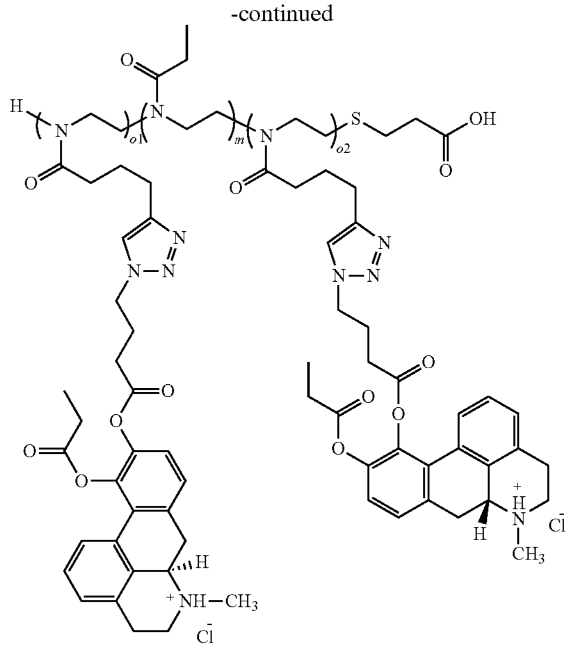

12

Example 14—Synthesis of Apomorphine-10,11-[(4'-azidobutyrate)(mono-ethyl succinate)] hydrochloride

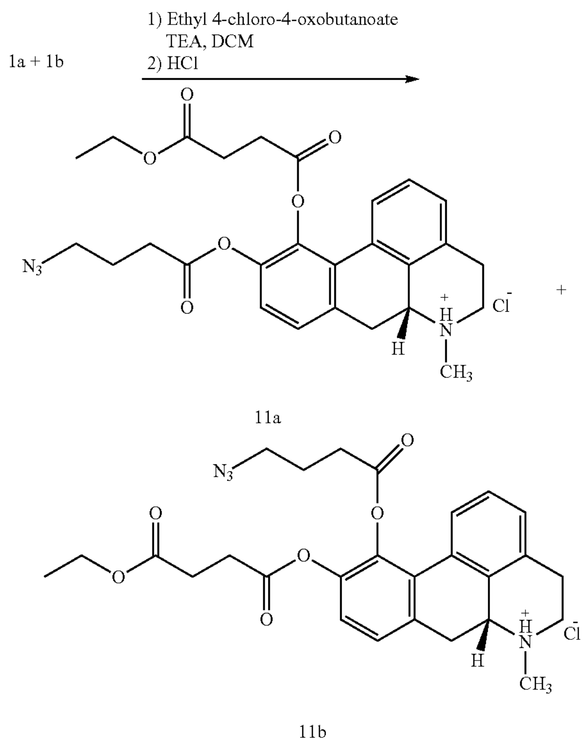

11a

11b

Apomorphine-(4'-azidobutyrate) hydrochloride (1a+1b, 0.60 gm, 1.446 mmol) was weighed into a 100 mL round bottom flask with anhydrous DCM (60 mL). Under argon, triethylamine (0.40 mL, 2.892 mmol, 2 eq.) was added, followed by addition of ethyl 4-chloro-4-oxobutanoate (0.31 gm, 1.591 mmol, 1.1 eq.) in 2 ml of anhydrous DCM. The solution was allowed to stir overnight at room temperature under argon. Following 30 minutes of reaction, the solution was washed with 0.1 N HCl (289 mL) twice. The DCM phase was dried over anhydrous sodium sulfate (30 gm), and filtered. The filtrate was evaporated to dryness and drying in vacuum afforded 0.72 gm solid (11a+11b). HPLC analysis of the product showed a purity of 99.8%.

Example 15—Synthesis of POZ10p20k[Apo (4'-triazolebutanoate)(mono-ethyl succinate)]$_{10}$ by Click Reaction (13)

Apomorphine-10,11-[(4'-azidobutyrate)(mono-ethyl succinate)] hydrochloride (5a+5b, 0.34 gm, 0.631 mmol, 11.7 eq.) and POZ 10p-Acid 20K (1.1 gm, 0.054 mmol, 1 eq.) was dissolved in DMS0 (18 mL) and deionized water (9 mL) in a 50 mL round bottom flask. Under argon, Na ascorbate (0.05 gm, 0.253 mmol, 4.66 eq.) was then added to the flask, followed by immediate addition of $CuSO_4 \cdot 5H_2O$ (0.063 gm, 0.253 mmol, 4.66 eq.). The solution was then stirred overnight at room temperature under argon. The reaction mixture was diluted with 5 mM HCl with 10 wt % NaCl (195 mL), which was extracted twice by DCM (70 mL). The DCM phase was evaporated to dryness, and the residual was dissolved in 2 mM HCl (22 mL). Copper in the aqueous solution was removed by passing the aqueous solution through Ambersep M4195 media packed in a glass column. The column was eluted with 2 mM HCl (160 mL). NaCl (18 gm) was added into the collected eluent (182 mL), and the cloudy solution was extracted with DCM (2×100 mL). Following phase separation, the DCM phase was dried over anhydrous sodium sulfate (30 gm). Following filtration to remove sodium sulfate, the filtrate was concentrated to near dryness by rotary evaporation. The residual was dissolved in DCM (12 mL), followed by precipitation in diethyl ether (124 mL). The precipitate was collected after filtration, and dried in vacuum, which afforded 1.16 gm of white powder (POZ10p20k[Apo (4'-triazolebutanoate)(mono-ethyl succinate]$_{10}$, 13, POZ-Apomorphine G).

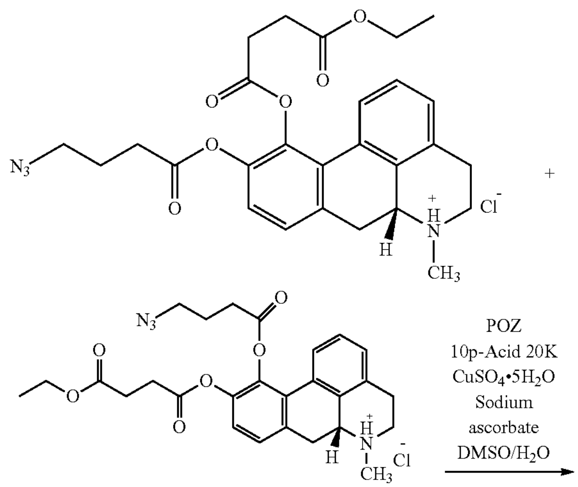

-continued

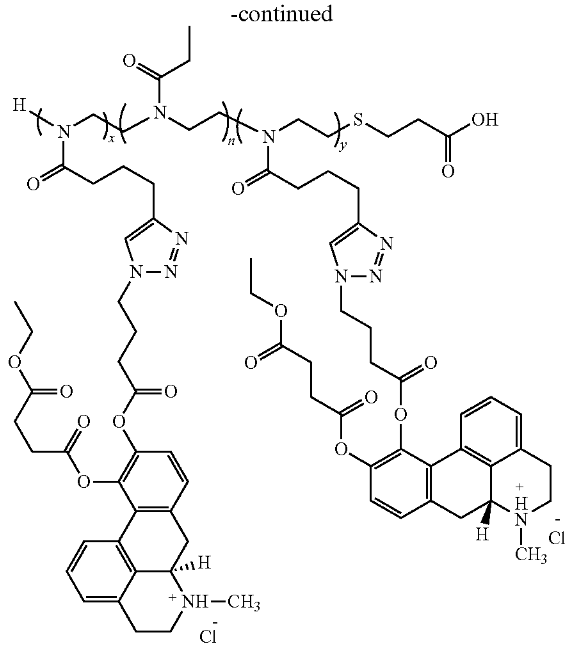

13

Example 16—Exemplary Synthesis of Random H-[$(Ptyn)_{10}(EOZ)_{190}$]-T-$CO_2$H (POZ10p20k)

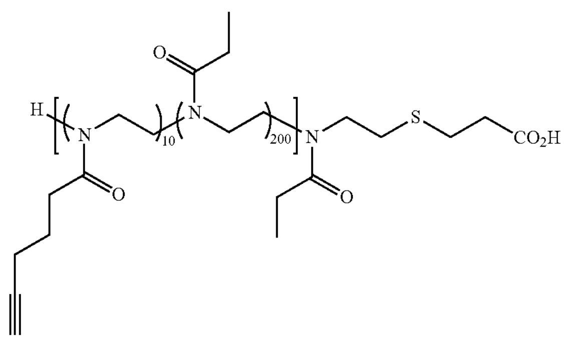

The synthesis of POZ polymers with various pendent groups is described in U.S. Pat. Nos. 8,110,651 and 8,101,706, each of which is incorporated herein by reference for such teachings. In a specific embodiment, the synthesis of H-[$(Ptyn)_{10}(EOZ)_{190}$]-T-$CO_2$H is provided although other POZ polymers with different molecular weights, different initiating and terminating groups as well as different groups at the pendent position may be produced by the same methods. In addition, block co-polymers may be produced in addition to the random co-polymers described in this Example. Methods for producing random and block co-polymers are described in U.S. Pat. Nos. 8,110,651 and 8,101,706, each of which is incorporated herein by reference for such teachings.

For the synthesis of H-[$(Ptyn)_{10}(EOZ)_{190}$]-T-$CO_2$H, triflic acid (HOTf, 173.3 μL, 1.96 mmol) was added to a solution of 2-pentynyl-2-oxazoline (PtynOZ, 3.76 g, 27.4 mmol, 14 eq) and 2-ethyl-2-oxazoline (EOZ, 46.61 g, 470.2 mmol, 240 eq) in chlorobenzene (124 mL). After stirring for 5 minutes at room temperature, the mixture was heated to 80° C. for 10 hours followed by cooling to room temperature. In a separate flask, the terminating reagent was prepared by the dropwise addition of methyl 3-mercaptopropionate (1.23 mL, 0.0114 mol) into a suspension of sodium hydride (60% in mineral oil, 0.272 g, 0.0068 mol) in chlorobenzene (34 mL). This mixture was stirred for 7 hours, before the solution of living polymer of H-$(Ptyn)_{10}(EOZ)_{200}^+$ was added. The resulting mixture was then stirred for 18 hours. The solvent was removed by rotary evaporation to yield a white residue. This residue was dissolved in water and the pH adjusted to 12.0. The resulting aqueous solution was purified by ion-exchange chromatography using DEAE Sepharose FF. The aqueous solution was saturated with NaCl (15% w/w) and extracted with dichloromethane. The combined organic phases were dried over anhydrous sodium sulfate, filtered, and concentrated using a rotary evaporator. The residue was precipitated by adding the dichloromethane concentrate to diethyl ether. The precipitated material was collected and dried in vacuo to give 22.8 g of desired product as a white powder (50% yield).

$^1$H NMR (Varian, 500 MHz, 10 mg/mL $CDCl_3$) showed the usual backbone peaks at 1.13 ppm (m, 3H, $CH_3CH_2CO$—); 2.32 ppm (m) and 2.41 (s) (total area 2H, $CH_3CH_2CO$—); and 3.47 ppm (m, 4H, —$NCH_2CH_2N$—). The terminal group peaks appear at 2.63 ppm (m, 2H, —$SCH_2CH_2CO_2H$), 2.74 ppm (m, 2H, —$CH_2SCH_2CH_2CO_2H$), and 2.85 ppm (m, 2H, —$SCH_2CH_2CO_2H$). The pendent pentynyl group peaks appear at 1.85 ppm (m, 2H, —$CH_2CH_2C$═CH) and 2.03 ppm (br s, 1H, —$CH_2CH_2C$≡CH). The number of pendent, Ptyn, groups were determined as 8.5 by comparing the integrations of terminal acetylene proton and polymer backbone protons. GPC gave Mn=19,500 Da and Mp=20,800 Da with PDI of 1.07.

Example 17—Hydrolysis of POZ20K10p Mono and Di Esters of Apomorphine in Human Plasma at 37° C.

Female human plasma was received in frozen tubes (BioIVT) and thawed in a 37° C. water bath and mixed gently by inverting several times. The tube was then placed in an ice-bath until ready for use. The following POZ-Apomorphine conjugates were tested in this Example: POZ-Apomorphine A (Example 6; drug loading 10.1 wt %), POZ-Apomorphine B (Example 7; drug loading 10.3 wt %), POZ-Apomorphine C (Example 8; drug loading 12.0 wt %), POZ-Apomorphine D (Example 12, drug loading 10.2%), POZ-Apomorphine E (Example 13, drug loading 10.2%), POZ-Apomorphine F (Example 9; drug loading 14.2 wt %) and POZ-Apomorphine G (Example 15; drug loading 10.7 wt %).

About 50 mg of each POZ-Apomorphine conjugate was weighed into a 5 mL volumetric flask and dissolved in 5% dextrose solution. In a biological safety laminar flow hood, 300 μL of the solution was added to 3 mL of chilled female human plasma. This was done in triplicate. After mixing the contents in the tube by gently inverting the tube several times, an Eppendorf pipette was used to aliquot (200 μL) of the plasma solution into separate microcentrifuge tubes with screw caps, and the samples were placed in a horizontal shaking water bath and incubated at 37° C.

At each time point, a tube of the plasma solution was quenched with 1000 μL of 0.10% trifluoroacetic acid (TFA) in acetonitrile (ACN). The solution was vortexed to extract the POZ-Apomorphine conjugate from the precipitated protein. After centrifuging for 5 min at 14000 RPM, 500 μL of the supernatant was removed an added to 500 μL 0.10% TFA in purified water ($H_2O$) and the mixture was then transferred into a HPLC vial.

The mixture was analyzed by the following HPLC method: Agilent 1260 Diode array HPLC with a Zorbax 300SB C—8 Column (5 mm×4.6×150 mm). Mobile Phase A: 0.1% TFA in $H_2O$; Mobile Phase B: 0.10% TFA in ACN; Gradient: 0.0-7.5 min 32% B, 7.5-10.5 min 75% B; Run Time: 12 min; Post Time: 3 min; Flow Rate 1.8 mL/min; Injection Volume: 100 μL; UV λmax: 274 nm.

A calibration curve (concentration vs. peak area) of POZ20K10p-apomorphine in 5% dextrose, was created. The concentration of conjugate at each time point was calculated by integrating the area of the conjugate peak at a retention time of 10.8 minutes.

The hydrolysis rate of apomorphine from each of the POZ-Apomorphine conjugates was calculated using the rate of disappearance of the conjugate and is shown FIG. 1. The values are normalized to % released using the drug loading % for each compound. As shown in FIG. 1, the half-life of POZ-Apomorphine F (which lacks a blocking group on the second phenolic hydroxyl) was calculated to be approximately 6 minutes. The addition of the blocking group on the second phenolic hydroxyl increased the half-life of the POZ-Apomorphine conjugates A, B, C, D, and E in a manner that was dependent on the structure of the blocking group. The half-lives of each conjugate were as follows: 2 h (POZ-Apomorphine D); 6 h (POZ-Apomorphine E); 8 h (POZ-Apomorphine G); 9 h (POZ-Apomorphine A); 20 h (POZ-Apomorphine B), and 66 h (POZ-Apomorphine C). The in-vitro release half-lives are longer for benzoate>methylpropanoate>butanoate>ethylsuccinate>propionate>acetate>non-capped mono ester. FIG. 1 clearly shows the release rate of apomorphine from the described POZ conjugates is dependent on the structure of the blocking group on the second phenolic hydroxyl, allowing the rate of release (a release profile) to be selected based on the selection of the blocking group (the structure of the blocking group) on the second phenolic hydroxyl of the catechol moiety of apomorphine. Such a result is surprising and unexpected.

Example 18—Pharmacokinetic Study of POZ-Apomorphine Conjugates and Unconjugated, Free Apomorphine An in-vivo pharmacokinetic study of apomorphine HCl (hemi-hydrate) and POZ-apomorphine conjugates of the present disclosure was conducted in primates to determine the free plasma apomorphine levels (all test articles) and total (for POZ-Apomorphine conjugates) plasma apomorphine levels as well as dermal reactions to each of the test articles after a single subcutaneous (SC) infusion (apomorphine HCl) and single SC injection (POZ-Apomorphine conjugates).

POZ-Apomorphine Conjugates

The POZ-Apomorphine conjugates used in this study are those described in Example 6 (POZ-Apomorphine A) and Example 7 (POZ-Apomorphine B).

Dosing

Non-naïve female cynomolgus monkeys were used in the study. The animals had a minimum of 4 weeks since the last treatment of drug in a previous study. One animal, C3503, had an 18-day washout period. They were assigned to three groups with 3 animals per group. Animals in Groups 1 received a single 12 h SC infusion of apomorphine HCl at a dose of 1.5 mg/kg. Animals in groups 2 and 3 received a single SC injection of the POZ-Apomorphine A and POZ-Apomorphine B conjugates at a dose of 1.5 mg/kg (based on apomorphine equivalents). The dosing schedule is as indicated in Table 1.

TABLE 1

| | Treatment | | | | |
|---|---|---|---|---|---|
| Group No[1] | Test Article | Dose (mg/kg)[2] | Dose Vol (ml/kg) | Vehicle | Route |
| 1 | Apomorphine HCl ½$H_2O$ | 1.5 | 0.8 | D5W | SC[3] |
| 2 | POZ apomorphine A | 1.5 | 0.2 | D5W | SC[4] |
| 3 | POZ apomorphine B | 1.5 | 0.2 | D5W | SC[4] |

[1]for all groups, n = 3
[2]based on active drug
[3]12 h slow infusion
[4]single injection The test articles were dosed subcutaneously (as described in Table 1) in the right shoulder of each monkey. Animals were observed for signs of ill health, general adverse reactions, inflammation at the sites of injection, and mortality to treatment as described herein.

Blood Sampling and Plasma Preparation

All animals were dosed at 0 h. Blood samples from Group 1 were collected at 1, 2, 4, 8, 12, 18, 24 and 48 hrs post-dose. Blood samples from Groups 2 and 3 were collected at 1, 3, 6, 12, 24, 48, 72, 120, 168 and 240 hrs post-dose.

Approximately 1.0 mL of blood was collected from each animal via cephalic vein into a tube containing anti-coagulant mixture NaF/$Na_2$EDTA (25 μL, containing 60 mg/mL NaF and 120 mg/mL $Na_2$EDTA) and 0.5 M sodium ascorbate solution (100 μL) on wet ice and processed to provide plasma. The tubes were mixed by gentle wrist rotation and placed in an ice-bath. Samples were centrifuged (3,000 RPM for 15 minutes at 2 to 8° C.) within 20 minutes of collection. For all groups, at least 500 μL of plasma was obtained at each time point. Two aliquots of at least 250 μL were obtained and treated as follows:

Aliquot 1 (used for free drug analysis, Group 1, 2 and 3). Plasma was transferred to a sample tube and gently mixed. After mixing, the samples were frozen and stored at −70 to −80° C. before transfer to bioanalytical laboratory for determination of free drug concentration.

Aliquot 2 (used for total drug analysis, Group 2 and 3 only). Plasma was transferred to a sample tube and gently mixed. After mixing, the samples were frozen and stored at −70 to −80° C. before transfer to bioanalytical laboratory for determination of total drug concentration.

Sample Analysis

All plasma samples were analyzed for free apomorphine (for groups 2 and 3, this analysis measured the amount of apomorphine released from the polymer) and groups 2 and 3 were analyzed for total apomorphine (released drug plus drug still conjugated to the polymer). Analysis was carried out by liquid chromatographic triple quadrupole mass spectrometric (LC-MS/MS) analysis. Using 30.0 μL aliquot of plasma, the lower limit of quantification (LLOQ) for the free apomorphine assay in plasma was 0.1 ng/mL in Group 1 animals and 0.2 ng/mL for Groups 2 and 3 animals. The LLOQ for the total apomorphine assay in plasma was 0.5 ng/mL for Groups 2 and 3. The higher limit of quantification was 300 ng/mL for free apomorphine and 1000 ng/mL for total apomorphine in plasma for all groups.

Formulated dose solutions were also tested for test article concentration and dose accuracy.

Observations

All animals were weighed on the day before dosing to determine the dose volume to be administered. Twice daily (approximately 9:30 a.m. and 4:00 p.m.), cage-side observations for general health and appearance were carried out for the duration of the study. Animals were given a physical examination prior to study initiation to confirm the health of the animals. In addition, the animals were observed before and after initial dosing and each sample collection time point. General condition, behavior, activity, excretion, respiration or other unusual observations noted throughout the study were recorded. A staff veterinarian or veterinary technician evaluated each animal for clinical observations.

The body weights of each non-naïve female monkey at the start of the study are shown in Table 2.

TABLE 2

| Test Article | Group | Animal No | Tattoo No. | Body Weight (kg) | Month |
|---|---|---|---|---|---|
| Apomorphine HCl ½$H_2O$ | 1 | 1501 | C1409222 | 3.3 | 49 |
| | | 1502 | C1409198 | 3.33 | 49 |
| | | 1503 | C1404344 | 2.68 | 39 |
| POZ-Apomorphine A | 2 | 2501 | C1505008 | 2.74 | 37 |
| | | 2502 | C1504304 | 2.7 | 42 |
| | | 2503 | C1406054 | 3.32 | 52 |
| POZ-Apomorphine B | 3 | 3501 | C1409080 | 3.87 | 49 |
| | | 3502 | C1502304 | 2.7 | 40 |
| | | 3503 | C1505154 | 2.86 | 41 |

The percent of released apomorphine (PR) was calculated to understand the differences in exposure of released drug to total drug for groups 2 and 3 using the following formula:

$$PR\%=[AUC_{0\text{-}last}(\text{free})\div AUC_{0\text{-}last}(\text{total})]\times 100.$$

Nominal sampling times were used to calculate all parameters since in no situations were there deviations of sampling times.

Pharmacokinetics of Free Apomorphine

Figure 2:
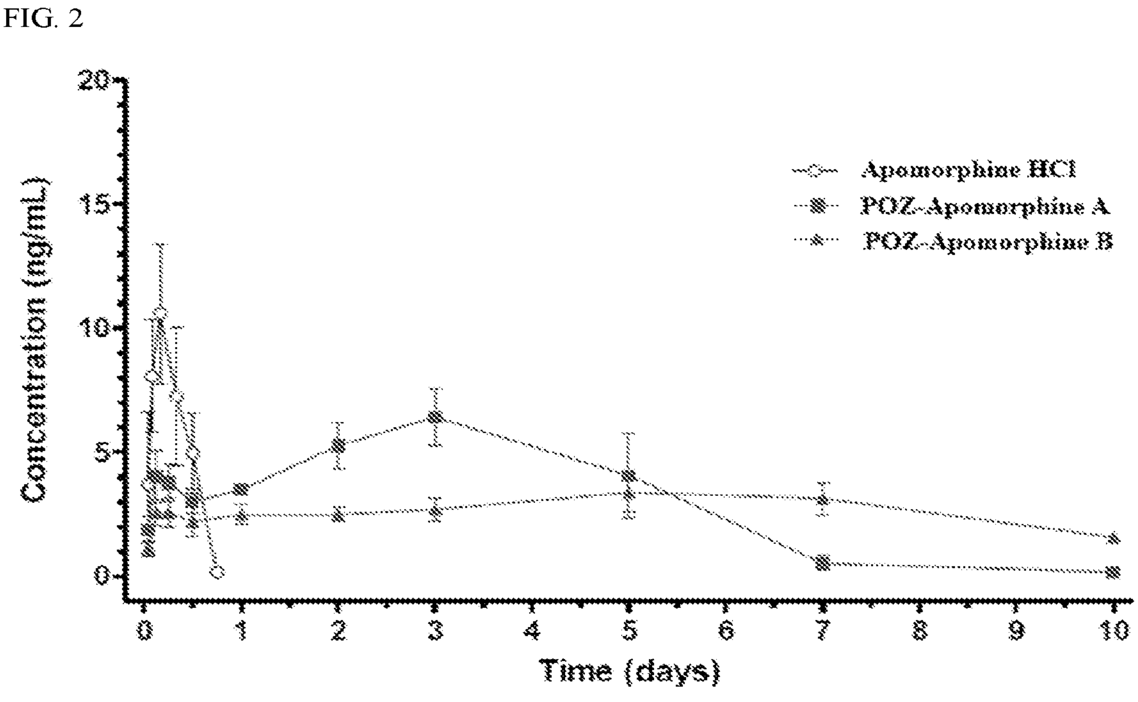
FIG. 2 shows the PK profile for free apomorphine after subcutaneous infusion of apomorphine HCl and subcutaneous injection of POZ-Apomorphine A and POZ-Apomorphine B in female monkeys.

The pharmacokinetics of free apomorphine were investigated in female monkeys following a single SC infusion of apomorphine HCl (1.5 mg/kg) and a single SC injection of POZ-Apomorphine A and POZ-Apomorphine B conjugates at a dose of 1.5 mg/kg (based on apomorphine equivalents). Mean plasma concentrations of free apomorphine are shown in FIG. 2 for each test article.

The calculated pharmacokinetic parameters of free apomorphine in plasma are presented in Table 3 (Mean, SD for n=3). These parameters include the $C_{max}$, $T_{max}$, $t_{1/2}z$ Vz/F, CL/F and AUC values for infinity ($AUC_{0\text{-}inf}$), for 1 week ($AUC_{0\text{-}168}$) and up to the last measurable time point ($AUC_{0\text{-}last}$).

TABLE 3

(PK parameters for free apomorphine)

| Group | | $t_{1/2}z$ h | $T_{max}$ h | $C_{max}$ ng/ml | $AUC_{0\text{-}inf}$ h*ng/ml | $AUC_{0\text{-}last}$ h*ng/ml | $AUC_{0\text{-}168}$ h*ng/ml | $Vz/F_{obs}$ ml/kg | $CL/F_{obs}$ ml/h/kg |
|---|---|---|---|---|---|---|---|---|---|
| 1 | Mean | 1.7 | 4.0 | 10.6 | 90.2 | 89.8 | — | 43,621 | 17,357 |
| | SD | 0.2 | 0 | 2.8 | 22.6 | 22.6 | — | 14,398 | 4,375 |
| 2 | Mean | 22.5 | 88.0 | 6.6 | 666 | 656 | 647 | 73,896 | 2,272 |
| | SD | 1.4 | 27.7 | 0.9 | 71 | 76 | 65 | 10,405 | 254 |
| 3 | Mean | 143.4 | 104.0 | 3.5 | 968 | 640 | 478 | 313,446 | 1,638 |
| | SD | 101.4 | 27.7 | 1.3 | 255 | 204 | 159 | 171,991 | 508 |

Example 19—The POZ-Apomorphine Conjugates Provide Enhanced Pharmacokinetic Properties as Compared to Unconjugated, Free Apomorphine Pharmacokinetic Analysis Plasma concentration-time profiles of free apomorphine and total apomorphine were analyzed using a non-compartmental model by a validated WinNonlin® program (Pharsight, Version 6.3). Maximum plasma concentration ($C_{max}$) and time to reach $C_{max}$($T_{max}$) were taken from the plasma concentration versus time profiles. In order to access how drug loading (% w/w) would affect the pharmacokinetic profiles, the area under the plasma concentration-time curve (AUC) from time zero to 168 hours post dose ($AUC_{0\text{-}168}$) was determined as the treatment phase and the AUC from time zero to the time of the last observation ($AUC_{0\text{-}last}$) was also calculated using the linear up/log down trapezoidal rule (Gabrielsson et al., Non-compartmental analysis in "Pharmacokinetic and Pharmacodynamic Data Analysis: Concepts & Applications", 4th edition, Chapter 2.8., page 161-180. Swedish Pharmaceutical Press; 2006).

$T_{max}$ and $C_{max}$ values were reported for each plasma concentration-time profile. The elimination half-life $t_{1/2}z$ values were calculated and reported with coefficients of correlation for the elimination phase using at least 3 points.

Review of the concentration-time plots (FIG. 2) and the calculated pharmacokinetic results (Table 3) show a distinct difference between apomorphine HCl and the POZ-Apomorphine A and POZ-Apomorphine B conjugates. The concentration of free apomorphine (ng/mL) following a single 12 h SC infusion of 1.5 mg/kg apomorphine HCl provides a $T_{max}$ at 4 h with an average $C_{max}$ of about 10.6 ng/mL. The $AUC_{0\text{-}last}$ value was calculated to be 89.8 h*ng/ml. Following the infusion, the drug is completely cleared and below the limit of quantification (BLQ) by 24 h post-infusion. The terminal half-life for apomorphine HCl was calculated to be 1.7 h.

On the other hand, free apomorphine levels following SC injection of POZ-Apomorphine A and POZ-Apomorphine B conjugates show differences in the concentration-time profiles for each conjugate. The concentration of free apomorphine (ng/ml) following a single SC injection of 1.5 mg/kg (apomorphine equivalents) of the POZ-Apomorphine A conjugate increased gradually during the first 3 days with an average $T_{max}$ and $C_{max}$ of 88 h and 6.6 ng/mL, respectively. The $AUC_{0\text{-}last}$ value was calculated to be 656 h*ng/ml. The drug is completely cleared and BLQ by 240 h post-injection. The concentration of free apomorphine (ng/ml) following a single SC injection of 1.5 mg/kg (apomorphine equivalents)

of the POZ-Apomorphine B conjugate increased gradually during the first 5 days with an average $T_{max}$ and $C_{max}$ of 104 h and 3.5 ng/mL, respectively. The $AUC_{0-last}$ value was calculated to be 640 h*ng/ml. The drug is has not cleared by 240 h post-injection. The terminal half-life of apomorphine released from the POZ-Apomorphine A and B conjugates was are 22.5 and 143.4 h, respectively.

The $t_{1/2}z$ values determined for the POZ-Apomorphine A and B conjugates in-vivo show the same trend as the $t_{1/2}$ values determined for the POZ-Apomorphine A and B conjugates in the in-vitro human plasma release assays, with the POZ-Apomorphine A conjugate having a shorter half-life in each assay as compared to the POZ-Apomorphine B conjugate. This comparison shows the in-vitro plasma assay reliably predicts the half-life in the in-vivo studies.

Pharmacokinetics of Total Apomorphine

Figure 3:
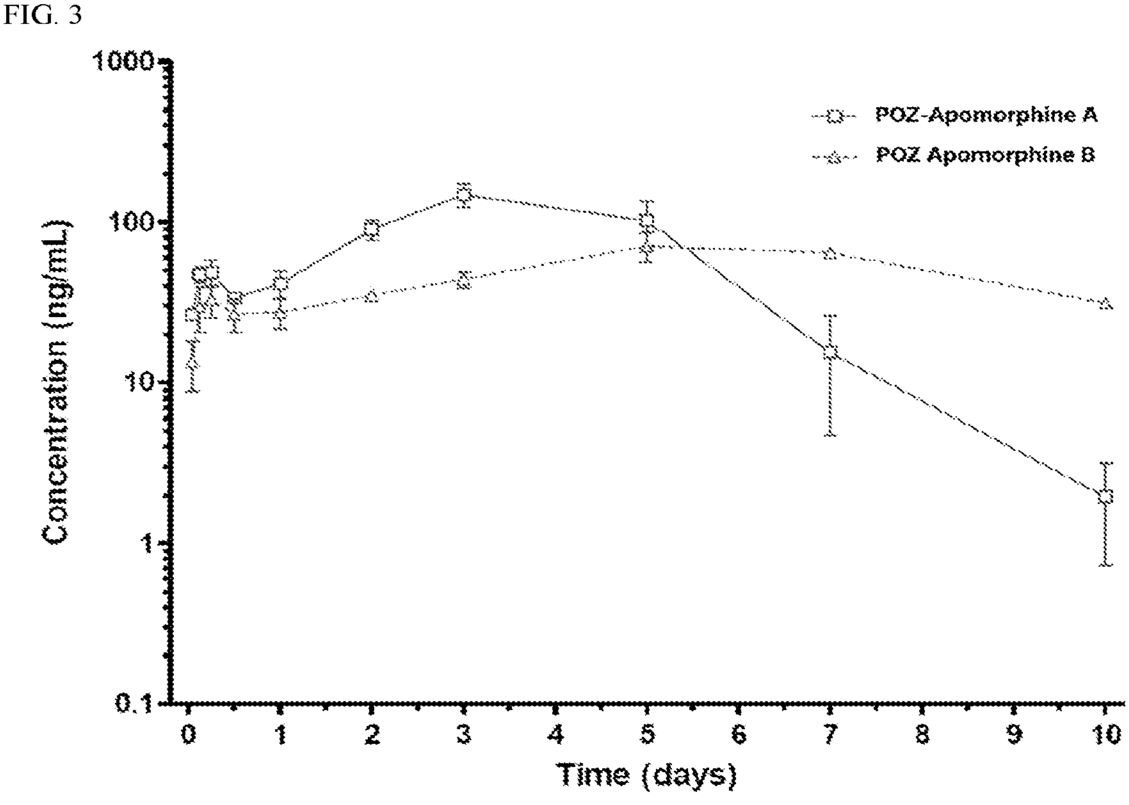
FIG. 3 shows the PK profile for total apomorphine after subcutaneous infusion of apomorphine HCl and subcutaneous injection of POZ-Apomorphine A and POZ-Apomorphine B in female monkeys.

The pharmacokinetics of total apomorphine were investigated in female monkeys following a single SC injection of the POZ-Apomorphine A and POZ-Apomorphine B conjugates at a dose of 1.5 mg/kg, based on apomorphine equivalents. Mean plasma concentrations of free apomorphine are shown in FIG. 3 for each condition.

The calculated pharmacokinetic parameters of total apomorphine in plasma are presented in Table 4. These parameters include the $C_{max}$, $T_{max}$, $t_{1/2}z$ Vz/F, CL/F and AUC values for infinity ($AUC_{0-inf}$), for 1 week ($AUC_{0-168}$) and up to the last measurable time point ($AUC_{0-last}$).

TABLE 4

| Group | | $t_{1/2}z$ | $T_{max}$ h | $C_{max}$ ng/ml | $AUC_{0-inf}$ h*ng/ml | $AUC_{0-last}$ h*ng/ml | $AUC_{0-168}$ h*ng/ml | Vz/F obs ml/kg | CL/F obs ml/h/kg | PR % |
|---|---|---|---|---|---|---|---|---|---|---|
| 2 | Mean | 20.9 | 88.0 | 151.3 | 138986 | 13835 | 13368 | 3257 | 109 | 4.8 |
| | SD | 2.5 | 27.7 | 19.3 | 1164 | 1623 | 1314 | 232 | 13 | 0.6 |
| 3 | Mean | 106.9 | 136.0 | 72.7 | 16456 | 11610 | 8317 | 13986 | 91 | 5.5 |
| | SD | 35.2 | 27.7 | 11.6 | 505 | 1232 | 1135 | 4169 | 3 | 1.3 |

Review of the concentration-time plot (FIG. 3) and the calculated pharmacokinetic results (Table 4) for the POZ-Apomorphine A and B conjugates at the 1.5 mg/kg dose (apomorphine equivalents) show they differ in their concentration-time profiles. The total drug levels for the POZ-Apomorphine A conjugate increased gradually in the first 3 days with an average $T_{max}$ and $C_{max}$ of 88 h and 151.3 ng/mL, respectively. The $AUC_{0-last}$ value was calculated to be 13835 h*ng/ml. The drug is cleared and BLQ by 240 h. The total drug levels for the POZ-Apomorphine B conjugate increased gradually in the first 5 days with an average $T_{max}$ and $C_{max}$ of 107 h and 72.6 ng/mL, respectively. The $AUC_{0-last}$ value was calculated to be 11610 h*ng/ml. The drug is has not cleared by 240 h. The terminal half-life of apomorphine released from the POZ-Apomorphine A and B conjugates was are 20.9 and 106.9 h, respectively.

The released apomorphine to total apomorphine ratios, are reported as percent released apomorphine (PR; calculated as described herein). The PR values were 4.8 and 5.5 for the POZ-Apomorphine A and B conjugates, respectively. The released and total apomorphine values for Group 1 are the same (as shown in Table 3).

Summary of Pharmacokinetic Data

After one SC infusion of apomorphine HCl and one SC injection of the POZ-Apomorphine A and POZ-Apomorphine B conjugates, the pharmacokinetic profiles of released apomorphine and total apomorphine are summarized as below.

The attachment of apomorphine to POZ polymers allowed for sustained delivery of apomorphine over 5-10 days. The $T_{max}$ values increased 22 and 26 times for the POZ-Apomorphine A and POZ-Apomorphine B conjugates, respectively, as compared to apomorphine HCl. The $t_{1/2}z$ increased 13.2 and 84.3 times for the POZ-Apomorphine A and POZ-Apomorphine B conjugates, respectively, as compared to apomorphine HCl.

Furthermore, the attachment of apomorphine to the POZ polymers allowed for an attenuation of the $C_{max}$ from 10.6 ng/mL to 6.6 and 3.5 ng/mL for the POZ-Apomorphine A and POZ-Apomorphine B, respectively, as compared to apomorphine HCl. In addition, the drug exposure by measure of $AUC_{0-last}$ increased over 7-fold when apomorphine was released from the POZ-Apomorphine A and B conjugates. These data show that the total drug exposure of apomorphine increased significantly when the apomorphine was release from the POZ-Apomorphine A and B conjugates.

The data show the surprising effect that the nature of the blocking group on the second phenolic hydroxyl of the catechol moiety of apomorphine affects the rate of release of apomorphine from the POZ conjugates. The POZ-Apomorphine A conjugate provides a sustained release of apomorphine over a 5-day period while the POZ-Apomorphine B conjugate provides a steady-state release of apomorphine over a 10 day period. This result clearly demonstrates the rate of release of apomorphine from the described POZ conjugates can be controlled to provide a rate of release (a release profile) based on the selection of the blocking group on the second phenolic hydroxyl of the catechol moiety of apomorphine.

The total apomorphine plasma levels mirror the released apomorphine levels in the concentration-time profile. The released to total apomorphine ratios (PR) were shown to be between 4.8-5.5%. There was no evidence of dose dumping (burst effect) after administration of the POZ-Apomorphine A and B conjugates.

Example 20—The POZ-Apomorphine Conjugates Did Not Result in Skin Irritation When Administered by the Subcutaneous Route It has been reported in literature that apomorphine (Apo-Go, 10 mg/mL formulation) when injected under the skin will create lumps (nodules) that are red and irritating. All animals were monitored daily for there skin reactions. Photographs were taken to study the severity of the reactions and observations were recorded. Bases on the presence of erythema and swelling, the skin reactions were recorded as none, slight, well defined, moderate and severe.

Observation for Skin Reactions

The visual observations for each test animal are summarized in Table 5.

TABLE 5

Figure 4A:
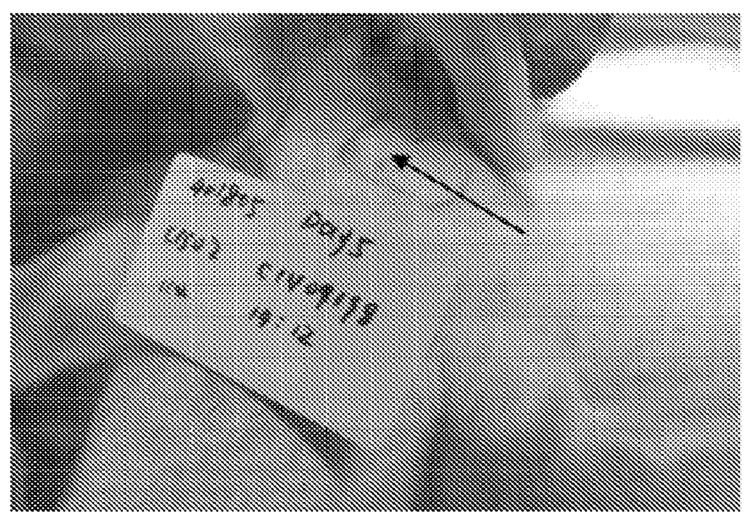
FIG. 4A shows a depiction of skin reactions on Day 5 post-administration following single subcutaneous administration (by slow infusion) of free apomorphine (Group 1, animal 1502).

| Group | Animal No | Observations |
|---|---|---|
| 1 | 1501 C1409222 | Day 1: No skin reaction up to 8 h post start of infusion; injection site showed slight redness after the 12 h infusion. Day 2: Injection site had slight redness at 24 h post dosing, swelling (when a finger was used to touch the injection site); redness also present adjacent to the injection site. Day 3: The injection site and other skin areas observed on Day 2 still have redness and there is yellow secretion appearing around the injection site. Swelling when a finger was used to touch the injection site. Day 4: The injection site and other skin areas observed on Day 2 still have redness and there is additional yellow secretion appearing around the injection site when compared to Day 3. Swelling (when a finger was used to touch the injection site). Day 5: The injection site and other skin areas observed on Day 2 still have redness and there is further yellow secretion appearing around the injection site when compared to Day 4. Swelling when a finger was used to touch the injection site (FIG. 4A). Day 7: Swelling and redness reduced when compared to Day 5. Day 15: Skin appears normal. |
| | 1502 C1409198 | Day 1: no skin reaction up to 8 h post start of infusion; injection site showed slight redness after the 12 h infusion. Day 2: Injection site has slight redness at 24 h post infusion, swelling (when a finger was used to touch the injection site). Day 3: Injection site has slight redness at 48 h post infusion, swelling (when a finger was used to touch the injection site). Day 4: The injection site and other skin areas observed on Day 3 still have redness and there is yellow secretion appearing around the injection site when compared to Day 3. Swelling (when a finger was used to touch the injection site). Day 5: The injection site and other skin places observed on Day 5 still have redness, and there is yellow secretion appearing around the injection site when compared to Day 4. Swelling when a finger was used to touch the injection site. Day 7: Swelling and redness reduced when compared to Day 5. Day 15: Skin appears normal. |
| | 1503 C1404344 | Day 1: No skin reaction up to 8 h post start of infusion; injection site showed slight redness after the 12 h infusion. Day 2: Injection site has slight redness at 24 h post infusion, swelling (when a finger was used to touch the injection site). Day 3: Injection site has slight redness at 48 h post infusion, swelling (when a finger was used to touch the injection site). Day 4: Injection site has slight redness at 72 h post infusion, swelling (when a finger was used to touch the injection site). |

TABLE 5-continued

| Group | Animal No | Observations |
|---|---|---|
| | | Day 5: Injection site has slight redness at 96 h post infusion, swelling (when a finger was used to touch the injection site). Day 7: Yellow scab observed when compared to Day 5. Day 15: Skin appears normal. |
| 2 | 2501 C1505008 | Day 1 to Day 15: No erythema and swelling. Day 15: Skin appears normal. |
| | 2502 C1504304 | Day 1 to Day 15: No erythema and swelling. Day 15: Skin appears normal. |
| | 2503 C1406054 | Day 1 to Day 15: No erythema and swelling. Day 15: Skin appears normal. |
| 3 | 3501 C1409080 | Day 1 to Day 15: No erythema and swelling. Day 15: Skin appears normal. |
| | 3502 C1502304 | Day 1 to Day 15: No erythema and swelling. Day 15: Skin appears normal. |
| | 3503 C1505154 | Day 1 to Day 15: No erythema and swelling. Day 15: Skin appears normal. |

Figure 4B:
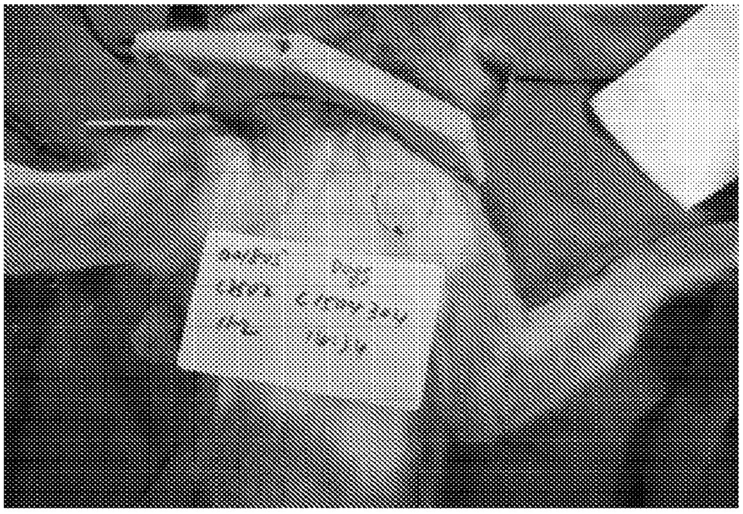
FIG. 4B shows a depiction of skin reactions on Day 5 post-administration following single subcutaneous administration (by injection) of POZ-Apomorphine A (Group 2, animal 2502).
Figure 4C:
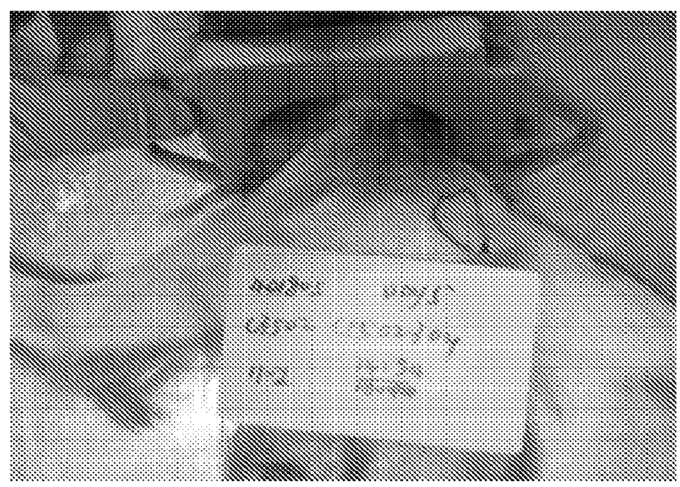
FIG. 4C shows a depiction of skin reactions on Day 5 post-administration following single subcutaneous administration (by injection) of POZ-Apomorphine B (Group 3, animal 3502).

FIGS. 4A-C show the difference between a group 1 animal (1502), a group 2 animal (2502), and a group 3 animal (3502) on day 5 post infusion. As shown in FIG. 4A, animal 1502 shows scarring with yellow secretion as well as redness and swelling at the infusion site, while animals 2502 and 3502 have no scars, secretions, swelling or redness (FIGS. 4B and C, respectively).

In summary, group 1 animals had significant redness, swelling and yellow exudate at and around the infusion site from Day 1 to Day 7, while group 2 and 3 animals had no skin reactions throughout the course of the study.

These results indicated the POZ-Apomorphine A and B conjugates are well tolerated by the primates after SC injection.

Example 21—The POZ-Apomorphine Conjugates Did not Result in Skin Irritation when Administered by the Subcutaneous Route after Administration of Multiple Doses An in-vivo pharmacokinetic study of POZ-apomorphine conjugates of the present disclosure was conducted in primates to determine the free plasma apomorphine levels (all test articles) and total (for POZ-Apomorphine conjugates) plasma apomorphine levels as well as dermal reactions to each of the test articles after a single subcutaneous (SC) infusion (apomorphine HCl) and single SC injection (POZ-Apomorphine conjugates).

POZ-Apomorphine Conjugates

The POZ-Apomorphine conjugates used in this study are those described in Example 6 (POZ-Apomorphine A), Example 7 (POZ-Apomorphine B) and Example 15 (POZ-Apomorphine G).

Dosing

Non-naïve female cynomolgus monkeys were used in the study. The animals had a minimum of 4 weeks since the last treatment of drug in the previous study. They were assigned to three groups with 3 animals per group. Animals in groups 1, 2 and 3 received four weekly doses of a SC injection of the POZ-Apomorphine A, POZ-Apomorphine B and POZ-Apomorphine G conjugates at a dose of 3.0 mg/kg (based on apomorphine equivalents). The dosing schedule is as indicated in Table 6.

TABLE 6

| Group No[1] | Treatment Test Article | Dose (mg/kg)[2] | Dose Vol (ml/kg) | Vehicle | Route[3] |
|---|---|---|---|---|---|
| 1 | POZ apomorphine A | 3.0 | 0.3 | D5W | SC |
| 2 | POZ apomorphine B | 3.0 | 0.3 | D5W | SC |
| 3 | POZ apomorphine G | 3.0 | 0.3 | D5W | SC |

[1]for all groups, n = 3
[2]based on active drug
[4]single injection on days 0, 7, 14, and 21

The test articles were dosed subcutaneously (as described in Table 6) in the right shoulder on days 0 and 14 and in the left shoulder on days 7 and 21, of each monkey. Animals were observed for signs of ill health, general adverse reactions, inflammation at the sites of injection, and mortality to treatment as described herein and in Example 18. Photographs were taken to study the severity of the reactions and observations that were recorded.

Blood Sampling and Plasma Preparation

All animals were dosed at 0 h. Blood samples from Groups 1 to 3 were collected at 3, 6, 12, 24, 48, 72, 120, 168, 171, 174, 180, 192, 216, 240, 288, 336, 339, 342, 348, 360, 384, 408, 456, 504, 507, 510, 516, 528, 552, 576, 624, 672, 720, 768, 840, 888, 936 and 1008 hours post-dose. Blood samples were collected and processed as described in Example 18.

Sample Analysis

All plasma samples were analyzed for free apomorphine (this analysis measured the amount of apomorphine released from the polymer) and for total apomorphine (released drug plus drug still conjugated to the polymer). Analysis was carried out as described in Example 18.

Pharmacokinetic Analysis

Plasma concentration-time profiles of free apomorphine and total apomorphine will be analyzed using a non-compartmental model by a validated WinNonlin® program (Pharsight, Version 6.3) as described in Example 18.

Observations

All animals were weighed on the day before dosing to determine the dose volume to be administered and were/will be conducted as described in Example 18.

Observations of Skin Reactions

As discussed in Example 20, apomorphine (Apo-Go, 10 mg/mL formulation) has been reported to result in severe skin irritation after administration in humans. To determine if the Apo-A, Apo-B, and Apo-G conjugates induced skin reactions at a concentration of 3.0 mg/kg (as compared to the 1.5 mg/kg dose described in Examples 18 and 20), all animals were/will be monitored daily for these skin reactions. Photographs were/will be taken to study the skin reactions and observations were/will be recorded. Bases on the presence of erythema and swelling, the skin reactions were/will be recorded as none, slight, well defined, moderate and severe.

Figure 5A:
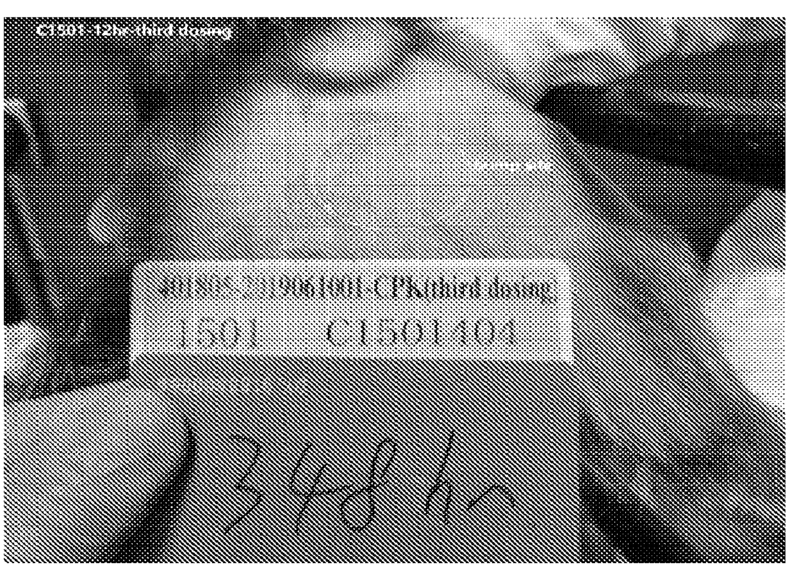
FIG. 5A shows a depiction of skin reactions on Day 14, 12 hours after administration of the third dose of POZ-Apomorphine A (Group 1) via subcutaneous administration (by injection).
Figure 5B:
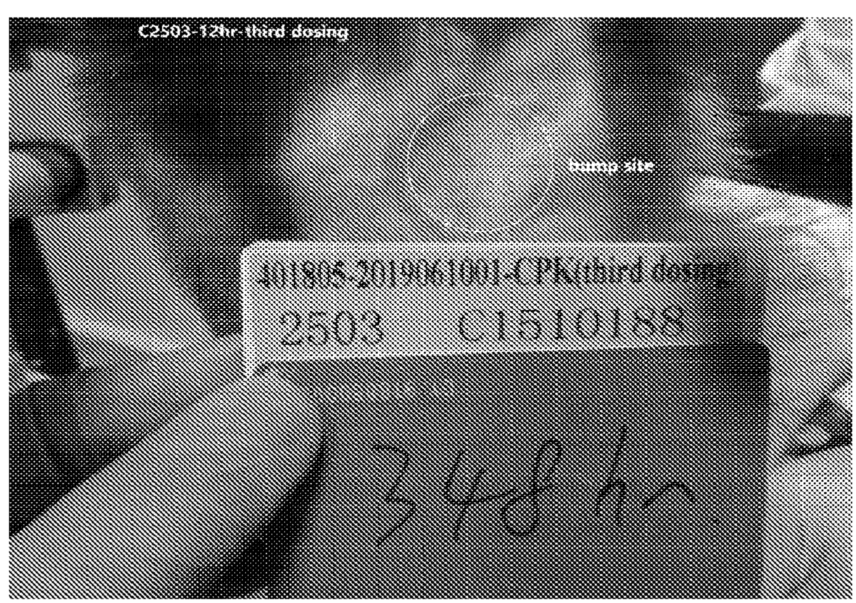
FIG. 5B shows a depiction of skin reactions on Day 14, 12 hours after administration of the third dose of POZ-Apomorphine B (Group 2) via subcutaneous administration (by injection).
Figure 5C:
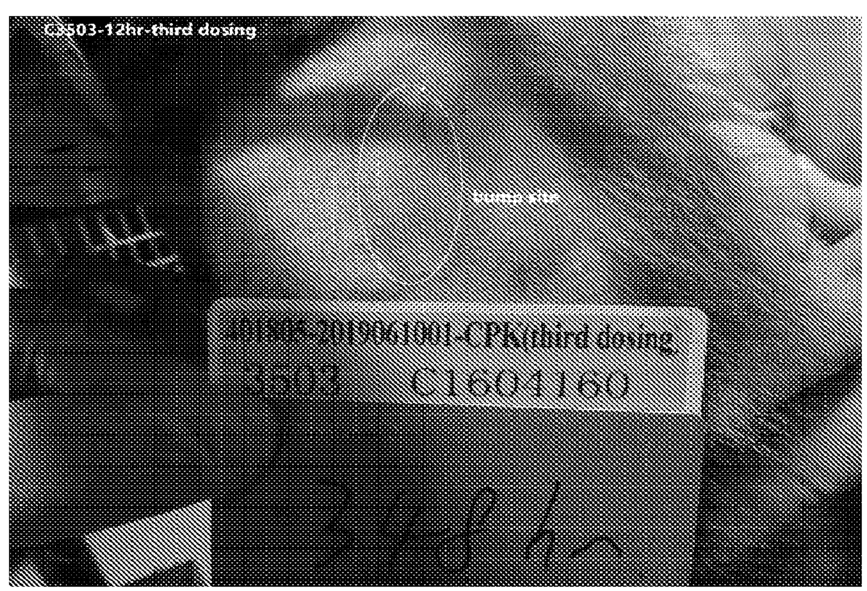
FIG. 5C shows a depiction of skin reactions on Day 14, 12 hours after administration of the third dose of POZ-Apomorphine G (Group 3) via subcutaneous administration (by injection).

After the third dose of the Apo-A, Apo-B, and Apo-G conjugates (day 14), photographs were taken 12 hours after administration. The skin at the site of injection (referred to as the bump site) of each animal in Groups 1 to 3 appeared normal with no sign of erythema and swelling. FIGS. 5A-C show skin sites with no scars, secretions, swelling or redness 12 hours after the third dose, for one animal from each group.

These results indicated the POZ-Apomorphine A, B, and G conjugates are well tolerated by primates after SC injection at a dose of 3.0 mg/kg (based on apomorphine equivalents).

Additional Aspects

Additional exemplary claims supported by the specification include, but are not limited to, the following.

Aspect 1: A compound of the formula V, or a pharmaceutically acceptable salt thereof,

V

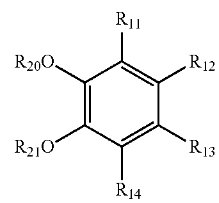

wherein:

$R_{11}$, $R_{12}$, $R_{13}$ and $R_{14}$ are independently selected from H, OH, halogen, alkoxy, $NO_2$, unsubstituted alkyl, heteroalkyl, alkenyl, or alkynyl, substituted alkyl, heteroalkyl, alkenyl, or alkynyl, aryl, substituted aryl, cycloalkyl, substituted cycloalkyl, heterocyclyl, substituted heterocyclyl, heteroaryl, substituted heteroaryl, heterocyclylalkyl, substituted heterocyclylalkyl, heteroarylalkyl, substituted heteroarylalkyl, or any two of $R_{11}$, $R_{12}$, $R_{13}$ and $R_{14}$ that are adjacent to one another, taken together with the carbons to which they are attached, may form an optionally substituted aryl, heteroaryl, heterocyclyl ring; and one of $R_{20}$ and $R_{21}$ is H or a blocking group and the other of $R_{20}$ and $R_{21}$ is H, a group comprising an active functional group, or a blocking group, provided that both $R_{20}$ and $R_{21}$ are not each H, wherein the group comprising the active functional group comprises a first cleavable moiety and the blocking group comprises a second cleavable moiety.

Aspect 2: The compound of aspect 1, wherein one of $R_{20}$ and $R_{21}$ is the blocking group and the other of $R_{20}$ and $R_{21}$ is the group comprising the active functional group.

Aspect 3: The compound of aspect 1, wherein the group comprising the active functional group is $R_{24}$—$R_{25}$—$R_{26}$, wherein:

$R_{24}$ is —C(O)—, —O—C(O)—, —C(O)—NH-cyclic-O—C(O)—, —C(O)—NH—($C_6H_4$)—O—C(O)—, or —O—P(O)($OR_9$)(O)—;

cyclic represents substituted or unsubstituted aryl, heterocylalkyl, heteroaryl, heterocyclyl or cycloalkyl;

$R_9$ is H or a substituted or unsubstituted C1-C5 alkyl;

$R_{25}$ is an unsubstituted or substituted alkyl, an unsubstituted or substituted alkenyl, an unsubstituted or substituted aralkyl or an unsubstituted or substituted aryl group; and $R_{26}$ is an active functional group or a moiety comprising an active functional group capable of forming a linkage with a group on the polymer.

Aspect 4: The compound of aspect 3, wherein the active functional group is azide group or an alkyne group.

Aspect 5: The compound of aspect 3, wherein $R_{24}$—$R_{25}$—$R_{26}$ is $N_3$—$(CH_2)_{1-6}$—C(O)—, C≡C—$(CH_2)_{1-6}$—C(O)—, $N_3$—$(CH_2)_3$—C(O), or C≡C—$(CH_2)_3$—C(O).

Aspect 6: The compound of aspect 3, wherein $R_{24}$ forms a bond with the oxygen of $R_{20}$ or $R_{21}$ and $R_{24}$ and the O to which it is linked forms the first cleavable moiety.

Aspect 7: The compound of aspect 2, where the compound is a compound of formula VI, or a pharmaceutically acceptable salt thereof

VI

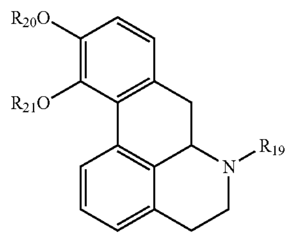

wherein:

$R_{19}$ is H, unsubstituted alkyl, alkenyl, or alkynyl, substituted alkyl, alkenyl, or alkynyl, benzyl, substituted benzyl, cycloalkyl, substituted cycloalkyl, aryl, substituted aryl, acyl, tetrahydrofuranyl, tetrahydropyranyl, nicotinyl or a 1-aryltetrazolyl.

Aspect 8: The compound of aspect 7, wherein $R_{19}$ is —H, —$CH_3$, —$CH_2$—$CH_3$, —$CH_2$—$CH_2$—$CH_3$, —CH($CH_3$)$_2$—$CH_2$—$CH_2$—$CH_2$—$CH_3$, or

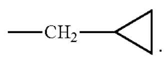

Aspect 9: The compound of aspect 7, wherein the group comprising the active functional group is $R_{24}$—$R_{25}$—$R_{26}$, wherein:

$R_{24}$ is —C(O)—, —O—C(O)—, —C(O)—NH-cyclic-O—C(O)—, —C(O)—NH—(C6H$_4$)—O—C(O)—, or —O—P(O)(OR$_9$)(O)—;

cyclic represents substituted or unsubstituted aryl, heterocylalkyl, heteroaryl, heterocyclyl or cycloalkyl;

$R_9$ is H or a substituted or unsubstituted C1-C5 alkyl;

$R_{25}$ is an unsubstituted or substituted alkyl, an unsubstituted or substituted alkenyl, an unsubstituted or substituted aralkyl or an unsubstituted or substituted aryl group; and $R_{26}$ is an active functional group or a moiety comprising an active functional group capable of forming a linkage with a group on the polymer.

Aspect 10: The compound of aspect 9, wherein the active functional group is azide group or an alkyne group.

Aspect 11: The compound of aspect 9, wherein $R_{24}$—$R_{25}$—$R_{26}$ is $N_3$—($CH_2$)$_{1-6}$—C(O)—, C≡C—($CH_2$)$_{1-6}$—C(O)—, $N_3$—($CH_2$)$_3$—C(O), or C≡C—($CH_2$)$_3$—C(O).

Aspect 12: The compound of aspect 9, wherein $R_{24}$ forms a bond with the oxygen of one of $R_{20}$ or $R_{21}$ and $R_{24}$ and the O to which it is linked forms the first cleavable moiety.

Aspect 13: The compound of any one of aspects 1 to 12, wherein the blocking group is —$R_{22}$—$R_{23}$;

$R_{22}$ is —C(O)—, —C(O)—O—, —C(O)—NH-cyclic-O—C(O)—, —C(O)—NH—($C_6H_4$)—O—C(O)—, $CH_3$($CH_2$)$_{1-4}$—O—C(O)—($CH_2$)$_{1-4}$—C(O)— or —O—P(O)(OR$_9$)—;

cyclic represents substituted or unsubstituted aryl, heterocylalkyl, heteroaryl, heterocyclyl or cycloalkyl;

$R_9$ is H or a substituted or unsubstituted C1-C5 alkyl; and $R_{23}$ is an unsubstituted or substituted alkyl, an unsubstituted or substituted alkenyl, an unsubstituted or substituted aralkyl or an unsubstituted or substituted aryl group.

Aspect 14: The compound of any one of aspects 1 to 13, wherein $R_{22}$ forms a bond with the oxygen of one of $R_{20}$ or $R_{21}$ and $R_{22}$ and the O to which it is linked forms the second cleavable moiety.

Aspect 15: The compound of any one of aspects 1 to 13, wherein the blocking group has the structure ($CH_3$)$_y$—($CH_x$)—($CH_2$)$_{0-6}$—C(O)—, ($CH_3$)$_y$—($CH_x$)—C(O)—, $CH_3$—($CH_2$)$_{0-6}$—C(O)—, $CH_3$—($CH_2$)$_{0-6}$—C(O)—($CH_2$)$_{0-6}$—, wherein when y is 1, x is 2, when y is 2, x is 1, or when y is 3, x is 0.

Aspect 16: The compound of any one of aspects 1 to 15, wherein the blocking group has the structure $CH_3$—C(O)—, $CH_3$—($CH_2$)$_2$—C(O)—, $CH_3$—$CH_2$—C(O)—, ($CH_3$)$_2$—CH—C(O)—, ($CH_3$)$_3$—C—C(O)—, $CH_3CH_2$—O—C(O)—$CH_2CH_2$—C(O)—, ($CH_2$)$_{0-6}$—C(O)—, or —C(O)—

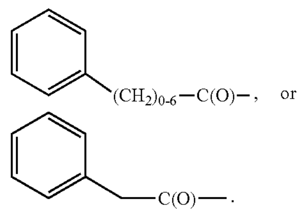

Aspect 17: The compound of aspect 1, wherein each of $R_{20}$ and $R_{21}$ is the blocking group or one of $R_{20}$ and $R_{21}$ is the blocking group and the other of $R_{20}$ and $R_{21}$ is H.

Aspect 18: The compound of aspect 17, wherein the blocking group is $R_{22}$—$R_{23}$; $R_{22}$ is —C(O)—, —C(O)—O—, —C(O)—NH-cyclic-O—C(O)—, —C(O)—NH—(C6H$_4$)—O—C(O)—, $CH_3$($CH_2$)$_{1-4}$—O—C(O)— ($CH_2$)$_{1-4}$—C(O)— or —O—P(O)(OR$_9$)—;

cyclic represents substituted or unsubstituted aryl, heterocylalkyl, heteroaryl, heterocyclyl or cycloalkyl;

$R_9$ is H or a substituted or unsubstituted C1-C5 alkyl; and $R_{23}$ is an unsubstituted or substituted alkyl, an unsubstituted or substituted alkenyl, an unsubstituted or substituted aralkyl or an unsubstituted or substituted aryl group.

Aspect 19: The compound of aspect 17 or 18, wherein $R_{22}$ forms a bond with the oxygen of one or both of $R_{20}$ or $R_{21}$ and $R_{22}$ and the O to which it is linked forms the second cleavable moiety.

Aspect 20: The compound of any one of aspects 17 to 19, wherein the blocking group has the structure ($CH_3$)$_y$—($CH_x$)—($CH_2$)$_{0-6}$—C(O)—, ($CH_3$)$_y$—($CH_x$)—C(O)—, $CH_3$—($CH_2$)$_{0-6}$—C(O)—, $CH_3$—($CH_2$)$_{0-6}$—C(O)—($CH_2$)$_{0-6}$—, wherein when y is 1, x is 2, when y is 2, x is 1, or when y is 3, x is 0.

Aspect 21: The compound of any one of aspects 17 to 19, The compound of aspect 81, wherein the blocking group has the structure $CH_3$—C(O)—, $CH_3$—($CH_2$)$_2$—C(O)—, $CH_3$—$CH_2$—C(O)—, ($CH_3$)$_2$—CH—C(O)—, ($CH_3$)$_3$—C—C(O)—, $CH_3CH_2$—O—C(O)—$CH_2CH_2$—C(O)—,

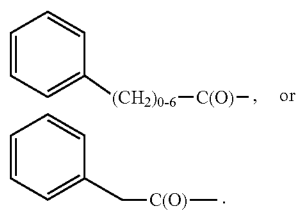

Aspect 22: The compound of aspect 17, where the compound is a compound of formula VI, or a pharmaceutically acceptable salt thereof

VI

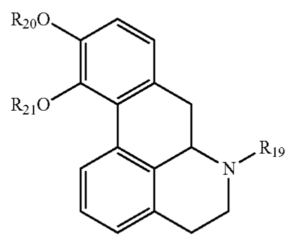

wherein:

$R_{19}$ is H, unsubstituted alkyl, alkenyl, or alkynyl, substituted alkyl, alkenyl, or alkynyl, benzyl, substituted benzyl, cycloalkyl, substituted cycloalkyl, aryl, substituted aryl, acyl, tetrahydrofuranyl, tetrahydropyranyl, nicotinyl or a 1-aryltetrazolyl.

Aspect 23: The compound of aspect 22, wherein $R_{19}$ is —H, —$CH_3$, —$CH_2$—$CH_3$, —$CH_2$—$CH_2$—$CH_3$, —$CH(CH_3)_2$—$CH_2$—$CH_2$—$CH_2$—$CH_3$, or

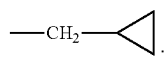

Aspect 24: The compound of aspect 22 or 23, wherein the blocking group is —$R_{22}$—$R_{23}$; $R_{22}$ is —C(O)—, —C(O)—O—, —C(O)—NH-cyclic-O—C(O)—, —C(O)—NH—(C6$H_4$)—O—C(O)—, $CH_3(CH_2)_{1-4}$—O—C(O)— $(CH_2)_{1-4}$—C(O)— or —O—P(O)($OR_9$)—;

cyclic represents substituted or unsubstituted aryl, heterocylalkyl, heteroaryl, heterocyclyl or cycloalkyl;

$R_9$ is H or a substituted or unsubstituted C1-C5 alkyl; and $R_{23}$ is an unsubstituted or substituted alkyl, an unsubstituted or substituted alkenyl, an unsubstituted or substituted aralkyl or an unsubstituted or substituted aryl group.

Aspect 25: The compound of any one of aspects 22 to 24, wherein $R_{22}$ forms a bond with the oxygen of one or both of $R_{20}$ or $R_{21}$ and $R_{22}$ and the O to which it is linked forms the second cleavable moiety.

Aspect 26: The compound of any one of aspects 22 to 25, wherein the blocking group has the structure $(CH_3)_y$—$(CH_x)(CH_2)_{0-6}$—C(O)—, $(CH_3)_y$—$(CH_x)$—C(O)—, $CH_3$—$(CH_2)_{0-6}$—C(O)—, $CH_3$—$(CH_2)_{0-6}$—C(O)—$(CH_2)_{0-6}$—, wherein when y is 1, x is 2, when y is 2, x is 1, or when y is 3, x is 0.

Aspect 27: The compound of any one of aspects 22 to 25, wherein the blocking group has the structure $CH_3$—C(O)—, $CH_3$—$(CH_2)_2$—C(O)—, $CH_3$—$CH_2$—C(O)—,

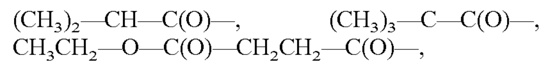

$(CH_3)_2$—CH—C(O)—, $(CH_3)_3$—C—C(O)—, $CH_3CH_2$—O—C(O)—$CH_2CH_2$—C(O)—,

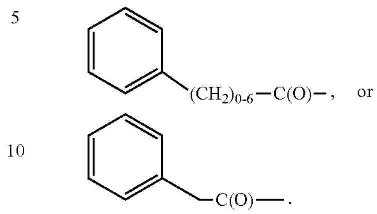

Aspect 28: A method of treating a dopamine-responsive disease or condition in a subject, the method comprising the step of administering to the subject an amount of a compound of any one of aspects 1 to 27, wherein the agent is a dopamine agonist.

Aspect 29: The method of aspect 28, wherein the dopamine-responsive disease or condition is a hypodopaminergic condition, pituitary tumors (prolactinoma), Parkinson's disease, restless leg syndrome, schizophrenia, attention-deficit hyperactivity disorder, hypodopaminergic conditions, SSRI-induced sexual dysfunction, depression, obesity, or type II diabetes.

Aspect 30: The method of aspect 28, wherein the dopamine-responsive disease or condition is Parkinson's disease.

Aspect 31: The method of any one of aspects 28 to 30, wherein the dopamine agonist is apomorphine, arbutamine, carbidopa, dobutamine, dopamine, entacapone, epinephrine, fenoldopam, isoetharine, isoproterenol, levopoda, levonordefrin, masaprocol, methyldopa, methyldopate, norepinephrine, protokylol, tolcapone, or (r)-(+)-fenoldopam.

What is claimed:

1. A conjugate of formula I or a pharmaceutically acceptable salt thereof

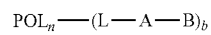

$$POL_n—(L—A—B)_b \quad (I)$$

wherein:

POL is a water-soluble polymer;

n is the degree of polymerization and is from 1-1000;

L is a linkage comprising a first cleavable moiety linking A and POL;

A is a compound comprising a first phenolic hydroxyl group linked to L and a second phenolic hydroxyl group linked to B and has formula IV or a pharmaceutically acceptable salt thereof (IV)

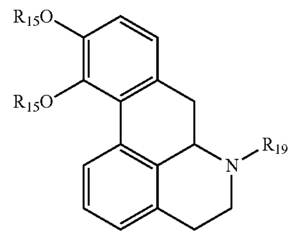

wherein one of $R_{15}$ or $R_{16}$ is L;

the other of $R_{15}$ or $R_{16}$ is B; and $R_{19}$ is H, an unsubstituted or substituted alkyl, unsubstituted or substituted alkenyl, unsubstituted or substituted alkynyl, unsubstituted or substituted cycloalkyl, unsubstituted or substituted aryl, unsubstituted or substituted benzyl, acyl, tetrahydrofuranyl, tetrahydropyranyl, nicotinyl or a 1-aryltetrazolyl;

B is $—R_{17}—R_{18}$, wherein $R_{17}$ is —C(O)—O—, —C(O)—NH-cyclic-O—C(O)—, —C(O)—NH—$(C_6H_4)$—O—C(O)—, $CH_3$ $(CH_2)_{1-4}$—O—C(O)—$(CH_2)_{1-4}$—C(O)— or P(O) $(OR_9)$(O)—, wherein cyclic represents substituted or unsubstituted aryl, heterocylalkyl, heteroaryl, heterocyclyl or cycloalkyl and $R_9$ is H or a substituted or unsubstituted C1-C5 alkyl, and wherein $R_{18}$ is an unsubstituted or substituted alkyl, an unsubstituted or substituted alkenyl, an unsubstituted or substituted aralkyl or an unsubstituted or substituted aryl group; and b is 1 to 50, provided that n is always greater than or equal to b, and wherein the first-cleavable moiety and B differ.

2. The conjugate of claim 1, wherein the water-soluble polymer is a poly(oxazoline) polymer.

3. The conjugate of claim 1, wherein the water-soluble polymer is a co-polymer.

4. The conjugate of claim 1, wherein the water-soluble polymer is a co-polymer comprising 50% to 99.5% of a poly(oxazoline) polymer.

5. The conjugate of claim 1, wherein L is a direct linkage or a linking group.

6. The conjugate of claim 1, wherein the first cleavable moiety is an ester linkage.

7. The conjugate of claim 1, wherein $R_{15}$ is L and $R_{16}$ is B.

8. The conjugate of claim 1, wherein $R_{19}$ is selected from the group consisting of —H, $—CH_3$, $—CH_2—CH_3$, $—CH_2—CH_2—CH_3$, $—CH(CH_3)_2—CH_2—CH_2—CH_2—CH_3$, and

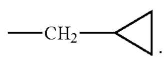

9. The conjugate of claim 8, wherein $R_{19}$ is $—CH_3$.

10. A conjugate comprising a poly(oxazoline) polymer (POZ) and an agent (A) and having the structure of formula IIB or a pharmaceutically acceptable salt thereof (IIB)

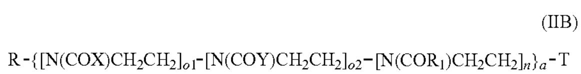

$R-\{[N(COX)CH_2CH_2]_{o1}-[N(COY)CH_2CH_2]_{o2}-[N(COR_1)CH_2CH_2]_n\}_a-T$ wherein R is an initiating group;

X is independently selected for each repeating unit from -L-A-B;

Y is independently selected for each repeating unit from -L-A-B, a non-reactive pendent moiety, or a pendent moiety containing an active functional group, and wherein X and Y may be the same or different;

$R_1$ is independently selected for each repeating unit from an unsubstituted or substituted alkyl, an unsubstituted or substituted alkenyl, an unsubstituted or substituted aralkyl, or an unsubstituted or substituted heterocyclylalkyl group;

a is ran which indicates a random co-polymer or block which indicates a block co-polymer;

o1 is an integer from 1 to 50;

o2 is from 0 to 49, provided that the sum of o1 and o2 is less than or equal to 50; and T is a terminating group;

n is an integer from 1-1000;

L is a linkage comprising a first cleavable moiety, linking A and POZ;

A comprises at least a first and a second phenolic hydroxyl group, wherein the first phenolic hydroxyl group is linked to L and the second phenolic hydroxyl group is linked to B, and wherein A is apomorphine;

B is $—R_{17}—R_{18}$, wherein $R_{17}$ is —C(O)—O—, —C(O)—NH-cyclic-O—C(O)—, —C(O)—NH—$(C_6H_4)$—O—C(O)—, $CH_3$ $(CH_2)_{1-4}$—O—C(O)—$(CH_2)_{1-4}$—C(O)— or P(O) $(OR_9)$ (O)—, wherein cyclic represents substituted or unsubstituted aryl, heterocylalkyl, heteroaryl, heterocyclyl or cycloalkyl and $R_9$ is H or a substituted or unsubstituted C1-C5 alkyl, and wherein $R_{18}$ is an unsubstituted or substituted alkyl, an unsubstituted or substituted alkenyl, an unsubstituted or substituted aralkyl or an unsubstituted or substituted aryl group; and b is 1 to 50, provided that n is always greater than or equal to b, and wherein the first cleavable moiety is different than B.

11. The conjugate of claim 10, wherein the L is a direct linkage or a linking group.

12. The conjugate of claim 11, wherein L is a linking group having structure

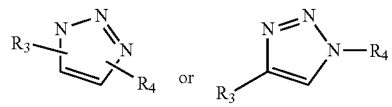

wherein $R_3$ links the triazole moiety to the POZ; and $R_4$ links the triazole moiety to A, and wherein $R_4$ forms a bond with the first phenolic hydroxyl of A.

13. The conjugate of claim 12, wherein:

$R_3$ is —C(O)—$R_5$—;

$R_5$ is absent or is an unsubstituted or substituted alkyl, an unsubstituted or substituted alkenyl, an unsubstituted or substituted aralkyl, or an unsubstituted or substituted heterocyclylalkyl group;

$R_4$ is $—R_6—R_7—R_8—$;

$R_6$ is a substituted or unsubstituted alkyl, substituted or unsubstituted aralkyl, or a oligo (ethylene oxide);

$R_7$ is a group containing the first cleavable moiety or a portion thereof; and $R_8$ is absent or O.

14. The conjugate of claim 13, wherein $R_7$ and $R_8$ combine to form the first cleavable moiety.

15. The conjugate of claim 13, wherein $R_6$ is a straight chain substituted or unsubstituted $C_1$-$C_4$ alkyl, or a branched substituted or unsubstituted $C_1$-$C_4$ alkyl, wherein $R_7$ is —C(O)—O—, and wherein $R_8$ is absent.

16. The conjugate of claim 13, wherein $R_6$ is a straight chain substituted or unsubstituted $C_1$-$C_4$ alkyl, or a branched substituted or unsubstituted $C_1$-$C_4$ alkyl, wherein $R_7$ is —C(O)—, and wherein $R_8$ is —O— or absent.

17. The conjugate of claim 12, wherein $R_3$ is —C(O)—$(CH_2)_3$ and $R_4$ is $—(CH_2)_d$—C(O)—O—, $—CH_2$—C(O)—O—, $—CH_2—CH_2$—C(O)—O—, $—CH_2—CH_2—CH_2$—C(O)—O—, or $—CH_2$ $(CH_3)$—C(O)—O—, wherein d is an integer from 1 to 10.

18. The conjugate of claim 12, wherein $R_3$ is —C(O)—$(CH_2)_3$ and $R_4$ is $—(CH_2)_d$—C(O)—, $—CH_2$—C(O)—, $—CH_2—CH_2$—C(O)—, $—CH_2—CH_2—CH_2$—C(O)—, or $—CH_2$ $(CH_3)$—C(O)—, wherein d is an integer from 1 to 10.

19. The conjugate of claim 10, wherein T is Z—$B_1$-Q, Z is S, O, or N, $B_1$ is an optional linking group, and Q is a terminating nucleophile.

20. The conjugate of claim 19, wherein $B_1$ is $—(CH_2)_{1-16}—$, Z is S, and Q is —COOH, $—COOCH_3$, $—NH_2$, or NH-tBoc.

21. The conjugate of claim 10, wherein $R_1$ is an unsubstituted or substituted alkyl.

22. The conjugate of claim 10, wherein the conjugate has the structure

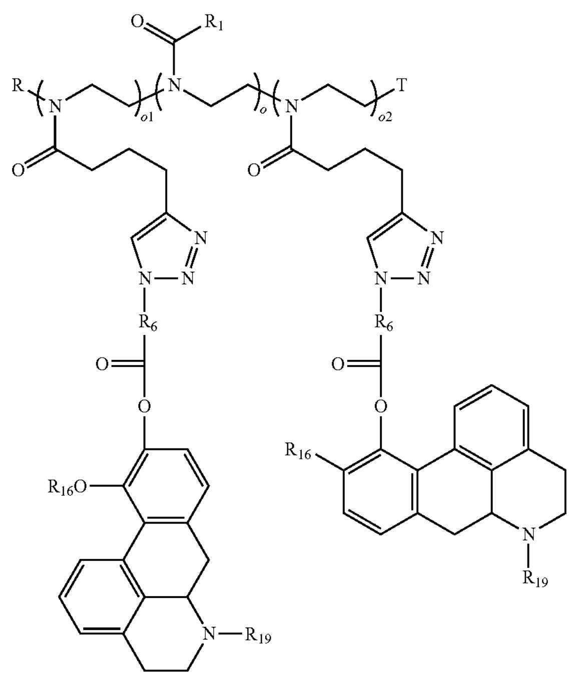

wherein $R_1$ is an unsubstituted or substituted alkyl, an unsubstituted or substituted alkenyl, an unsubstituted or substituted aralkyl, or an unsubstituted or substituted heterocyclylalkyl group; $R_6$ is a substituted or unsubstituted alkyl or aryl group; $R_{16}$ is B.

23. The conjugate of claim 10, wherein the first cleavable moiety comprises a carbonate ester linkage (—O—C(O)—O—), a carbamate linkage (—O—C(O)—NH—), an amide linkage (—C(O)—NH—), or a disulfide linkage (S—S).

24. A method of treating a dopamine-responsive disease or condition in a subject, the method comprising administering to the subject an amount of the conjugate of formula I of claim 1.

25. The method of claim 24, wherein the dopamine-responsive disease or condition is Parkinson's disease, restless leg syndrome, pituitary tumors, schizophrenia, attention-deficit hyperactivity disorder, SSRI-induced sexual dysfunction, depression, obesity, or type II diabetes.

26. A method of treating a dopamine-responsive disease or condition in a subject, the method comprising administering to the subject an amount of the conjugate of formula (IIB) of claim 10.

27. The method of claim 26, wherein the dopamine-responsive disease or condition is Parkinson's disease, restless leg syndrome, pituitary tumors, schizophrenia, attention-deficit hyperactivity disorder, SSRI-induced sexual dysfunction, depression, obesity, or type II diabetes.

* * * * *